(12) United States Patent
Hong et al.

(10) Patent No.: US 8,946,289 B2
(45) Date of Patent: Feb. 3, 2015

(54) MANASSATIN COMPOUNDS AND METHODS OF MAKING AND USING THE SAME

(75) Inventors: Jiyong Hong, Durham, NC (US); Mark Dewhirst, Durham, NC (US); Hyoungsu Kim, Durham, NC (US); Amanda C. Kasper, Derby, NY (US); Eui Jung Moon, Durham, NC (US); Yongho Park, Durham, NC (US); Ceshea M. Wooten, Plano, TX (US)

(73) Assignee: Duke University, Durham, NC (US)

( * ) Notice: Subject to any disclaimer, the term of this patent is extended or adjusted under 35 U.S.C. 154(b) by 421 days.

(21) Appl. No.: 13/130,237

(22) PCT Filed: Nov. 19, 2009

(86) PCT No.: PCT/US2009/065194
§ 371 (c)(1),
(2), (4) Date: May 19, 2011

(87) PCT Pub. No.: WO2010/059858
PCT Pub. Date: May 27, 2010

(65) Prior Publication Data
US 2011/0230540 A1 Sep. 22, 2011

Related U.S. Application Data

(60) Provisional application No. 61/116,096, filed on Nov. 19, 2008, provisional application No. 61/118,940, filed on Dec. 1, 2008.

(51) Int. Cl.
*C07D 307/12* (2006.01)
*A61K 31/341* (2006.01)
*A61K 31/40* (2006.01)
*C07D 407/12* (2006.01)

(52) U.S. Cl.
CPC ............ *A61K 31/341* (2013.01); *A61K 31/40* (2013.01); *C07D 307/12* (2013.01); *C07D 407/12* (2013.01)
USPC .......................................... 514/461; 549/502

(58) Field of Classification Search
None
See application file for complete search history.

(56) References Cited

FOREIGN PATENT DOCUMENTS

| WO | WO 01/87869 | 11/2001 |
| WO | WO 2004/110348 | 12/2004 |

OTHER PUBLICATIONS

Hanessian, et al., Org. Lett., 8:5477 (2006).*
Becke, A. D. *J Chem. Phys.* 1993,98,5648.
Becke, A. D. *Phys. Rev. A* 1988, 38, 3098.
Brown, D. S. et al. *Tetrahedron* 1989, 45, 4293-4308.
Brown, D. S. et al. *Tetrahedron Lett.* 1988, 29, 4869-4872.
C.T. F.A. Cosmetic Ingredient Handbook, 1992, pp. 587-592.
Corey, E. J. et al. *Chem., Int. Ed. Engl.*, 1998, 37, 1986-2012.
Evans, D. A. et al. *Org. Lett.* 2002, 4, 1127-1130.
Hahm Jong-Cheon et al.: "Cytotoxicity of Neolignans identified in Saururus chinensis towards human cancer cell lines" Planta Medica, vol. 71, No. 5, May 1, 2005, pp. 464-469, XP002549220.
Hodge, M. B. et al. *Tetrahedron* 2004, 60, 9397-9403.
Hodges, Tyler W. et al. "Molecular-targeted antitumor agents: the Saururus cernuus dineolignans manassantin Band 4-0-demethylmanassantin B are potent inhibitors of hYPoxia-activated HIF-1" Journal of Natural Products, American Chemical Society, US, vol. 67, No. 5, May 1, 2004, pp. 767-771, XP002515007 ISSN: 0163-3864.
Hossain, C. F. et al. "*Saururus cernuus* lignans-Potent small molecule inhibitors of hypoxia-inducible factor-1" *Biochem. Biophys. Res. Commun.* 2005, 333, pp. 1026-1033.
Kim, H. et al. *Am. Chern. Soc.* 2009, 131, 3192-3194.
Kim, H. et al. *Org. Lett.* 2007, 9, 3965-3968.
Kim, H. et al. *Org. Lett.* 2009, 11, 89-92.
Lee, A-L. et al.*Org. Biomol. Chem.* 2003, 1, 3957-3966.
Lee, C. et al. *Phys. Rev. B* 1988, 37, 785-789.
Lee, Jeong-Hyung et al. "Suppression of RelA/p65 transactivation activity by a lignoid manassantin isolated from Saururus chinensis." Biochemical Pharmacology Nov. 15, 2003, vol. 66, No. 10, Nov. 15, 2003, pp. 1925-1933, XP002562337 ISSN: 0006-2952.
Li, F. et al. *Mol. Cell* 2007, 26, 63-74.
Mandal, M.; et al. *J. Org. Chem.* 2005, 70, 10619-10637.
McCutcheon's vol. I, Emulsifiers & Detergents, 1994, North American Edition, pp. 236-239.
McIntyre, S. et al. *Adv. Synth. Catal.* 2005, 347, 282-288.
Park Hee-Juhn et al. "Saucernetin-7 and saucernetin-8 isolated from Saururus chinensis inhibit the LPS-induced production of nitric oxide and prostaglandin E2 in macrophage RAW264.7 cells" Planta Medica vol. 69, No. 10, Oct. 2003 pp. 947-950, XP018002279 ISSN: 0032-0943.
Remington's Pharmaceutical Sciences, 15th Ed. 1975, pp. 335-337.
Schreiber, J. et al. *Chem.,Int. Ed. Engl.* 1971, 10,330-331.
Seo Bo-Rim et al. "Saucernetin-8 isolated from Saururus chinensis induced the differentiation of human acute promyelocytic leukemia HL-60 cells" Biological &Pharmaceutical Bulletin vol. 27, No. 10, Oct. 2004 pp. 1594-1598, XP002562336 ISSN: 0918-6158.
Skehan, P., et al., 1990, *J. Natl. Cancer Inst.*, 82, 1107-1112.

(Continued)

*Primary Examiner* — Michael Barker
(74) *Attorney, Agent, or Firm* — Michael Best & Friedrich LLP

(57) ABSTRACT

Provided are manassantin compounds and methods of using the compounds. Provided are methods of treating a disease, the method comprising administering a compound according to Formula I. Further provided are pharmaceutical compositions comprising compounds according to Formula I. Also provided are methods of inhibiting HIF-1 in a cell, the methods comprising administering to the cell a compound according to Formula I.

23 Claims, 28 Drawing Sheets

(56) References Cited

OTHER PUBLICATIONS

Song S-Y et al. "Neolignans from Saururus chinensis inhibit PC-3 prostate cancer cell growth via apoptosis and senescence-like mechanisms" International Journal of Molecular Medicine, Spandidos, Athens, GR, vol, 16, No. 4, Oct. 1, 2005, pp. 517-523, XP008113079 ISSN: 1107-3756.
Vosko, S.; Wilk, L.; Nusair, M. Can. *J. Phys*. 1980, 58, 1200.
Wang, G. L. et al. *Blood* 1993, 82, 3610.
Zhang, X. et al. *Cancer Res*. 2004, 64, 8139.
PCT/US2009/065194 International Search Report and Written Opinion dated Jan. 25, 2010 (15 pages).
Amanda C. Kasper et al. "Analysis of HIF-1 inhibition by manassantin A and analogues with modified tetrahydrofuran configurations" Bioorganic & Medicinal Chemistry Letters 19 (2009) 3783-3786.
Kim et al. "Inhibition of Phenotypic and Functional Maturation of Dendritic Cells by Manassantin A" Journal of Pharmacological Sciences, Feb. 13, 2009.

* cited by examiner

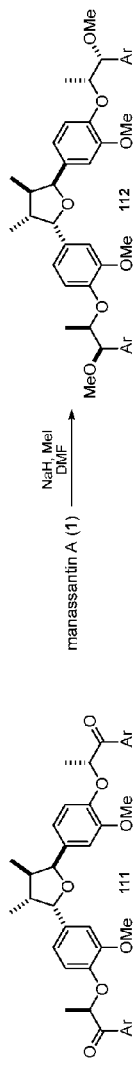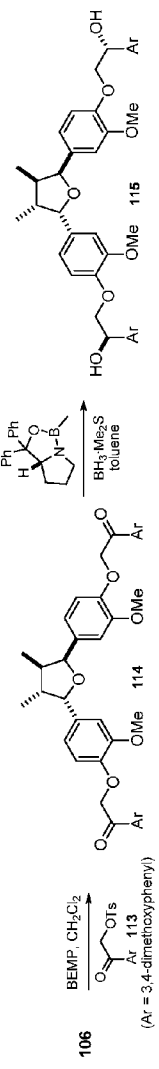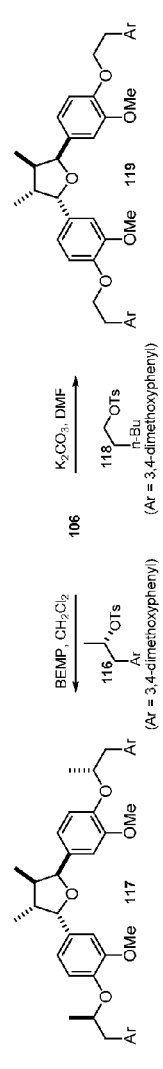
FIG. 29
FIG. 30
FIG. 31

MANASSATIN COMPOUNDS AND METHODS OF MAKING AND USING THE SAME

CROSS-REFERENCE TO RELATED APPLICATIONS

This patent application is a national stage filing under 35 U.S.C. 371 of International Application No. PCT/US2009/065194, filed Nov. 19, 2009, which claims the benefit of priority to U.S. Provisional Application No. 61/116,096, filed Nov. 19, 2008, and U.S. Provisional Application No. 61/118,940, filed on Dec. 1, 2008, the disclosures of each of which are incorporated by reference herein in their entireties. Priority to each application is hereby claimed.

TECHNICAL FIELD

The present invention is directed to novel manassantin compounds and analogues thereof and methods of making and using the same.

BACKGROUND OF THE INVENTION

Hypoxia-inducible factors (HIFs) are transcription factors that respond to cellular changes in oxygen levels, and specifically, to a condition of low physiological oxygen levels known as hypoxia. Most, if not all, oxygen-consuming species express HIF-1, which is a heterodimeric transcriptional complex comprised of an alpha and a beta subunit. The related protein HIF-2α can also dimerize with HIF-1β. Heterodimers that contain HIF-1α or HIF-2α seem to have overlapping but distinct specificities, with regard to physiological inducers and target-gene activation. HIF-3α is a third related protein that may function primarily as an inhibitor of HIF-1α.

The HIF pathway mediates the effects of hypoxia. HIF-1 upregulates several genes, including glycolysis enzymes and vascular endothelial growth factor (VEGF). Hypoxia affects an organism in many ways, including inhibiting cellular differentiation, promoting formation of blood vessels, promoting the formation of the vascular system in embryos, and promoting the migration of karatinocytes and the restoration of the epithelium in wounds.

SUMMARY OF THE INVENTION

The present invention provides a method of treating a disease, the method comprising administering to a patient in need thereof an effective amount of a compound according to Formula I:

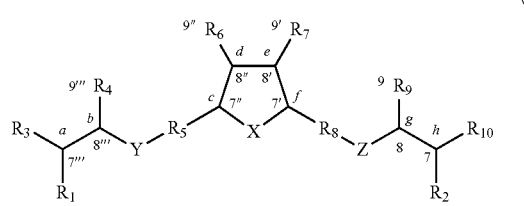

(I)

with variables as detailed below. The disease may be selected from the group consisting of leukemia, lung cancer, colon cancer, CNS cancer, melanoma, ovarian cancer, renal cancer, liver cancer, prostate cancer, breast cancer, stroke, heart disease, arthritis, ocular neovascular diseases, inflammation, kidney disease, and anemia.

In another embodiment, the invention provides a pharmaceutical composition comprising a pharmaceutically acceptable carrier and a compound according to Formula I.

In other embodiments, the invention provides compounds according to Formula I.

In addition, the present invention provides methods of inhibiting HIF-1 comprising contacting a cell with a compound according to Formula I, in an amount effective to inhibit the HIF-1 pathway.

In another embodiment, the invention provides a method of potentiating a cancer cell for treatment with ionizing radiation or chemotherapeutics, the method comprising contacting the cancer cell with an effective amount of a compound according to Formula I.

BRIEF DESCRIPTION OF THE DRAWINGS

FIG. 14 is a table of the $GI_{50}$, TGI, and $LC_{50}$ determined for the effect of manassantin A on various human cancer cell lines (trial 1).

FIG. 17 is a table of the $GI_{50}$, TGI, and $LC_{50}$ determined for the effect of manassantin A on various human cancer cell lines (trial 2).

Figure 20:
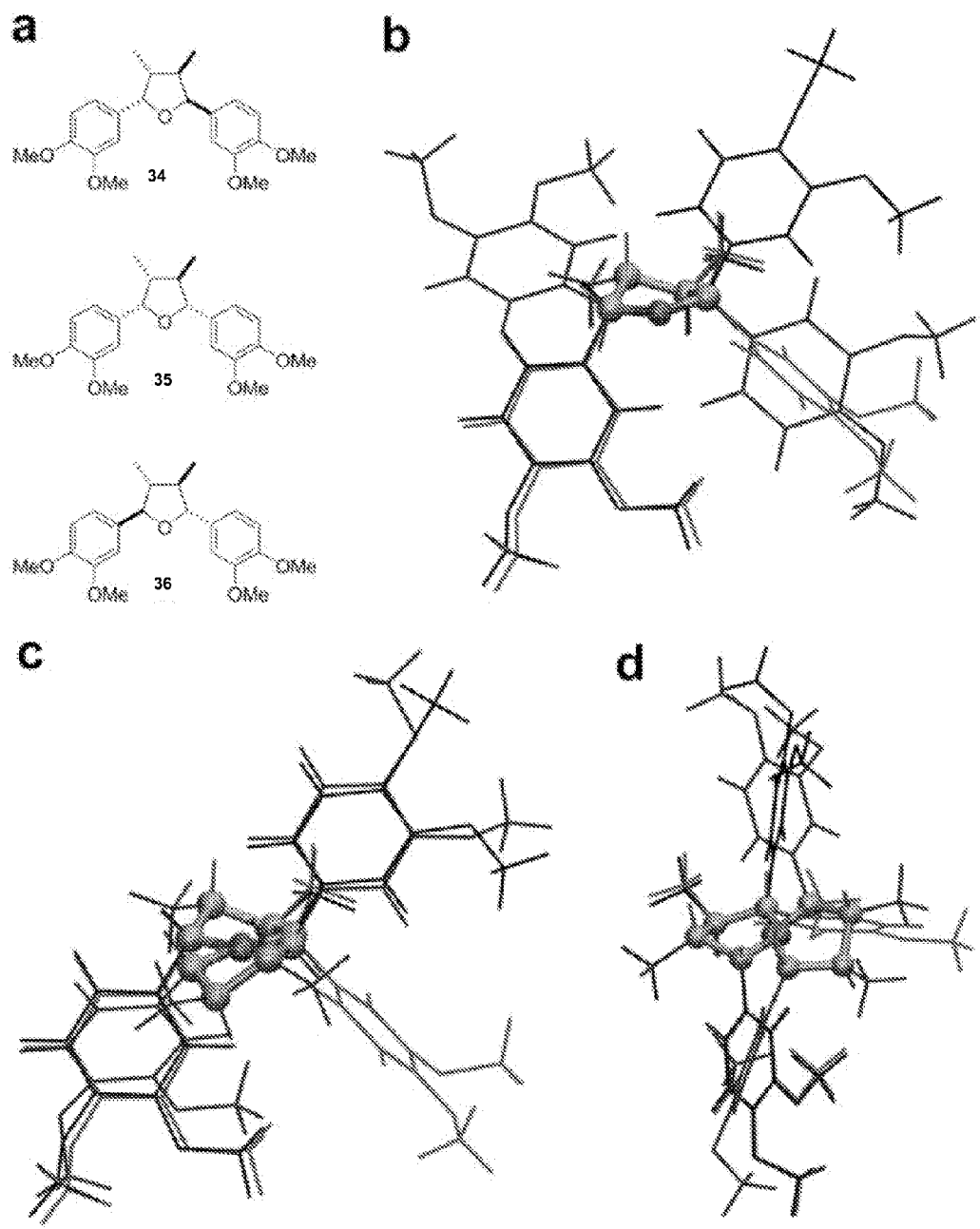

FIG. 20 shows the optimized conformations of truncated structures of manassantin A, 31, and 33.

Figure 21:
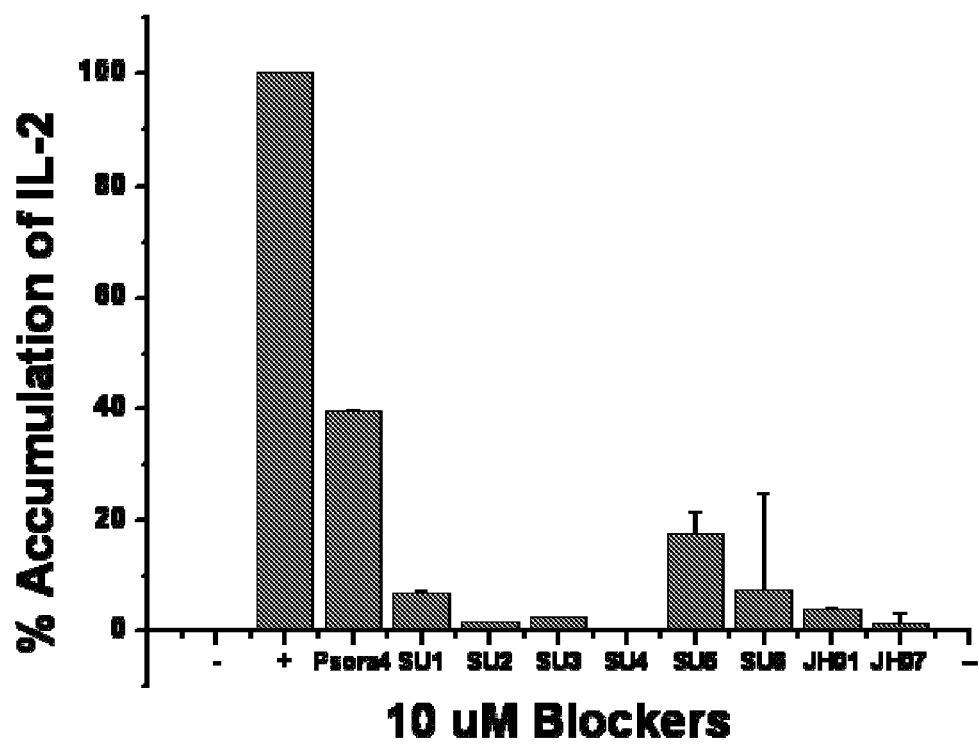

FIG. 21 is a graph of compound concentration versus accumulation of IL-2 for an inflammation inhibition assay.

Figure 22:
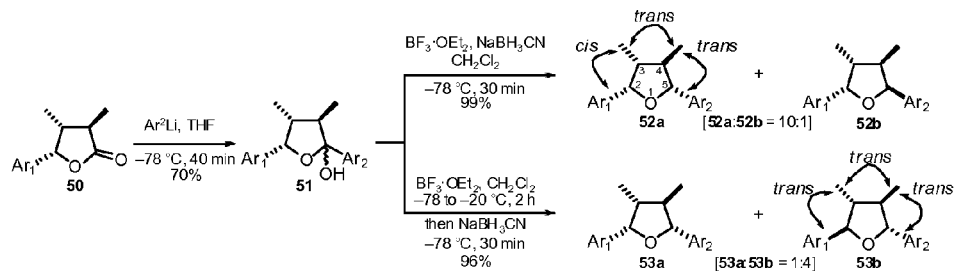

FIG. 22 is a scheme for the chemical synthesis of 2,3-cis-3,4-trans-4,5-trans-(52a) and 2,3-trans-3,4-trans-4,5-trans-tetrahydrofurans (53b).

Figure 23:
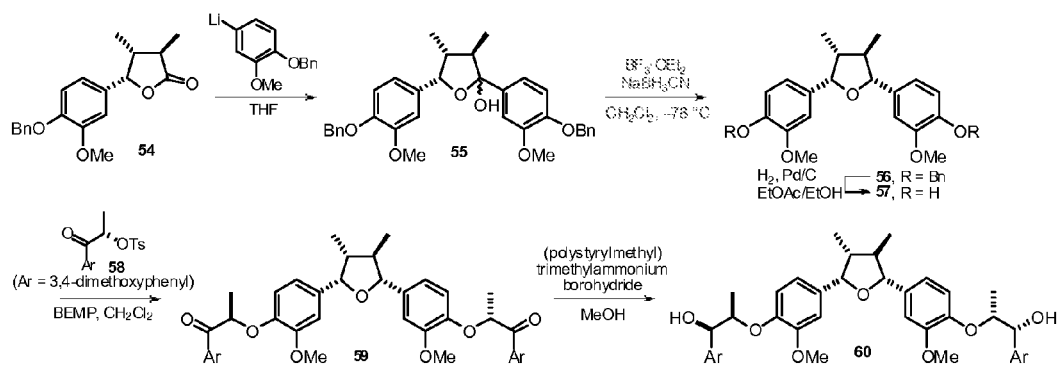

FIG. 23 is a scheme for the chemical synthesis of 2,3-cis-3,4-trans-4,5-trans-terahydrofuran analogue (60).

Figure 24:
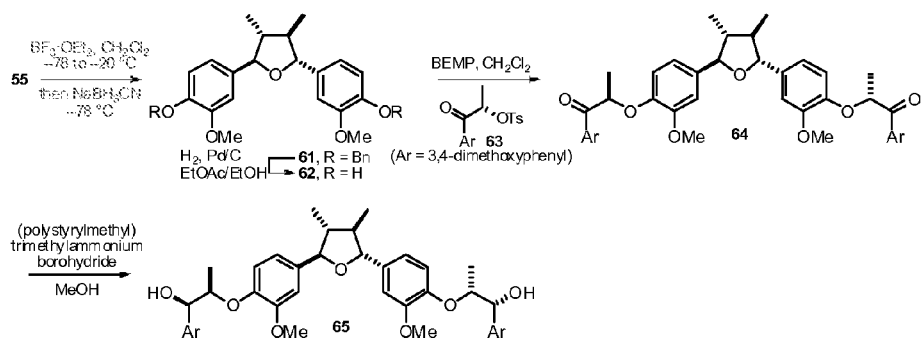

FIG. 24 is a scheme for the chemical synthesis of 2,3-trans-3,4-trans-4,5-trans-terahydrofuran analogue (65).

Figure 25:
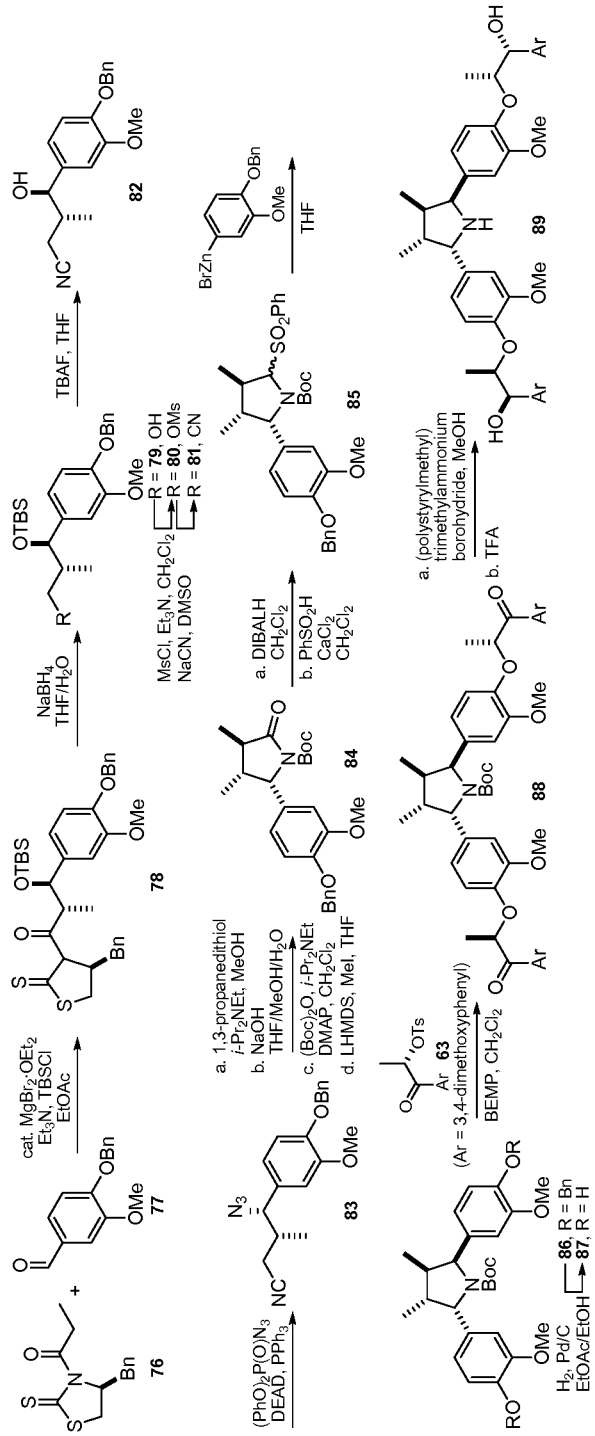

FIG. 25 is a scheme for the chemical synthesis of pyrrolidine analogue (89).

Figure 26:
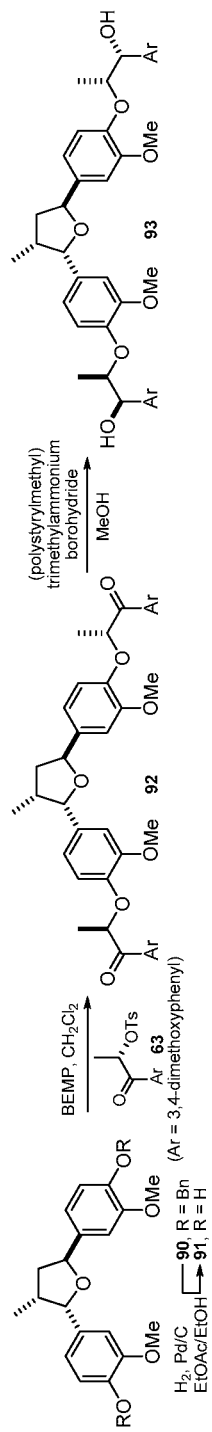

FIG. 26 is a scheme for the chemical synthesis of C9'' mono-methyl analogue (93).

Figure 27:
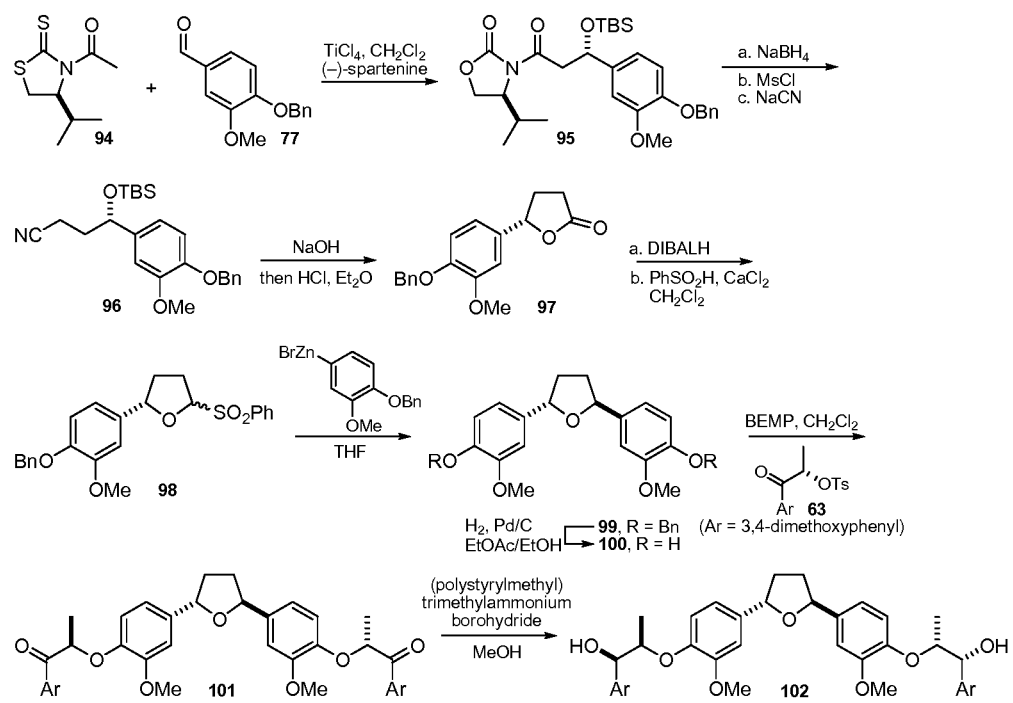

FIG. 27 is a scheme for the chemical synthesis of C9' and C9'' desmethyl analogue (102).

Figure 28:
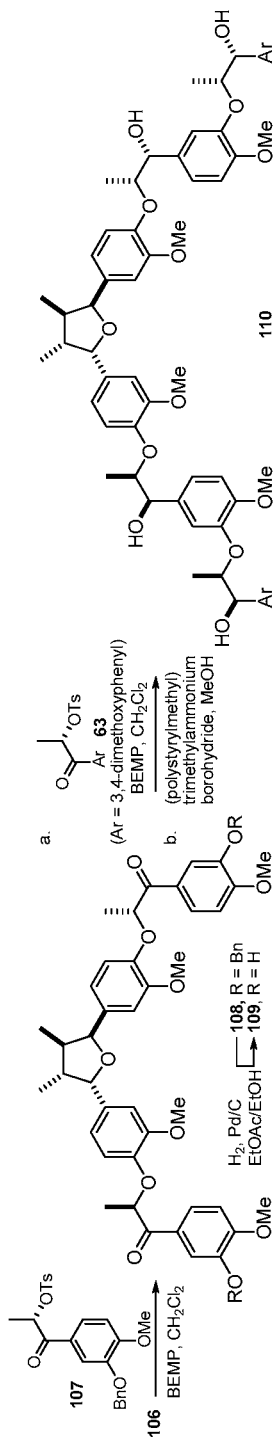

FIG. 28 is a scheme for the chemical synthesis of extended chain analogue (110).

FIG. 29 is a scheme for the chemical synthesis of keto analogue (111) and methoxy analogue (112).

FIG. 30 is a scheme for the chemical synthesis of a C9 and C9''' desmethyl analogue (115).

FIG. 31 is a scheme for the chemical synthesis of C7 and C7''' de-oxo analogues (117 and 119).

Figure 32:
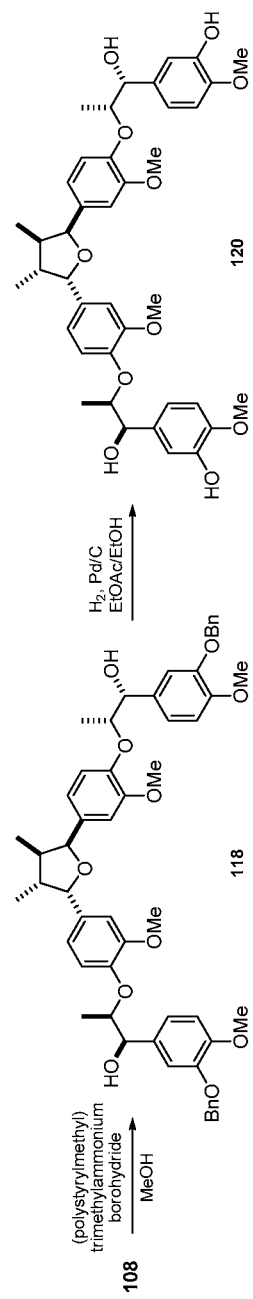

FIG. 32 is a scheme for the chemical synthesis of a C4 and C4''' hydroxyl analogue (120).

DETAILED DESCRIPTION OF THE INVENTION

The present invention is directed to novel manassantin compounds and stereospecific analogues thereof as well as methods of making and using the compounds of the present invention. The inventors have discovered that manassantins A, B, and analogues thereof may be chemically synthesized stereospecifically through nucleophilic addition of organozinc reagents to 2-benzenesulfonyl cyclic ethers to achieve the 2,3-cis-3,4-trans-4,5-cis-tetrahydrofuran moiety, to which side chains may be attached to form the manassantin compounds. The manassantin compounds are useful in methods of treating disorders or diseases such as cancer, stroke, heart disease, arthritis, ocular neovascular diseases, inflammation, kidney disease, tissue ischemia, and anemia. Cancers include but are not limited to leukemia, lung cancer, colon cancer, CNS cancer, melanoma, ovarian cancer, renal cancer, liver cancer, prostate cancer, and breast cancer. Further, the methods of the present invention are useful for stereoselective synthesis of manassantin compounds and analogues.

Definitions and Usage of Terms

"Alkyl" refers to a saturated or unsaturated hydrocarbon chain having 1 to 18 carbon atoms, suitably 1 to 12 carbon atoms, or 1 to 6 carbon atoms, or 1 to 4 carbon atoms. "Lower alkyl" refers to a saturated or unsaturated hydrocarbon chain having 1 to 4 carbon atoms. Alkyl groups may be straight or branched. In some embodiments, branched alkyl groups have one or two branches. Unsaturated alkyl groups have one or more double bonds and/or one or more triple bonds. Suitably, unsaturated alkyl groups have one or two double bonds or one triple bond. Alkyl chains may be unsubstituted or substituted with from 1 to about 4 substituents unless otherwise specified. Suitably, alkyl groups are mono-, di-, or tri-substituted. Suitable alkyl substituents include, but are not limited to, cyano, halo, hydroxy, aryl (e.g., phenyl, tolyl, alkyloxphenyl, alkyloxycarbonylphenyl, halophenyl), heterocyclyl, and heteroaryl.

"Aromatic ring" or "aryl" refers to an aromatic hydrocarbon ring system. Aromatic rings are monocyclic or fused bicyclic ring systems. Monocyclic aromatic rings contain from about 5 to about 10 carbon atoms, suitably from 5 to 7 carbon atoms, or from 5 to 6 carbon atoms in the ring. Bicyclic aromatic rings contain from 8 to 12 carbon atoms, suitably 9 or 10 carbon atoms in the ring. Aromatic rings may be unsubstituted or substituted with from 1 to about 4 substituents on the ring. Suitable aromatic ring substituents include, but are not limited to, halo, cyano, lower alkyl, heteroalkyl, haloalkyl, phenyl, phenoxy or any combination thereof. Suitably, the aromatic ring substituents are lower alkyl, cyano, halo, or halo alkyl.

"Carbocycle" refers to a saturated or unsaturated hydrocarbon ring. Carbocycles are not aromatic. Carbocycles are monocyclic, or are fused, spiro, or bridged bicyclic ring systems. Monocyclic carbocycles contain from about 4 to about 10 carbon atoms, suitably from 4 to 7 carbon atoms, or from 5 to 6 carbon atoms in the ring. Bicyclic carbocycles contain from 8 to 12 carbon atoms, suitably from 9 to 10 carbon atoms in the ring. Carbocycles may be unsubstituted or substituted with from 1 to about 4 substituents on the ring. Suitable carbocycle substituents include, but are not limited to, halo, cyano, lower alkyl, heteroalkyl, haloalkyl, phenyl, phenoxy or any combination thereof. Suitably, the carbocycle substituents are halo or haloalkyl. Suitable carbocycles include, but are not limited to, cyclopentyl, cyclohexyl, cyclohexenyl, cycloheptyl, and cyclooctyl.

"Halo" or "halogen" refers to fluoro, chloro, bromo, or iodo.

"Haloalkyl" refers to a straight, branched, or cyclic hydrocarbon substituted with one or more halo substituents. Suitably, the haloalkyl is $C_1$-$C_{12}$, or $C_1$-$C_6$, or $C_1$-$C_3$. Suitable halo substituents include fluoro and chloro. One suitable haloalkyl is trifluoromethyl.

"Heteroalkyl" refers to a saturated or unsaturated chain containing carbon and at least one heteroatom, wherein no two heteroatoms are adjacent. Heteroalkyl groups contain from 1 to 18 member atoms (carbon and heteroatoms) in the chain, or 1 to 12 member atoms, or 1 to 6 member atoms, or 1 to 4 member atoms. Heteroalkyl groups may be straight or branched. Suitably, the branched heteroalkyl may have one or two branches. Unsaturated heteroalkyl have one or more double bonds and/or one or more triple bonds. Suitably, heteroalkyl groups have one or two double bonds or one triple bond. Heteroalkyl groups may be unsubstituted or substituted with from 1 to about 4 substituents unless otherwise specified. Suitable heteroalkyl substituents include halo, aryl (e.g., phenyl, tolyl, alkyloxyphenyl, alkyloxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e.g., amino, mono- and di-$C_1$-$C_3$ alkanylamino, methylphenylamino, methylbenzylamino, $C_1$-$C_3$ alkanylamido, carbamamido, ureido, guanidino).

"Heteroatom" refers to a nitrogen, sulfur, or oxygen atom. Groups containing more than one heteroatom may contain different heteroatoms. As used herein, halogens are not heteroatoms.

"Heterocycle" refers to a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocycles are not aromatic. Heterocycles are monocyclic, or are fused or bridged bicyclic ring systems. Monocyclic heterocycles contain from about 4 to about 10 member atoms (carbon and heteroatoms), suitably from 4 to 7 member atoms, or from 5 to 6 member atoms in the ring. Bicyclic heterocycles contain from 8 to 12 member atoms, suitably 9 or 10 member atoms in the ring. Heterocycles may be unsubstituted or substituted with from 1 to about 4 substituents on the ring. Suitably, the substituents are halo or haloalkyl. Suitable heterocycle substituents include: halo, cyano, lower alkyl, heteroalkyl, haloalkyl, phenyl, phenoxy or any combination thereof. Suitable heterocycles include, but are not limited to, piperzyl, morpholinyl, tetrahydrofuranyl, tetrahydropyranyl, and piperdyl.

"Heteroaryl" refers to an aromatic ring system containing carbon and from 1 to about 4 heteroatoms in the ring. Heteroaryls are monocyclic or fused bicyclic ring systems. Monocyclic heteroaryls contain from about 5 to about 10 member atoms (carbon and heteroatoms), or from 5 to 7 member atoms, or from 5 to 6 member atoms in the ring. Bicyclic heteroaryls contain from 8 to 12 member atoms, or 9 or 10 member atoms in the ring. Heteroaryls may be unsubstituted or substituted with from 1 to about 4 substituents on the ring. Suitable heteroaryl substituents include: halo, cyano, lower alkyl, heteroalkyl, haloalkyl, phenyl, phenoxy, or any combination thereof. Suitably, the substituents are halo, haloalkyl, or phenyl. Suitable heteroaryls include, but are not limited to, benzothienyl, benzofuranyl, thienyl, thiazolo, purinyl, pyrimidyl, pyridyl, and furanyl.

"Lower alkyl" refers to an alkyl chain comprised of 1 to 4 carbon atoms, suitably 1 to 3 carbon atoms or 1 to 2 carbon atoms. Lower alkyl groups may be saturated or unsaturated and substituted or unsubstituted. Lower alkyl groups include, but are not limited to, methyl, ethyl, propyl, isopropyl, butyl, isobutyl, and t-butyl.

"Lower heteroalkyl" refers to a heteroalkyl chain comprised of 1 to 4 member atoms. Lower heteroalkyl groups may be saturated or unsaturated and substituted or unsubstituted.

"Member atom" refers to a polyvalent atom (C, O, N, or S atom) in a chain or ring system that continues the chain or ring system. For example, in benzene the six carbon atoms are member atoms and the six hydrogen atoms are not member atoms.

"Phenyl" refers to a six-membered monocyclic aromatic ring which may or may not be substituted with from about 1 to about 4 substituents. The substituents may be substituted at the ortho, meta or para position on the phenyl ring, or any combination thereof. Suitable phenyl substituents include: halo, cyano, lower alkyl, heteroalkyl, haloalkyl, phenyl, phenoxy or any combination thereof.

The above groups, whether alone or part of another substituent, may themselves optionally be substituted with one or more groups selected from themselves and the additional substituents listed below.

Halo: —F, —Cl, —Br, and —I.
Hydroxy: —OH.
Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —$NO_2$.
Cyano (nitrile, carbonitrile): —CN.
Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C($CH_3$)$_3$ (butyryl), and —C(=O)Ph (benzoyl, phenone).

Carboxy (carboxylic acid): —COOH.
Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)O$CH_3$, —C(=O)O$CH_2CH_3$, —C(=O)OC($CH_3$)$_3$, and —C(=O)OPh.

Amido (carbamoyl, carbamyl, aminocarbonyl, carboxamide): —C(=O)N$R^1R^2$, wherein $R^1$ and $R^2$ are independently amino substituents, as defined for amino groups. Examples of amido groups include, but are not limited to, —C(=O)$NH_2$, —C(=O)NH$CH_3$, —C(=O)N($CH_3$)$_2$, —C(=O)NH$CH_2CH_3$, and —C(=O)N($CH_2CH_3$)$_2$. as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —N$R^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group. or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —$NH_2$, —NH$CH_3$, —NHCH($CH_3$)$_2$, —N($CH_3$)$_2$, —N($CH_2CH_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. In particular, the cyclic amino groups may be substituted on their ring by any of the substituents defined here, for example carboxy, carboxylate and amido.

Acylamido (acylamino): —N$R^1$C(=O)$R^2$, wherein $R^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and $R^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)$CH_3$, —NHC(=O)$CH_2CH_3$, and —NHC(=O)Ph. $R^1$ and $R^2$ may together form a cyclic structure, as in, for example, succinimidyl, maleimidyl, and phthalimidyl.

Ureido: —N($R^1$)CON$R^2R^3$ wherein $R^2$ and $R^3$ are independently amino substituents, as defined for amino groups, and $R^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCON$H_2$, —NHCONHMe, —NHCONHEt, —NHCONMe$_2$, —NH- CONEt$_2$, —NMeCONH$_2$, —NMeCONHMe, —NMeCON-HEt, NMeCONMe$_2$, —NMeCONEt$_2$, and —NHCONHPh.

Acyloxy (reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)C$_6$H$_4$F, and —OC(=O)CH$_2$Ph.

Oxo: =O.

Thiol: —SH.

Thioether (sulfide): —SR, wherein R is a thioether substituent, for example, a C$_{1-7}$ alkyl group (also referred to as a C$_{1-7}$ alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Sulfoxide (sulfinyl): —S(=O)R, wherein R is a sulfoxide substituent, for example, a C$_{1-7}$ alkyl group, a C$_{3-20}$ heterocyclyl group, or a C$_{5-20}$ aryl group, preferably a C$_{1-7}$ alkyl group. Examples of sulfoxide groups include, but are not limited to, —S(=O)CH$_3$ and —S(=O)CH$_2$CH$_3$.

Sulfonyl (sulfone): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_a$, —C(=S)N(CH$_3$)$_2$, and —C(=S)NHCH$_2$CH$_3$.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

Other definitions include:

"Protected" refers to a chemical structure wherein one or more of the chemically-sensitive groups in the molecule have been modified to reduce its activity and allow for better synthetic techniques to be used. Protecting groups vary but are generally found in "Protecting Groups in Organic Synthesis" by Theadora Green.

"Unprotected" refers to a chemical structure that does not contain any groups that have been added to protect sensitive functional moieties such as hydroxy groups or carboxylic acid groups.

"Pharmaceutically acceptable carrier" refers to a carrier that is useful for the preparation of a pharmaceutical composition that is generally compatible with the other ingredients of the composition, not deleterious to the recipient, and neither biologically nor otherwise undesirable. "A pharmaceutically acceptable carrier" includes both one and more than one carrier. Embodiments include carriers for topical, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions.

"Effective amount" refers to a dosage of the compounds or compositions effective for eliciting a desired effect. This term as used herein may also refer to an amount effective at bringing about a desired in vivo effect in an animal, preferably, a human, such as inhibition of HIF-1.

"Excipient" refers to a physiologically compatible additives useful in preparation of a pharmaceutical composition. Examples of pharmaceutically acceptable carriers and excipients can for example be found in Remington Pharmaceutical Science, 16th Ed.

"Administering" refers to administration of the compounds as needed to achieve the desired effect. Administration may include, but is not limited to, oral, sublingual, intramuscular, subcutaneous, intravenous, transdermal, topical, parenteral, buccal, rectal, and via injection, inhalation, and implants.

The term "contacting a cell" is used to mean contacting a cell in vitro, ex vivo, or in vivo (i.e. within a subject, such as a mammal, including humans, mice, rats, rabbits, cats, and dogs). Contacting may occur as a result of administration to a subject.

"Inhibiting HIF-1" refers to direct or indirect inhibition of HIF-1, including but not limited to reducing the activity of HIF-1, reducing the expression of HIF-1, preventing activity of HIF-1.

"Reducing proliferation of a cell" refers to reducing, inhibiting, or preventing the growth or differentiation of a cell, including killing a cell.

"Manassantins" and "manassantin compounds" refer to manassantin compounds including manassantin A, manassantin B, manassantin B$_1$, 4-O-demethylmanassantin B, and analogues thereof, whether synthetic or naturally occurring.

Manassantin Compounds

The present invention is directed to novel manassantin compounds. In some embodiments, the compounds according to the present invention are those according to Formula I below:

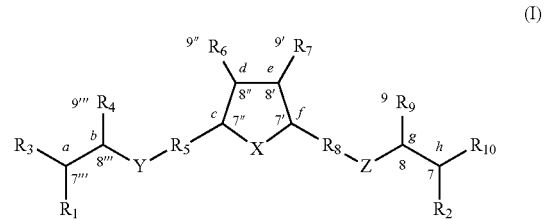

(I)

In Formula I, R$_4$, R$_6$, R$_7$, and R$_9$ are independently selected from alkyl, heteroalkyl, aryl, heteroaryl, ester, acyl, sulfonyl, heterocyclyl, amido, thioamido, acetyl, hydroxyl, amino, hydrogen, halogen, and cyano. In some embodiments, R$_4$, R$_6$, R$_7$, and R$_9$ are independently OH, hydrogen, oxo, methoxy, or lower alkyl. In some embodiments, R$_4$, R$_6$, R$_7$, and R$_9$ are independently lower alky. In some embodiments, R$_4$, R$_6$, R$_7$, and R$_9$ are independently methyl. In some embodiments, R$_4$, R$_6$, R$_7$, and R$_9$ are independently hydrogen.

X, Y, and Z are independently selected from the group consisting of CR$_{13}$, O, S, and NR$_{14}$, wherein R$_{13}$ and R$_{14}$ are independently selected from the group consisting of alkyl, heteroalkyl, aryl, heteroaryl, ester, acyl, sulfonyl, heterocyclyl, amido, thioamido, acetyl, hydroxyl, amino, hydrogen, halogen, and cyano. In some embodiments, X, Y, and Z are independently O.

R$_3$ and R$_{10}$ are independently selected from the group consisting of hydroxyl, hydrogen, alkyl, heteroalkyl, and oxo. In some embodiments, R$_3$ and R$_{10}$ are independently OH, hydrogen, oxo, methoxy, or lower alkyl. In some embodiments, R$_3$ and R$_{10}$ are independently methyl or methoxy.

$R_5$ and $R_8$ are independently selected from the group consisting of substituted or unsubstituted phenyl, C=C, and C≡C. In some embodiments, $R_5$ and $R_8$ are methoxy-substituted phenyl groups.

$R_1$ and $R_2$ are independently selected from the group consisting of aryl, heteroaryl, and substituted or unsubstituted phenyl of Formula II below:

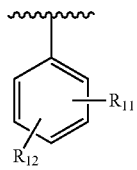
(II)

wherein $R_{11}$ and $R_{12}$ are independently selected from the group consisting of alkyl, heteroalkyl, aryl, heteroaryl, ester, acyl, sulfonyl, heterocyclyl, amido, thioamido, acetyl, hydroxyl, amino, hydrogen, halogen, oxo, substituted alkylaryl, and cyano, or $R_{11}$ and $R_{12}$ combine to form a ring. In some embodiments, $R_{11}$ and $R_{12}$ combine to form a ring comprising —O—$CH_2$—O—. In some embodiments, $R_1$ and $R_2$ are of Formula II wherein $R_{11}$ and $R_{12}$ are methoxy.

At all stereocenters in Formula I above, both epimers are envisioned. In some embodiments, the bond between $R_5$ and the center 5-membered heterocyclic ring, and the bond between $R_8$ and the center 5-membered heterocyclic ring, i.e. bonds c and f, are trans to each other, for Example, as shown below:

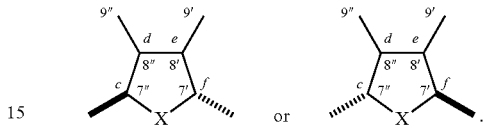

Suitably, $R_1$ and $R_2$ are of Formula II with $R_{11}$ and $R_{12}$ methoxy groups; X, Y, and Z are suitably O; $R_6$ and $R_7$ are suitably methyl groups; $R_5$ and $R_8$ are suitably methoxy-substituted phenyl groups; and $R_3$, $R_4$, $R_9$, and $R_{10}$ are suitably independently hydroxyl, hydrogen, or methyl groups.

Suitable manassantin compounds according to the present invention include, but are not limited to, those shown below:

33

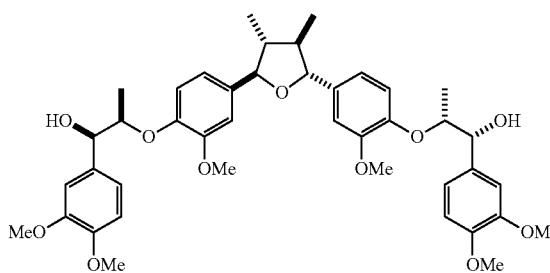

22

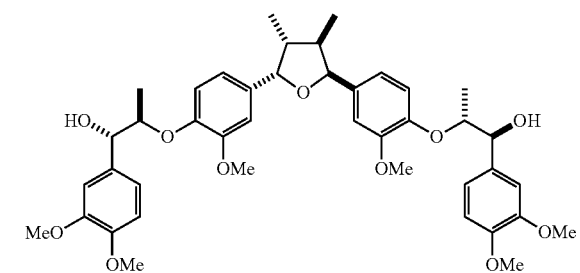

18

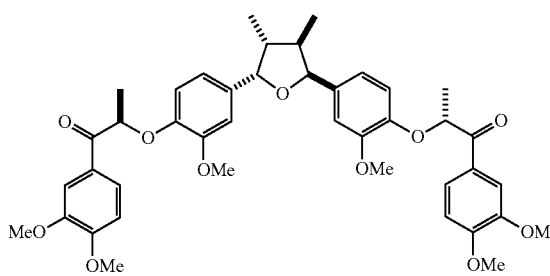

40

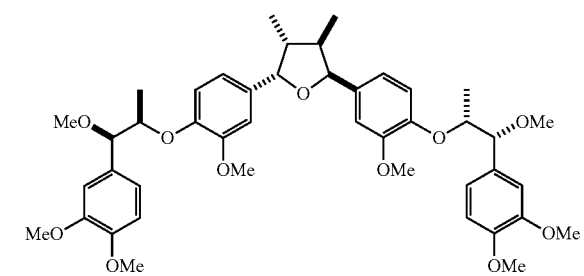

41

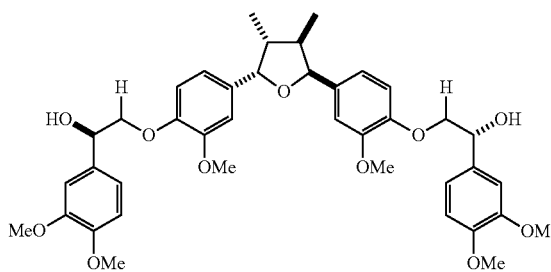

42

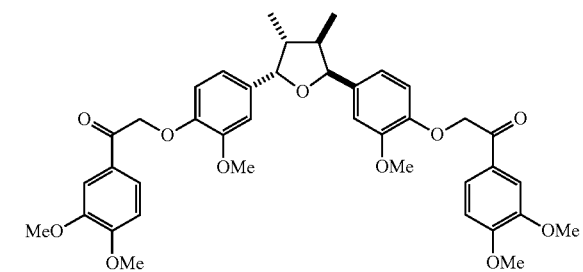

-continued
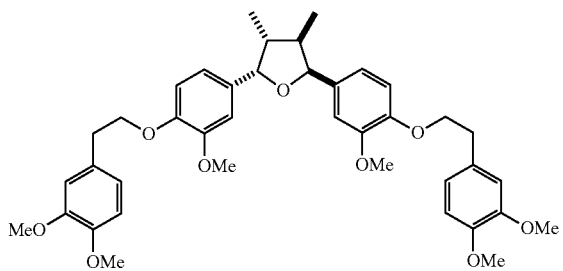
43
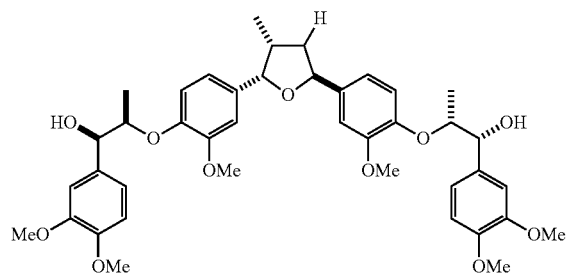
44
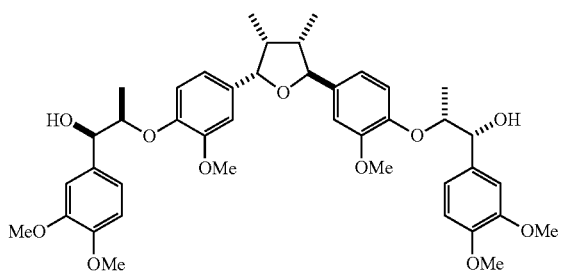
45
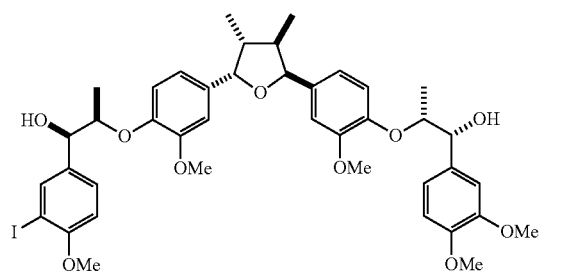
46
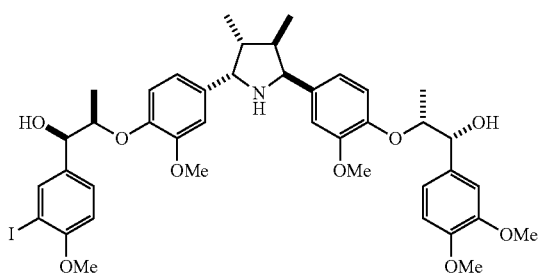
89
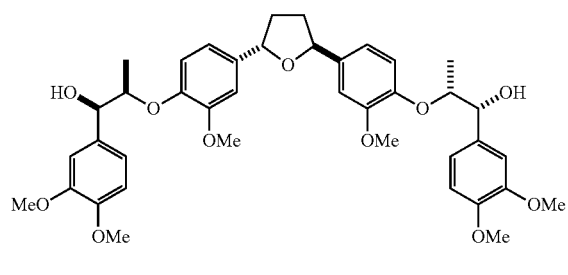
102
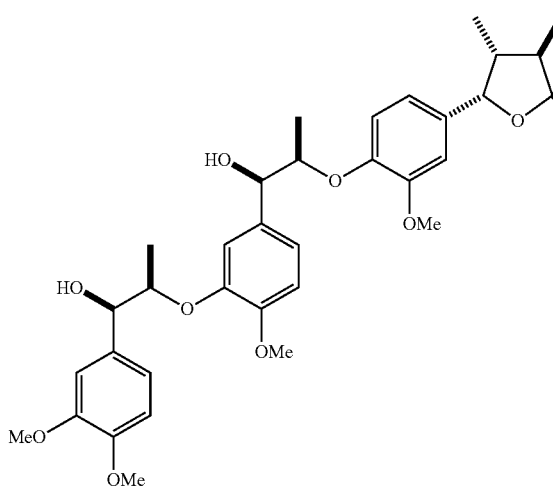
110
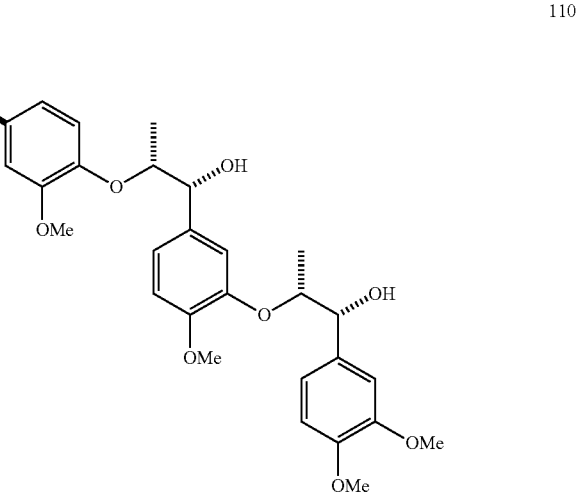

117

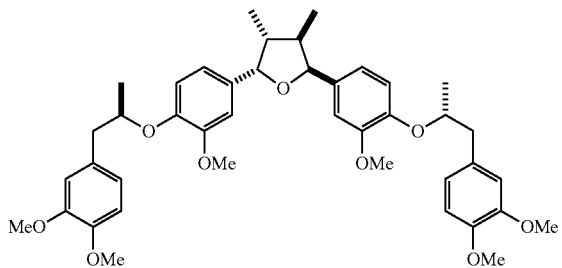

120

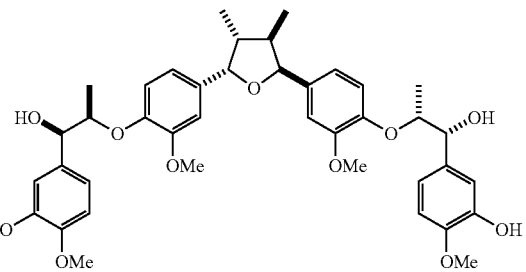

In certain embodiments, compounds of the invention do not include the following compound:

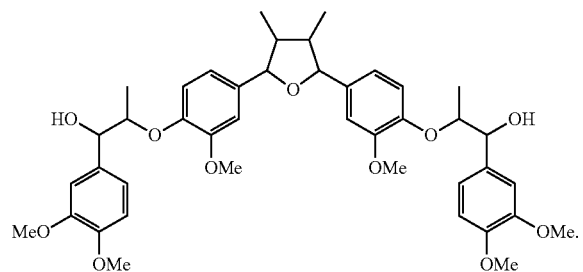 [SMILES: COc1ccc(C(O)C(C)Oc2ccc(C3OC(c4ccc(OC(C)C(O)c5ccc(OC)c(OC)c5)c(OC)c4)C(C)C3C)cc2OC)cc1OC]

In certain embodiments, compounds of the invention do not include the compounds of manassantin A (1) and manassantin B (2) shown below:

1

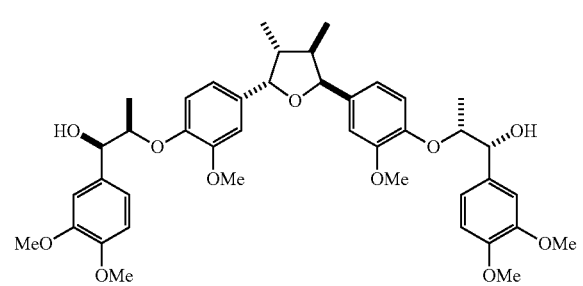

2

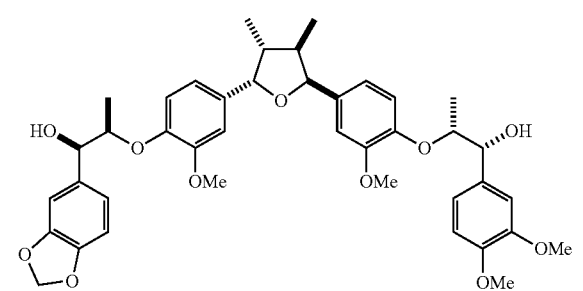

Stereoselective Synthesis of Manassantin Compounds

It has surprisingly been discovered that the disadvantages of the difficult procedures used to chemically synthesize manassantin A and manassantin B can be overcome through nucleophilic addition of organozinc reagents to 2-benzenesulfonyl cyclic ethers to achieve the 2,3-cis-3,4-trans-4,5-cis-tetrahydrofuran moiety, followed by addition of side arms via $S_N2$ reactions.

Figure 1:
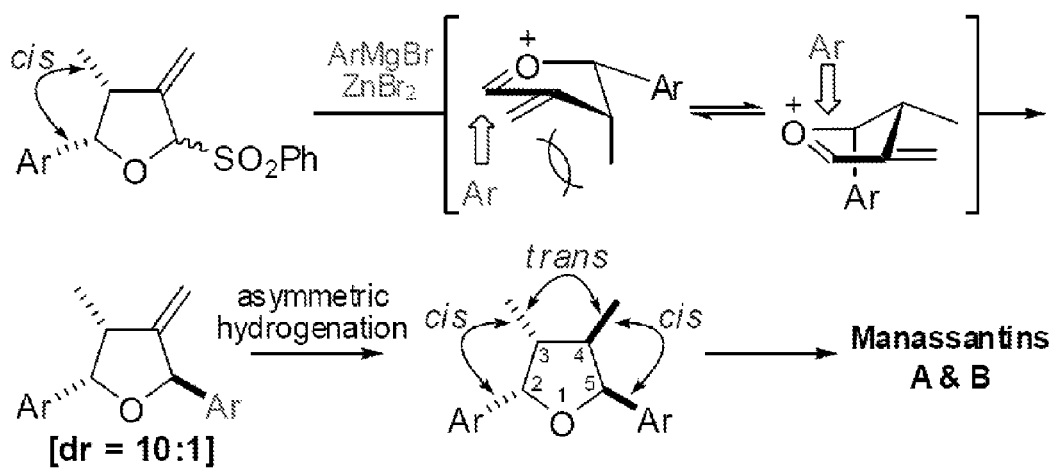
FIG. 1 is a general scheme for the chemical synthesis of manassantin compounds according to the invention.
Figure 2:
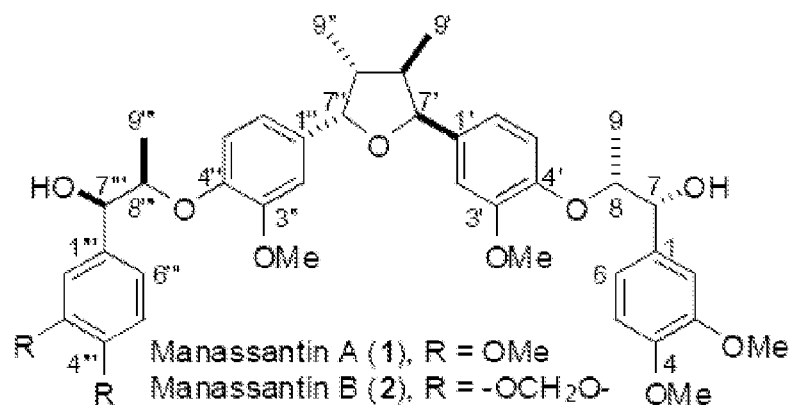
FIG. 2 is a scheme for the retrosynthetic chemical synthesis of manassantin compounds according to the invention.
Figure 2:
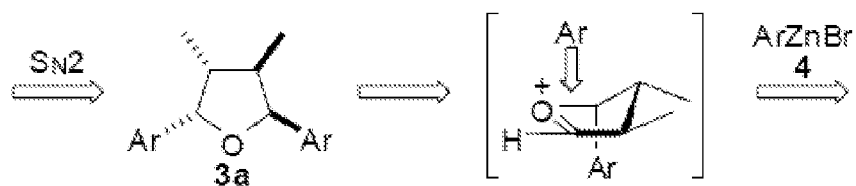
Figure 2:
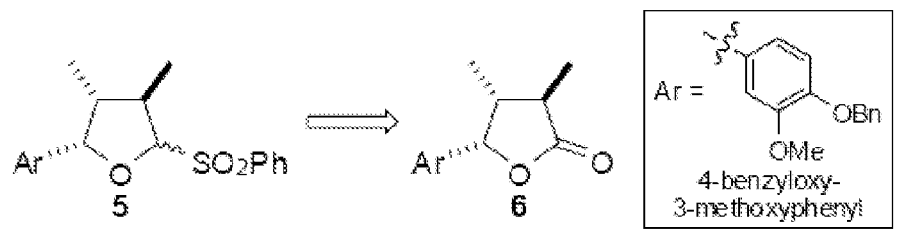
Figure 2:
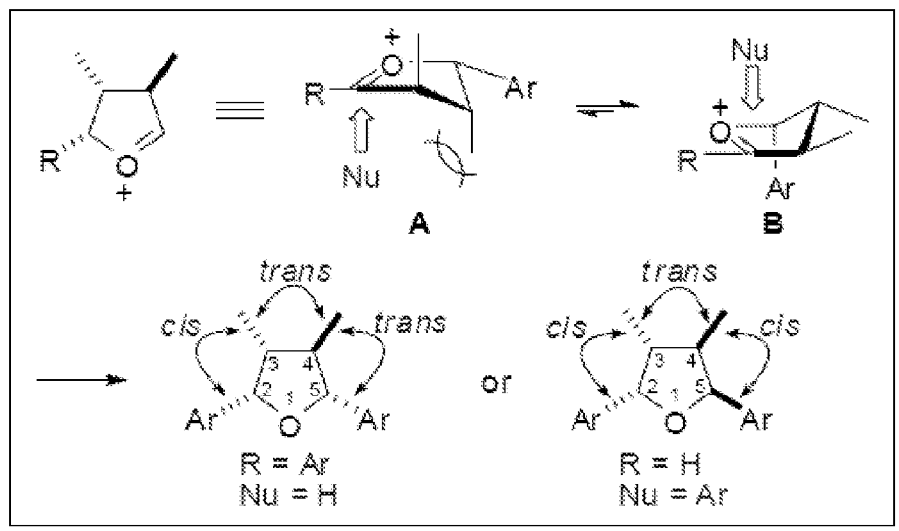

The general process for stereoselective synthesis of manassantin compounds according to the present invention is depicted in FIG. 1, and a retrosynthetic pathway is depicted in FIG. 2. The central five-membered heterocyclic ring may be synthesized first. The 2,3-cis-3,4-trans-4,5-trans-tetrahydrofuran or 2,3-trans-3,4-trans-4,5-trans-tetrahydrofuran may be stereoselectively synthesized via $BF_3.OEt_2$-promoted reductive deoxygenation of cyclic hemiketals (Kim, H.; Wooten, C. M.; Park, Y.; Hong, J. Org. Lett. 2007, 9, 3965-3968, which is incorporated by reference). The resulting stereochemistry outcome may be rationalized based on Woerpel's "inside attack" model. Based on the same rationale, an organozinc reagent such as ArZnBr may be added to the sterically more favorable conformation of the 2-benzenesulfonyl cyclic ether from the inside face of the envelope conformer to stereoselectively provide the 2,3-cis-3,4-trans-4,5-cis-tetrahydrofuran.

Figure 3:
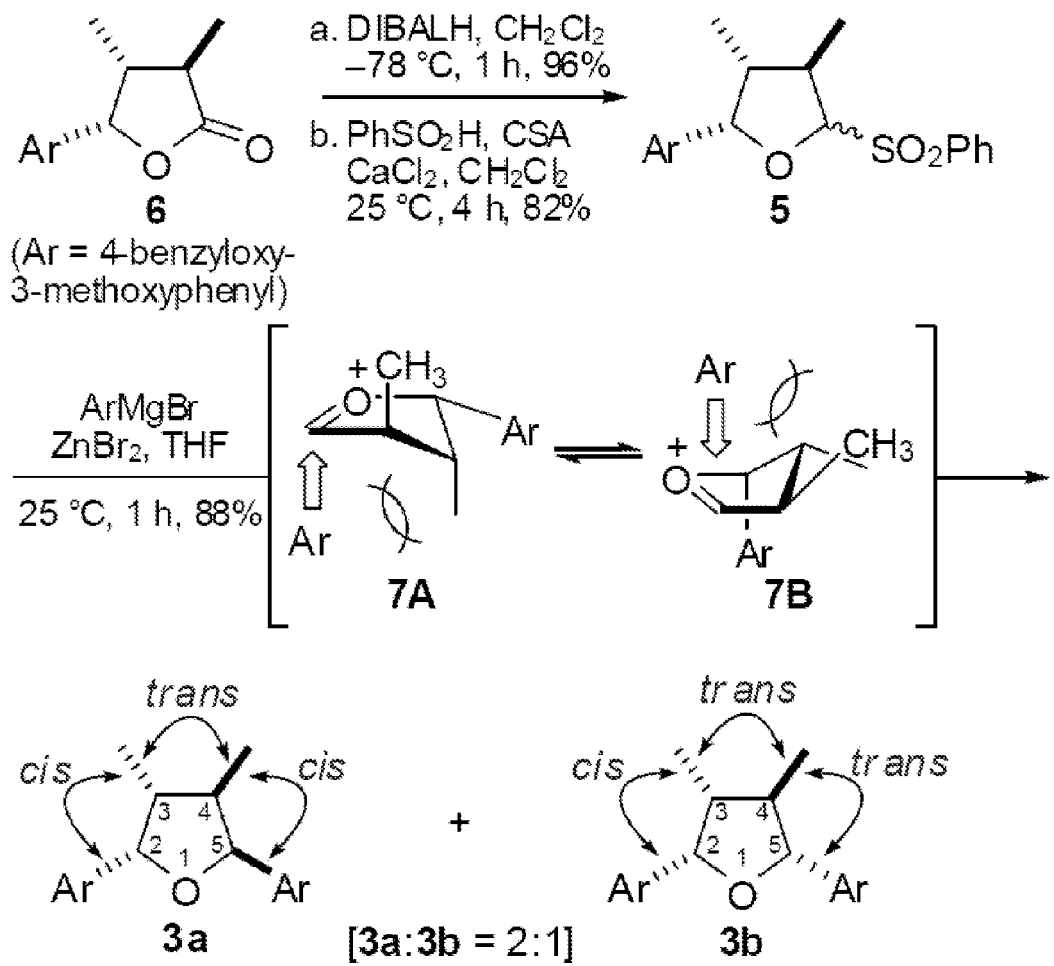
FIG. 3 is a scheme for the chemical synthesis of 2,3-cis-3,4-trans-4,5-cis-tetrahydrofuran and 2,3-cis-3,4-trans-4,5-trans-tetrahydrofuran diastereomers in a ratio of 2:1.

As shown in FIG. 3 and detailed in Example 1, reduction of 6 (Kim, H.; Wooten, C. M.; Park, Y.; Hong, J. Org. Lett. 2007, 9, 3965-3968, which is incorporated by reference) with DIBALH followed by treatment with $PhSO_2H$ and camphorsulfonic acid may be used to provide the 2-benzenesulfonyl cyclic ether 5 (Brown, D. S.; Ley, S. V. Tetrahedron Lett. 1988, 29, 4869-4872; Brown, D. S.; Bruno, M.; Davenport, R. J.; Ley, S. V. Tetrahedron 1989, 45, 4293-4308, both of which are incorporated by reference). The key nucleophilic substitution reaction of 5 with (4-benzyloxy-3-methoxyphenyl)zinc(II) bromide 4, derived in situ from (4-benzyloxy-3-methoxyphenyl)magnesium bromide and $ZnBr_2$ (Brown, D. S.; Ley, S. V. Tetrahedron Lett. 1988, 29, 4869-4872; Brown, D. S.; Bruno, M.; Davenport, R. J.; Ley, S. V. Tetrahedron 1989, 45, 4293-4308, both of which are incorporated by reference) may provide a 2:1 diastereomeric mixture of 2,5-diaryl-3,4-dimethyl tetrahydrofurans. Careful analysis of $^1H$ NMR spectral data revealed that the major diastereomer has the 2,3-cis-3,4-trans-4,5-cis-configuration (3a) and the minor diastereomer has the 2,3-cis-3,4-trans-4,5-trans-configuration (3b).

Figure 4:
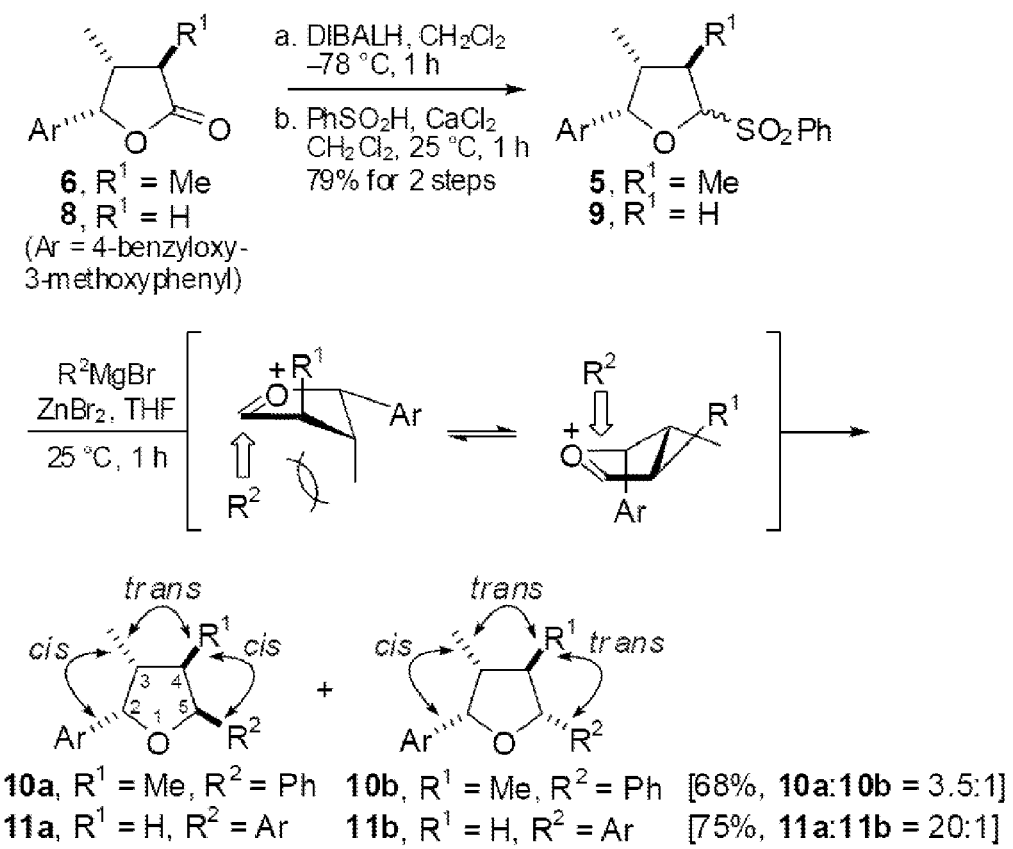
FIG. 4 is a scheme for the chemical synthesis of tetrahydrofuran diastereomers using different nucleophiles.

To improve the disastereoselectivity, model systems may be used where the postulated repulsive interaction (between the incoming nucleophile and the C-4 methyl group during addition of 4 to the oxocarbenium intermediate) is reduced by addition of a smaller nucleophile or removal of the C-4 methyl group (FIG. 4). Addition of a sterically less demanding PhZnBr to 5 may yield a 3.5:1 diastereomeric mixture of 10a and 10b. In addition, 4 may be added to the cyclic ether 9 for the reaction to proceed with excellent distereoselectivity (dr=20:1).

Figure 5:
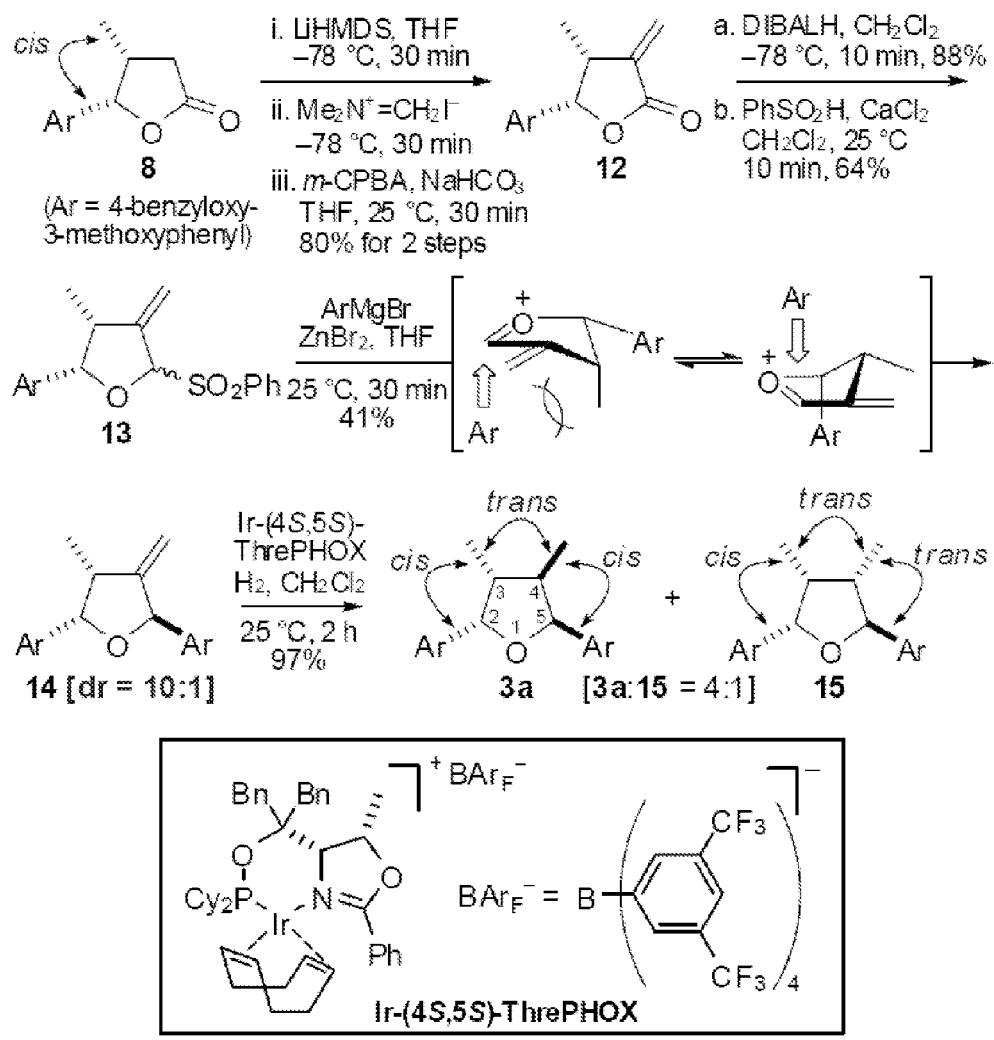
FIG. 5 is a scheme for the chemical synthesis of 2,3-cis-3,4-trans-4,5-cis-tetrahydrofuran diastereomer.

To further improve the stereoselectivity of the reaction and of 3a, a sterically less demanding exo-methylene group as a precursor to the C-4 methyl group and stereoselective reduction of the double bond may be used. As shown in FIG. 5, alkylation of 8 with Eschenmoser's salt and m-CPBA oxidation may generate 12 (80% for 2 steps) (Schreiber, J.; Maag, H.; Hashimoto, N.; Eschenmoser, A. *Angew. Chem., Int. Ed. Engl.* 1971, 10, 330-331; Mandal, M.; Yun, H.; Dudley, G. B.; Lin, S.; Tan, D. S.; Danishefsky, S. J. *J. Org. Chem.* 2005, 70, 10619-10637, both of which are incorporated by reference). Reduction of 12 with DIBALH followed by treatment with $PhSO_2H$ may provide 13 in good (64%) yield. The exomethylene group in 13 may direct the addition of 4 via "inside attack" model to provide the desired 2,3-cis-2,5-trans-tetrahydrofuran 14 as a major diastereomer (dr=10:1). However, catalytic hydrogenation under conventional conditions (e.g. Pd/C, $PtO_2$) or diimide reduction of 14 may yield the desired 2,3-cis-3,4-trans-4,5-cis-tetrahydrofuran as a minor diastereomer (dr=1:1-1:4). It was surprisingly found that asymmetric hydrogenation of 14 in the presence of Ir and (4S,5S)-ThrePHOX (McIntyre, S.; Hoermann E.; Menges, F.; Smidt, P.; Pfaltz A. *Adv. Synth. Catal.* 2005, 347, 282-288, which is incorporated by reference) provides 3a in 97% yield (dr=4:1) (asymmetric hydrogenation of 14 in the presence of Ir and (4R,5R)-ThrePHOX provided 3a as a minor diastereomer (dr=1:2)).

Figure 6:
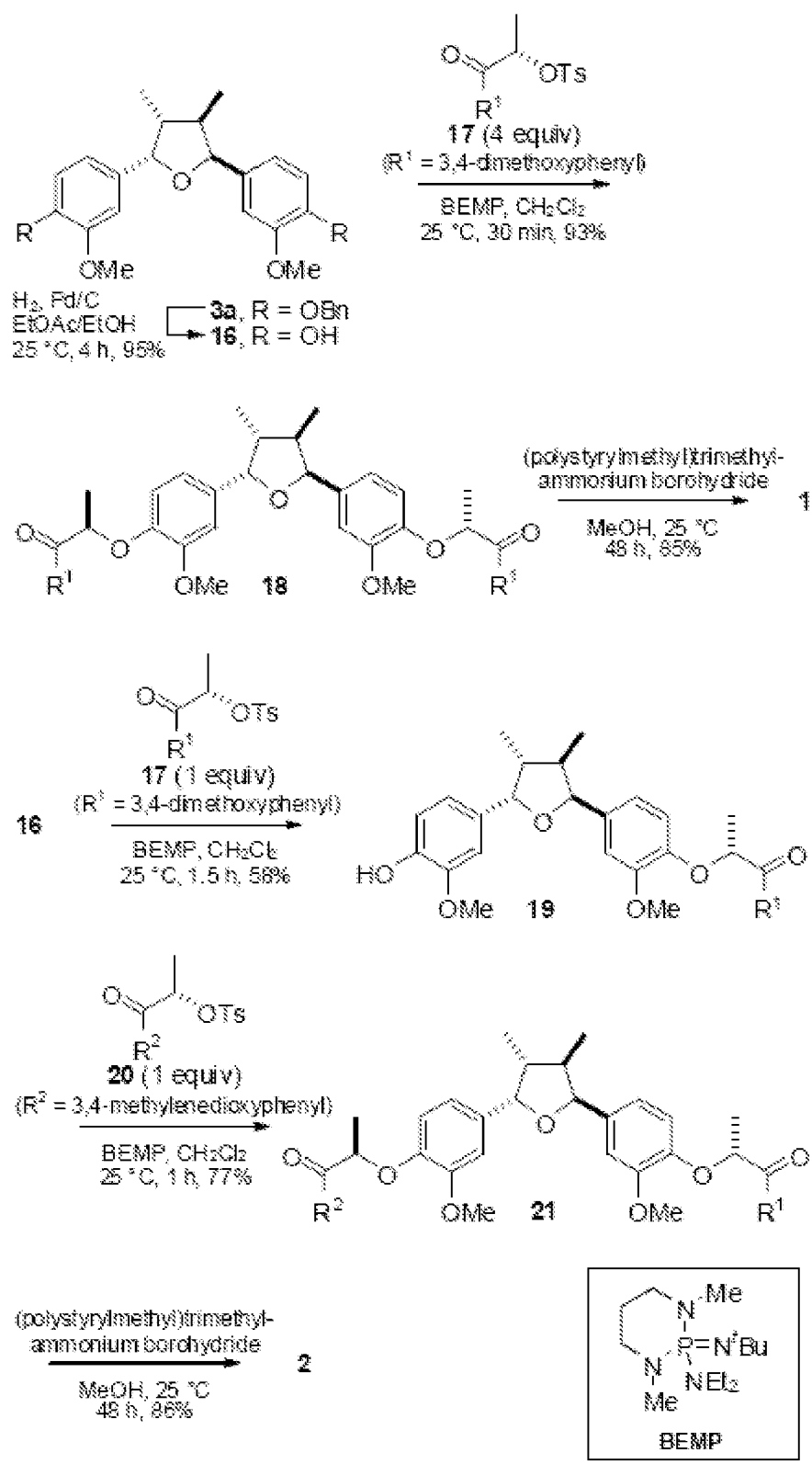
FIG. 6 is a scheme for the chemical synthesis of manassantin compounds from the 2,3-cis-3,4-trans-4,5-cis-tetrahydrofuran diastereomer.

This core tetrahydrofuran unit, 2,3-cis-3,4-trans-4,5-cis-tetrahydrofuran, may be coupled to the appropriate side arms via $S_N2$ reactions to complete the synthesis of manassantin A and manassantin B. As shown in FIG. 6 and detailed in Example 3, a BEMP-mediated $S_N2$ reaction of 16 and 17 (following the procedures reported in Lee, A.-L.; Ley, S. V. *Org. Biomol. Chem.* 2003, 1, 3957-3966, which is incorporated by reference, 17 and 20 were prepared from 1,2-dimethyl-4-(2-propen-1-yl)benzene and 5-(2-propen-1-yl)-1,3-benzodioxole, respectively) followed by stereocontrolled-reduction using polymer-supported $BH_4$ may be used to complete the synthesis of manassantin A. In order to accomplish the synthesis of 2, 16 may be subjected to the BEMP-mediated $S_N2$ reaction with 1 equivalent of 17 to form the mono-alkylation product 19 (58% BRSM) in addition to 18 (42% BRSM). Compound 19 may be then subjected to a second BEMP-mediated $S_N2$ reaction with 20 (following the procedures reported in Lee, A.-L.; Ley, S. V. *Org. Biomol. Chem.* 2003, 1, 3957-3966, which is incorporated by reference, 17 and 20 were prepared from 1,2-dimethyl-4-(2-propen-1-yl)benzene and 5-(2-propen-1-yl)-1,3-benzodioxole, respectively) to give 21 (77%). Reduction of 21 with polymer-supported $BH_4$ may be used to generate manassantin B.

Derivatives of Stereospecific Manassantin Compounds

The manassantin compounds can be converted into other analogs in various ways. In one embodiment, the 2,3-cis-3,4-trans-4,5-trans-tetrahydrofuran and 2,3-trans-3,4-trans-4,5-trans-tetrahydran can be prepared as follows. Treatment of 10 with 4-tert-butyldimethylsilyloxy-3-methoxyphenyllithium may give a anomeric mixture of the cyclic hemiketal. Treatment of the cyclic hemiketal with $Et_3SiH$ in the presence of $BF_3.OEt_2$ may preferentially provide the desired 2,3-cis-3,4-trans-4,5-trans-tetrahydrofuran through the addition of hydride from the inside face of the envelope conformer. If the cyclic hemiketal is treated with $BF_3.OEt_2$ (−78 to −20° C.) followed by reduction with $NaBH_3CN$, it may provide the 2,3-trans-3,4-trans-4,5-trans-tetrahydrofuran.

This core tetrahydrofuran units, the 2,3-cis-3,4-trans-4,5-trans-tetrahydrofuran and 2,3-trans-3,4-trans-4,5-trans-tetrahydran, may be coupled to the appropriate side arms via $S_N2$ reactions to complete the synthesis of other manassantin analogues.

Methods of Assessing Effectiveness for Treatment

In other embodiments, the invention provides methods of assessing the effectiveness of a compound for treatment of a disease or disorder. The methods may comprise contacting a cell with a compound according to Formula I, determining the proliferation of the cell, and comparing the proliferation to a control, wherein the reduction in proliferation is indicative of the effectiveness of the compound to treat the disease or disorder.

Methods of Treatments Using Manassantin Compounds

Manassantin compounds may be useful in inhibiting the activity of HIF-1 or down regulating HIF-1. The manassantin compounds of the present invention may be used to treat various conditions, disorders or diseases such as cancer, stroke, heart disease, arthritis, ocular neovascular diseases, inflammation, kidney disease, tissue ischemia, and anemia. Cancers include but are not limited to leukemia, lung cancer, colon cancer, CNS cancer, melanoma, ovarian cancer, renal cancer, liver cancer, prostate cancer, and breast cancer.

In one embodiment, a cell is contacted with an amount of a manassantin compound effective to inhibit HIF-1 pathway.

An effective amount of a manassantin compound according to the present invention will vary with the particular condition being treated, the age and physical condition of the patient being treated, the severity of the condition, the duration of treatment, the nature of concurrent therapy, the route of administration, the particular pharmaceutically-acceptable carrier utilized, and like factors within the knowledge and expertise of the attending physician. For example, an effective amount of the manassantin compounds of the present invention for systemic administration may be from about 6 to about 100 mg/kg body weight. Transdermal dosages may be designed to attain similar serum or plasma levels, based upon techniques known to those skilled in the art of pharmacokinetics and transdermal formulations. While these dosages are based upon a daily administration rate, the manassantin compounds of the present invention may also be administered at other intervals, such as twice per day, twice weekly, once weekly, or once a month. One of ordinary skill in the art would be able to calculate suitable effective amounts for other intervals of administration.

Compositions Comprising Manassantin Compounds

In one embodiment, the manassantin compounds may be administered in a pharmaceutically acceptable composition, such as in or with a pharmaceutically acceptable carrier.

Compositions may include one or more of the isoforms of the manassantin compounds of the present invention. When racemates exists, each enantiomer or diastereomer may be separately used, or they may be combined in any proportion. Where tautomers exist, all possible tautomers are specifically contemplated.

Pharmaceutical compositions for use in accordance with the present invention may be formulated in a conventional manner using one or more physiologically acceptable carriers or excipients. Thus, the manassantin compounds may be formulated for administration by, for example, solid dosing, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.).

The route by which the manassantin compounds of the present invention (component A) will be administered and the form of the composition will dictate the type of carrier (component B) to be used. The composition may be in a variety of forms, suitable, for example, for systemic administration (e.g., oral, rectal, nasal, sublingual, buccal, implants, or parenteral) or topical administration (e.g., local application on the skin, liposome delivery systems, or iontophoresis).

Carriers for systemic administration typically comprise at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others. All carriers are optional in the systemic compositions.

Ingredient a) is a diluent. Suitable diluents for solid dosage forms include sugars such as glucose, lactose, dextrose, and sucrose; diols such as propylene glycol; calcium carbonate; sodium carbonate; sugar alcohols, such as glycerin; mannitol; and sorbitol. The amount of ingredient a) in the systemic or topical composition is typically about 50 to about 90%.

Ingredient b) is a lubricant. Suitable lubricants for solid dosage forms are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of ingredient b) in the systemic or topical composition is typically about 5 to about 10%.

Ingredient c) is a binder. Suitable binders for solid dosage forms include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%, and in ocular solid dosing forms up to 99%.

Ingredient d) is a disintegrant. Suitable disintegrants for solid dosage forms include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic or topical composition is typically about 0.1 to about 10%.

Ingredient e) for solid dosage forms is a colorant such as an FD&C dye. When used, the amount of ingredient e) in the systemic or topical composition is typically about 0.005 to about 0.1%.

Ingredient f) for solid dosage forms is a flavor such as menthol, peppermint, and fruit flavors. The amount of ingredient f), when used, in the systemic or topical composition is typically about 0.1 to about 1.0%.

Ingredient g) for solid dosage forms is a sweetener such as aspartame and saccharin. The amount of ingredient g) in the systemic or topical composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic or topical composition is typically about 0.1 to about 5%.

Ingredient j) is a preservative such as benzalkonium chloride, methyl paraben and sodium benzoate. The amount of ingredient j) in the systemic or topical composition is typically about 0.01 to about 5%.

Ingredient k) for solid dosage forms is a glidant such as silicon dioxide. The amount of ingredient k) in the systemic or topical composition is typically about 1 to about 5%.

Ingredient m) is a solvent, such as water, isotonic saline, ethyl oleate, glycerine, hydroxylated castor oils, alcohols such as ethanol, and phosphate buffer solutions. The amount of ingredient m) in the systemic or topical composition is typically from about 0 to about 100%.

Ingredient n) is a suspending agent. Suitable suspending agents include Avicel® RC-591 (from FMC Corporation of Philadelphia, Pa.) and sodium alginate. The amount of ingredient n) in the systemic or topical composition is typically about 1 to about 8%.

Ingredient o) is a surfactant such as lecithin, Polysorbate 80, and sodium lauryl sulfate, and the TWEENS® from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of ingredient o) in the systemic or topical composition is typically about 0.1% to about 5%.

Although the amounts of components A and B in the systemic compositions will vary depending on the type of systemic composition prepared, the specific derivative selected for component A and the ingredients of component B, in general, system compositions comprise 0.01% to 50% of component A and 50 to 99.99% of component B.

Compositions for parenteral administration typically comprise A) 0.1 to 10% of the compounds of the present invention and B) 90 to 99.9% of a carrier comprising a) a diluent and m) a solvent. In one embodiment, component a) comprises propylene glycol and m) comprises ethanol or ethyl oleate.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A). The oral dosage compositions further comprise about 50 to about 95% of component B), and more particularly, from about 50 to about 75%.

Tablets can be compressed, tablet triturates, enteric-coated, sugar-coated, film-coated, or multiple-compressed. Tablets typically comprise component A, and component B a carrier comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Capsules (including implants, time release and sustained release formulations) typically comprise component A, and a carrier comprising one or more a) diluents disclosed above in a capsule comprising gelatin. Granules typically comprise component A, and preferably further comprise k) glidants such as silicon dioxide to improve flow characteristics. Implants can be of the biodegradable or the non-biodegradable type. Implants may be prepared using any known biocompatible formulation.

The selection of ingredients in the carrier for oral compositions depends on secondary considerations like taste, cost, and shelf stability, which are not critical for the purposes of this invention. One skilled in the art would know how to select appropriate ingredients without undue experimentation.

The solid compositions may also be coated by conventional methods, typically with pH or time-dependent coatings, such that component A is released in the gastrointestinal tract in the vicinity of the desired application, or at various points and times to extend the desired action. The coatings typically comprise one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G.M.B.H. of Darmstadt, Germany), waxes, and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise component A and component B, namely, a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the manassantin compounds include sublingual, buccal, and nasal dosage forms. Such compositions typically comprise one or more of soluble filler substances such as a) diluents including sucrose, sorbitol, and mannitol; and c) binders such as acacia, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants.

In one embodiment of the invention, the manassantin compounds of the present invention are topically administered. Topical compositions that can be applied locally may be in any form known in the art, non-limiting examples of which include solids, gelable drops, sprays, or ointments.

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, the manassantin compounds described above, and component B, a carrier. Component B may further comprise one or more optional components.

The exact amounts of each component in the topical composition depend on various factors. The amount of component A added to the topical composition is dependent on the $IC_{50}$ of component A, typically expressed in nanomolar (nM) units. For example, if the $IC_{50}$ of the medicament is 1 nM, the amount of component A will be from about 0.001 to about 0.3%. If the $IC_{50}$ of the medicament is 10 nM, the amount of component A) will be from about 0.01 to about 1%. If the $IC_{50}$ of the medicament is 100 nM, the amount of component A will be from about 0.1 to about 10%. If the $IC_{50}$ of the medicament is 1000 nM, the amount of component A will be 1 to 100%, preferably 5% to 50%. If the amount of component A is outside the ranges specified above (i.e., lower), efficacy of the treatment may be reduced. One skilled in the art understands how to calculate and understand an $IC_{50}$. The remainder of the composition, up to 100%, is component B.

The amount of the carrier employed in conjunction with component A is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

Component B may comprise a single ingredient or a combination of two or more ingredients. In the topical compositions, component B comprises a topical carrier. Suitable topical carriers comprise one or more ingredients selected from the group consisting of phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of the topical composition may further comprise one or more ingredients selected from the group consisting of q) emollients, r) propellants, s) solvents, t) humectants, u) thickeners, v) powders, w) fragrances, x) pigments, and y) preservatives.

Ingredient q) is an emollient. The amount of ingredient q) in a skin-based topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0 to about 95%. Suitable propellants include propane, butane, isobutane, dimethyl ether, carbon dioxide, nitrous oxide, and combinations thereof.

Ingredient s) is a solvent. The amount of ingredient s) in the topical composition is typically about 0 to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include water, ethyl alcohol and propylene glycol.

Ingredient t) is a humectant. The amount of ingredient t) in the topical composition is typically 0 to 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical composition is typically about 0 to about 95%.

Ingredient v) is a powder. The amount of ingredient v) in the topical composition is typically 0 to 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof.

Ingredient w) is a fragrance. The amount of ingredient w) in the topical composition is typically about 0 to about 0.5%, particularly, about 0.001 to about 0.1%.

Ingredient x) is a pigment. Suitable pigments for skin applications include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0 to about 10%.

Examples of z) cellulose derivatives suitable for use in the topical pharmaceutical composition for ocular administration include sodium carboxymethylcellulose, ethylcellulose, methylcellulose, and hydroxypropyl-methylcellulose, particularly, hydroxypropyl-methylcellulose.

Examples of aa) salts suitable for use in the topical pharmaceutical composition for ocular administration include mono-, di- and trisodium phosphate, sodium chloride, potassium chloride, and combinations thereof.

Examples of cc) pH adjusting additives include HCl or NaOH in amounts sufficient to adjust the pH of the topical pharmaceutical composition for ocular administration to 5.0-7.5.

Component A may be included in kits comprising component A, a systemic or topical composition described above, or both; and information, instructions, or both that use of the kit will provide treatment for cosmetic and medical conditions in mammals (particularly humans). The information and instructions may be in the form of words, pictures, or both, and the like. In addition or in the alternative, the kit may comprise the medicament, a composition, or both; and information, instructions, or both, regarding methods of application of medicament, or of composition, preferably with the benefit of treating or preventing cosmetic and medical conditions in mammals (e.g., humans).

EXAMPLES

The following non-limiting examples further illustrate the processes of the present invention:

Example 1

Chemical Synthesis of 2,3-cis-3,4-trans-4,5-trans-tetrahydrofuran and 2,3-trans-3,4-trans-4, 5-trans-tetrahydrofuran:

As shown in FIG. 3, the nucleophilic addition of (4-benzyloxy-3-methoxyphenyl)zinc(II) bromide to 2-benzenesulfonyl cyclic ether was completed. Compound 6 (Kim, H.; Wooten, C. M.; Park, Y.; Hong, J. *Org. Lett.* 2007, 9, 3965-3968, which is incorporated by reference) was reduced with DIBALH and dichloromethane at −78° C. for 1 hour, followed by treatment with $PhSO_2H$, camphorsulfonic acid (CSA), dichloromethane, and $CaCl_2$ at 25° C. for 4 hours to provide the 2-benzenesulfonyl cyclic ether 5 (Brown, D. S.; Ley, S. V. *Tetrahedron Lett.* 1988, 29, 4869-4872; Brown, D. S.; Bruno, M.; Davenport, R. J.; Ley, S. V. *Tetrahedron* 1989, 45, 4293-4308, both of which are incorporated by reference). Specifically, to a cooled (−78° C.) solution of lactone 6 (298.7 mg, 0.915 mmol) in $CH_2Cl_2$ (5 mL, 0.183 M) was added dropwise DIBALH (1.10 mL, 1.0 M solution in toluene, 1.10 mmol). After being stirred at the same temperature for 1 h, the reaction was quenched with MeOH (0.5 mL). $H_2O$ (2 mL) and 2 N NaOH (2 mL) were added and the resulting mixture was stirred at 25° C. for 1 h. The layers were separated, and the aqueous layer was extracted with $CH_2Cl_2$ (2×10 mL). The combined organic layers were dried over anhydrous $Na_2SO_4$, and concentrated in vacuo. The residue was purified by column chromatography (silica gel, hexanes/EtOAc, 2/1) to afford lactol (287.1 mg, 96%) as a colorless oil. To a solution of stirred solution of the lactol (142.3 mg, 0.433 mmol) in $CH_2Cl_2$ (5 mL) was added $PhSO_2H$ (123.1 mg, 0.866 mmol), camphorsulfonic acid (catalytic amount), and $CaCl_2$ (140.0 mg) at 25° C. After being stirred at the same temperature for 4 h, the reaction mixture was quenched with saturated aqueous $NaHCO_3$ (5 mL) and diluted with EtOAc (10 mL). The layers were separated, and the aqueous layer was extracted with EtOAc (2×10 mL). The combined organic layers were washed with brine, and dried over anhydrous $Na_2SO_4$, and concentrated in vacuo. The residue was purified by column chromatography (silica gel, hexanes/EtOAc, 2/1) to afford a 3:1 diastereomeric mixture of sulfone 5 as a white foam (161.3 mg, 82%).

Compound 5 was then reacted with (4-benzyloxy-3-ethoxyphenyl)zinc(II) bromide 4 in the presence of $ZnBr_2$ and tetrahydrofuran (THF) at 25° C. for 1 hour. Specifically, to a solution of $ZnBr_2$ (1 mL, 0.26 M in THF) was added dropwise 4-benzyloxy-3-methoxyphenylmagnesium bromide (1.66 mL, 0.30 M in THF, 0.50 mmol) at 25° C. and the resulting mixture was stirred for 30 min before sulfone 5 (98.1 mg, 0.217 mmol) in THF (2 mL) was added dropwise. After being stirred for 1 h, the reaction mixture was cooled to 0° C., quenched with saturated aqueous $NH_4Cl$, and diluted with EtOAc. The layers were separated, and the aqueous layer was extracted with EtOAc (2×10 mL). The combined organic layers were washed with brine, dried over anhydrous $Na_2SO_4$, and concentrated in vacuo. The residue was purified by column chromatography (silica gel, hexanes/EtOAc, 4/1). Unfortunately, the key nucleophilic substitution reaction of 5 with (4-benzyloxy-3-ethoxyphenyl)zinc(II) bromide 4, derived in situ from (4-benzyloxy-3-methoxyphenyl)magnesium bromide and $ZnBr_2$ (Brown, D. S.; Ley, S. V. *Tetrahedron Lett* 1988, 29, 4869-4872; Brown, D. S.; Bruno, M.; Davenport, R. J.; Ley, S. V. *Tetrahedron* 1989, 45, 4293-4308, both of which are incorporated by reference) provided a 2:1 diastereomeric mixture of 2,5-diaryl-3,4-dimethyl tetrahydrofurans. The 2:1 mixture of 2,3-cis-3,4-trans-4,5-cis-tetrahydrofuran 3a and 2,3-cis-3,4-trans-4,5-transtetrahydrofuran 3b was a colorless oil (102.1 mg, 88%), and was purified again by column chromatography (silica gel, hexanes/EtOAc, 7/1) to afford 2,3-cis-3,4-trans-4,5-cis-tetrahydrofuran 3a (59.2 mg, 52%) and 2,3-cis-3,4-trans-4,5-trans-tetrahydrofuran 3b (28.3 mg, 25%) and a mixture of 3a and 3b (12.0 mg, 11%). Careful analysis of $^1$H NMR spectral data revealed that the major diastereomer had the desired 2,3-cis-3,4-trans-4,5-cis-configuration (3a) and the minor diastereomer had the 2,3-cis-3,4-trans-4,5-trans-configuration (3b).

To improve the stereoselectivity, the steric repulsion during addition of 4 to the oxocarbenium intermediate via 7b between the incoming nucleophile and the C-4 methyl group were minimized. In this endeavor, two model systems were tested wherein the repulsive interaction was reduced by addition of a smaller nucleophile or removal of the C-4 methyl group (FIG. 4). In the first model system, 6 ($R^1$=Me) was reacted with DIBALH and dichloromethane at −78° C. for 1 hour, followed by treatment with PhSO$_2$H, camphorsulfonic acid (CSA), dichloromethane, and CaCl$_2$ at 25° C. in 1 hour for 2 steps to provide the compound 5 ($R^1$=Me).

Compound 5 was then reacted with PhMgBr and ZnBr$_2$ in THF for 1 hour at 25° C. to generate 10a ($R^1$=Me, $R^2$=Ph) and 10b ($R^1$=Me, $R^2$=Ph) in a ratio of 10a:10b=3.5:1 and a yield of 68%. Specifically, to a solution of ZnBr$_2$ (1 mL, 0.12 M in THF, 0.12 mmol) was added dropwise phenylmagnesium bromide (0.19 mL, 1.0 M in THF, 0.19 mmol) at 25° C. and the resulting mixture was stirred at the same temperature for 30 min before sulfone 5 (21.9 mg, 0.048 mmol) in THF (1 mL) was added dropwise. After being stirred for 1 h, the reaction mixture was cooled to 0° C., quenched with saturated aqueous NH$_4$Cl, and diluted with EtOAc. The layers were separated, and the aqueous layer was extracted with EtOAc (2×10 mL). The combined organic layers were washed with brine, dried over anhydrous Na$_2$SO$_4$, and concentrated in vacuo. The residue was purified by column chromatography (silica gel, hexanes/EtOAc, 4/1) to afford a 3.5:1 mixture of 2,3-cis-3,4-trans-4,5-cis-tetrahydrofuran 10a and 2,3-cis-3,4-trans-4,5-trans-tetrahydrofuran 10b as a colorless oil (12.7 mg, 68%).

In the second model system, 8 ($R^1$=H) was reacted with DIBALH and dichloromethane at −78° C. for 1 hour, followed by treatment with PhSO$_2$H, camphorsulfonic acid (CSA), dichloromethane, and CaCl$_2$ at 25° C. in 1 hour for 2 steps to provide the compound 9 ($R^1$=H). Specifically, to a cooled (−78° C.) solution of lactone 8 (272.5 mg, 0.872 mmol) in CH$_2$Cl$_2$ (10 mL, 0.087 M) was added dropwise DIBALH (1.02 mL, 1.0 M solution in toluene, 1.02 mmol). After being stirred at the same temperature for 1 h, the reaction was quenched with MeOH (0.5 mL). H$_2$O (2 mL) and 2 N NaOH (2 mL) was added and the resulting mixture was stirred at 25° C. for 1 h. The layers were separated, and the aqueous layer was extracted with CH$_2$Cl$_2$ (2×10 mL). The combined organic layers were dried over anhydrous Na$_2$SO$_4$, and concentrated in vacuo. This crude lactol was carried to the next step without further purification. HRMS (FAB) found 314.1517 [calculated for C$_{19}$H$_{22}$O$_4$ (M)$^+$ 314.1518]. To a solution of stirred solution of lactol in CH$_2$Cl$_2$ (2 mL) was added PhSO$_2$H (495.9 mg, 3.488 mmol) and CaCl$_2$ (193.5 mg, 1.74 mmol) at 25° C. After 1 h, the reaction was quenched with saturated aqueous NaHCO$_3$ (5 mL) and diluted with Et$_2$O (10 mL). The layers were separated, and the aqueous layer was extracted with EtOAc (2×10 mL). The combined organic layers were washed with brine, and dried over anhydrous Na$_2$SO$_4$, and concentrated in vacuo. The residue was purified by column chromatography (silica gel, hexanes/EtOAc, 2/1) to afford a 1:1 diastereomeric mixture of sulfone 9 as a white foam (302.5 mg, 79%).

Compound 9 was then reacted with ArMgBr (Ar is 4-benzyloxy-3-methoxyphenyl) and ZnBr$_2$ in THF for 1 hour at 25° C. to generate 11a ($R^1$=H, $R^2$=Ar) and 11b ($R^1$=H, $R^2$=Ar) in a ratio of 11a:11b=20:1 and a yield of 75%. Specifically, to a solution of ZnBr$_2$ (1 mL, 0.771 M in THF) was added dropwise 4-benzyloxy-3-methoxyphenylmagnesium bromide (4.28 mL, 0.3 M in THF, 1.28 mmol) at 25° C. and the resulting mixture was stirred at the same temperature for 30 min before sulfone 9 (112.9 mg, 0.257 mmol) in THF (2 mL) was added dropwise. After being stirred for 1 h, the reaction mixture was cooled to 0° C., quenched with saturated aqueous NH$_4$Cl, and diluted with EtOAc. The layers were separated, and the aqueous layer was extracted with EtOAc (2×10 mL). The combined organic layers were washed with brine, dried over anhydrous Na$_2$SO$_4$, and concentrated in vacuo. The residue was purified by column chromatography (silica gel, hexanes/EtOAc, 7/1) to afford 2,3-cis-2,5-trans-tetrahydrofuran 11a as a colorless oil (102.1 mg, 75%).

To provide 3a in good stereoselectivity and further improve the diastereoselectivity of the reaction, a sterically less demanding exo-methylene group as a precursor to the C-4 methyl group and stereoselective reduction of the double bond were introduced. As shown in FIG. 5, the compound 8 from the second model system described above was reacted with LiHMDS in THF for 30 min at −78° C., followed by reaction with Me$_2$N$^+$=CH$_2$I$^-$ for 30 min at −78° C., and then followed by reaction with m-CPBA and NaHCO$_3$ in THF for 30 min at 25° C. in two steps. This produced compound 12. Specifically, to a cooled (−78° C.) solution of lactone 8 (83.7 mg, 0.268 mmol) in THF (2 mL, 0.134 M) was added LiHMDS (0.536 mL, 1.0 M solution in THF, 0.536 mmol). The resulting mixture was stirred at the same temperature for 30 min and Eschenmoser's salt (148.7 mg, 0.804 mmol) in THF (1 mL) was added. After being stirred at the same temperature for another 15 min, the reaction mixture was quenched with saturated aqueous NH$_4$Cl solution, and diluted with CH$_2$Cl$_2$. The layers were separated, and the aqueous layer was extracted with (2×15 mL). The combined organic layers were dried over anhydrous Na$_2$SO$_4$, and concentrated in vacuo to afford the crude amine. This amine was carried to the next step without further purification. To a solution of the amine in THF (4 mL) and saturated aqueous NaHCO$_3$ (2 mL) was added m-CPBA (231.2 mg, max. 78%, 1.05 mmol) at 0° C. The resulting mixture was allowed to warm to 25° C. for 30 min, and quenched with saturated aqueous NaHCO$_3$ solution and saturated aqueous Na$_2$SO$_3$ solution. The layers were separated, and the aqueous layer was extracted with EtOAc (2×15 mL). The combined organic layer was washed with 2 N NaOH and brine, dried over anhydrous Na$_2$SO$_4$, and concentrated in vacuo. The residue was purified by column chromatography (silica gel, hexanes/EtOAc, 2/1) to afford lactone 12 as a colorless oil (69.2 mg, 80% for two steps).

Compound 12 was then reacted with DIBALH and dichloromethane at −78° C. for 10 min, followed by treatment with PhSO$_2$H, camphorsulfonic acid (CSA), dichloromethane, and CaCl$_2$ for 10 min at 25° C. to generate compound 13. Specifically, to a cooled (−78° C.) solution of lactone 12 (101.1 mg, 0.312 mmol) in CH$_2$Cl$_2$ (8 mL, 0.039 M) was added DIBALH (0.312 mL, 1.0 M solution in toluene, 0.312 mmol). After being stirred at the same temperature for 10 min, the reaction was quenched with MeOH. Then H$_2$O and 2 N NaOH was added and the resulting mixture was stirred at 25° C. for 1 h. The layers were separated, and the aqueous layer was extracted with $CH_2Cl_2$ (2×10 mL). The combined organic layers were dried over anhydrous $Na_2SO_4$, and concentrated in vacuo. The residue was purified by column chromatography (silica gel, hexanes/EtOAc, 2/1) to afford a mixture of lactol and aldehyde as a colorless oil (89.7 mg, 88%). To a stirred solution of a mixture of lactol and aldehyde (28.5 mg, 0.0873 mmol) in $CH_2Cl_2$ (3 mL, 0.029 M) were added $PhSO_2H$ (16.1 mg, 0.114 mmol) and $CaCl_2$ (29.1 mg, 0.262 mmol) at 25° C. After being stirred at the same temperature for 10 min, the reaction mixture was quenched with saturated aqueous $NaHCO_3$, and diluted with $Et_2O$ (15 mL). The layers were separated, and the aqueous layer was extracted with EtOAc (2×10 mL). The combined organic layers were washed with brine, dried over anhydrous $Na_2SO_4$, and concentrated in vacuo. The residue was purified by column chromatography (silica gel, hexanes/EtOAc/Et3N, 3/1/0.01) to afford sulfone 13 as a white foam (24.0 mg, 64%).

Compound 13 was then reacted with ArMgBr (Ar is 4-benzyloxy-3-methoxyphenyl) and $ZnBr_2$ in THF for 2 hours at 25° C. to generate compound 14 (the trans-tetrahydrofuran) as a major diastereomer (dr=10:1). Specifically, to a solution of $ZnBr_2$ (1 mL, 0.22 M in THF) was added dropwise 4-benzyloxy-3-methoxyphenylmagnesium bromide (2.78 mL, 0.16 M, 0.44 mmol) at 25° C. The resulting mixture was stirred at the same temperature for 30 min before sulfone 13 (40.0 mg, 0.088 mmol) in THF (1 mL) was added dropwise. After being stirred at 25° C. for 30 min, the reaction mixture was cooled to 0° C., quenched with saturated aqueous $NH_4Cl$, and diluted with EtOAc. The layers were separated, and the aqueous layer was extracted with EtOAc (2×10 mL). The combined organic layers were washed with brine, and dried over anhydrous $Na_2SO_4$, and concentrated in vacuo. The residue was purified by column chromatography (silica gel, hexanes/EtOAc, 6/1) to afford 2,3-cis-2,5-trans-tetrahydrofuran 14 as a colorless oil (19.1 mg, 41%).

Catalytic hydrogenation under conventional conditions (e.g. Pd/C, $PtO_2$) or diimide reduction of 14 only gave the desired 2,3-cis-3,4-trans-4,5-cis-tetrahydrofuran as a minor diastereomer (dr=1:1-1:4). However, it was found that asymmetric hydrogenation of 14 in the presence of Ir and (4S,5S)-ThrePHOX for 2 hours at 25° C. (McIntyre, S.; Hoermann E.; Menges, F.; Smidt, P.; Pfaltz A. *Adv. Synth. Catal.* 2005, 347, 282-288, which is incorporated by reference) provided 3a in 97% yield (dr=4:1) (Asymmetric hydrogenation of 14 in the presence of Ir and (4R,5R)-ThrePHOX provided 3a as a minor diastereomer (dr=1:2)). Specifcally, to a solution of 14 (107.1 mg, 0.205 mmol) in $CH_2Cl_2$ (5 mL) was added Ir-(4S, 5S)-ThrePHOX (3.5 mg, 0.002 mmol) at 25° C. under $H_2$ atmosphere, and the reaction mixture was stirred at the same temperature for 1 h. An addition of Ir-(4S,5S)-ThrePHOX (3.5 mg, 0.002 mmol) was repeated two times every 1 h, and the reaction mixture was stirred further for 10 h before concentrated in vacuo. The residue was filtrated through a pad of silica gel (hexanes/EtOAc, 3/1) to afford a 4:1 mixture of 2,3-cis-3,4-trans-4,5-cis-tetrahydrofuran 3a and 2,3-cis-3,4-cis-4,5-trans-tetrahydrofuran 15, which was purified by column chromatography (silica gel, hexanes/EtOAc, 10/1) to afford 2,3-cis-3,4-trans-4,5-cistetrahydrofuran 3a (66.3 mg, 62%), 2,3-cis-3,4-cis-4,5-trans-tetrahydrofuran 15 (19.9 mg, 18%), and a mixture of 3a and 15 (20.1 mg, 19%).

Example 2

Chemical Synthesis of Manassantin A and Analogues:

Manassantin A was generated by adding side chains to the desired tetrahydrofuran 3a described in Example 1. As shown in FIG. 6, a BEMP-mediated $S_N2$ reaction of 16 and 17 (following the procedures reported in Lee, A.-L.; Ley, S. V. *Org. Biomol. Chem.* 2003, 1, 3957-3966, which is incorporated by reference), 17 and 20 were prepared from 1,2-dimethyl-4-(2-propen-1-yl)benzene and 5-(2-propen-1-yl)-1,3-benzodioxole, respectively) followed by stereocontrolled-reduction using polymer-supported $BH_4$ completed the synthesis of manassantin A (1).

Compound 3a (with R═OBn) was reacted with Pd/C under hydrogen in EtOAc/EtOH for 4 hours at 25° C. to generate compound 16 (with R═OH). Specifically, to a stirred solution of bis-benzyl ether 3a (112 mg, 0.21 mmol) in EtOAc/EtOH (3:1, 4 mL) was added 10% palladium on activated carbon (22.4 mg, 20 wt %). The resulting mixture was stirred under $H_2$ atmosphere at 25° C. for 4 h. The reaction mixture was then filtered through celite with EtOAc and concentrated in vacuo. The residue was purified by column chromatography (silica gel, hexanes/EtOAc, 3/1) to afford bis-phenol 16 as a colorless oil (70 mg, 95%).

16 was reacted with 17 (with R═3,4-dimethoxyphenyl) in a BEMP-mediated $S_N2$ reaction in dichloromethane for 30 min at 25° C. to generate compound 18 and compound 19. Specifically, to a cooled (0° C.) solution of bis-phenol 16 (29.8 mg, 0.086 mmol) in dry $CH_2Cl_2$ (1.0 mL, 0.086 M) was added dropwise 2-tert-butylimino-2-diethylamino-1,3-dimethylpherhydro-1,3,2-diazaphosphorine (BEMP, 30 µL, 0.10 mmol). The resulting mixture was stirred at the same temperature for 10 min before 17 (126.0 mg, 0.346 mmol) in $CH_2Cl_2$ (1.0 mL) was added. The reaction mixture was allowed to warm to 25° C. for 30 min with stirring, quenched with saturated aqueous $NH_4Cl$ solution, and diluted with $CH_2Cl_2$ (2 mL). The layers were separated and the aqueous layer was extracted with $CH_2Cl_2$ (2×10 mL). The combined organic layers were washed with brine, dried over anhydrous $Na_2SO_4$, and concentrated in vacuo. The residue was purified by column chromatography (silica gel, hexanes/EtOAc, 2/1) to afford 18 as a colorless oil (64.4 mg, 93%).

Compound 18 was reacted with (polystyrylmethyl)trimethyl-ammonium borohydride in MeOH (polymer-supported $BH_4$) for 48 hours at 25° C. to generate manassantin A (1). Specifically, to a solution of bis-ketone 18 (14.0 mg, 0.019 mmol) in MeOH (0.5 mL) was added polymer supported borohydride (2.5-5.0 mmol $BH_4$/g resin, 132 mg, 0.33-0.66 mmol). The reaction mixture was stirred with gentle agitation at 25° C. for 48 h. The polymer beads were then removed by filtration and the filtrate was concentrated in vacuo to afford a 6:1 diastereomeric mixture of manassantin A (1) and (7S, 7'''S)-epimer, which was then purified by column chromatography (silica gel, hexanes/EtOAc/MeOH, 2/1/0.01) to afford 1 as a white solid (12.0 mg, 85%). For 19, to a cooled (0° C.) solution of 16 (20 mg, 0.058 mmol) in dry $CH_2Cl_2$ (0.5 mL) was added BEMP (16.8 µL, 0.058 mmol). The resulting mixture was stirred at 25° C. for 5 min before tosylate 17 (21 mg, 0.058 mmol) in $CH_2Cl_2$ (1 mL) was added. The reaction mixture was stirred at the same temperature for 1.5 h, quenched with saturated aqueous $NH_4Cl$ solution, and diluted with $CH_2Cl_2$ (2 mL). The layers were separated and the aqueous layer was extracted with $CH_2Cl_2$ (2×10 mL). The combined organic layers were washed with brine, dried over anhydrous $Na_2SO_4$, and concentrated in vacuo. The residue was purified via column chromatography, (silica gel, hexanes/EtOAc, 2/1) to afford 19 (9 mg, 29%) in addition to 16 (10 mg, 50%) and 18 (9 mg, 21%).

In summary, a direct nucleophilic addition of the organozinc reagent 4 was applied to the 2-benzenesulfonyl cyclic ether 5 followed by an asymmetric hydrogenation to synthesize the 2,3-cis-3,4-trans-4,5-cis-tetrahydrofuran moiety manassantin A and B. The stereoselectivity of the nucleophilic addition reaction was improved by introduction of the sterically less demanding exo-methylene group as a surrogate for the C-9' methyl group in manassantin A and B.

Example 3

Chemical Synthesis of Manassantin B:

Manassantin B (2) was generated as in Example 2 and FIG. 6 to first generate compound 18 and compound 19. Compound 19 was then subjected to a second BEMP-mediated $S_N2$ reaction in dichloromethane for 1 hour at 25° C. with compound 20 (with $R^2$=3,4-methylenedioxyphenyl) to give 21 (77%). Specifically, to a cooled (0° C.) solution of 19 (24.3 mg, 0.045 mmol) in $CH_2Cl_2$ (0.5 mL) was added dropwise BEMP (0.027 mL, 0.094 mmol). The resulting mixture was stirred at the same temperature for 10 min before tosylate 20 (15.7 mg, 0.045 mmol) was added. The reaction mixture was allowed to warm to 25° C. for 1 h with stirring, quenched with saturated aqueous $NH_4Cl$, and diluted with $CH_2Cl_2$. The layers were separated and the aqueous layer was extracted with $CH_2Cl_2$ (2×5 mL). The combined organic layers were washed with brine, dried over anhydrous $Na_2SO_4$, and concentrated in vacuo. The residue was purified by column chromatography, (silica gel, hexanes/EtOAc, 2/1) to afford 21 as a colorless oil (24.8 g, 77%).

Reduction of 21 with (polystyrylmethyl)trimethyl-ammonium borohydride in MeOH (polymer-supported $BH_4$) for 48 hours at 25° C. then afforded manassantin B (2). Specifically, to a stirred solution of 21 (24.8 mg, 0.035 mmol) in MeOH (1.5 mL) was added polymer-supported borohydride (2.5-5.0 mmol BH4/g resin, 400 mg, 1.0-2.0 mmol) and the reaction mixture was stirred with gentle agitation at 25° C. for 48 h. The polymer beads were then removed by filtration and the filtrate was concentrated in vacuo to afford a 5.4:1 diastereomeric mixture (21.4 mg, 86%) of manassantin B (2) and (7S,7'''S)-epimer, which was then purified by column chromatography (silica gel, hexanes/EtOAc/MeOH, 2/1/0.01) to afford manassantin B (2) as a white solid (13.3 mg, 53%) and a mixture (8.1 mg, 33%) of 2 and (7S,7'''S)-epimer.

Example 4

Chemical Synthesis of Compound 43:

To a cooled (0° C.) solution of bis-phenol 16 and 3,4-dimethoxyphenethylbromide in dry DMF, $K_2CO_3$ was added dropwise. The resulting mixture was stirred at 120° C. for 24 h, quenched with saturated aqueous $NH_4Cl$ solution, and diluted with EtOAc. The layers were separated and the aqueous layer was extracted with EtOAc. The combined organic layers were washed with brine, dried over anhydrous $Na_2SO_4$, and concentrated in vacuo. The residue was purified by column chromatography.

Example 5

The In Vitro HIF-1 Inhibitory Activity of Manassantin Compounds and Analogues:

The HIF-1 inhibitory of compound 1, 18, and the anti-diol diastereomer 22 were assessed with the ODD-Luc assay (Li, F.; Sonveaux, P.; Rabbani, Z. N.; Liu, S.; Yan, B.; Huang, Q.; Vujaskovic, Z.; Dewhirst, M. W.; Li, C. Y. Mol. Cell 2007, 26, 63-74, which is incorporated by reference). 4T1-ODD-Luc cells, stably transfected with the oxygen-dependent-degradation (ODD) domain of HIF-1α and a firefly luciferase reporter, were seeded in the 24-well plate at a density of $10^5$ cells/well. After 16-hour incubation, cells were treated with 240 μM of Cobalt (II) Chloride (Sigma-Aldrich, St. Louis, Mo., USA) and serially diluted compounds for 24 h. To measure the luciferase signals, luciferin (150 mg/mL) was added and the plates were imaged using the Xenogen IVIS imaging system and associated Living Image software (Xenogen, Alameda, Calif.). Luciferase expression/activity was detected and quantified as relative light units (RLUs). Results are means±SD, n=3.

Figure 7:
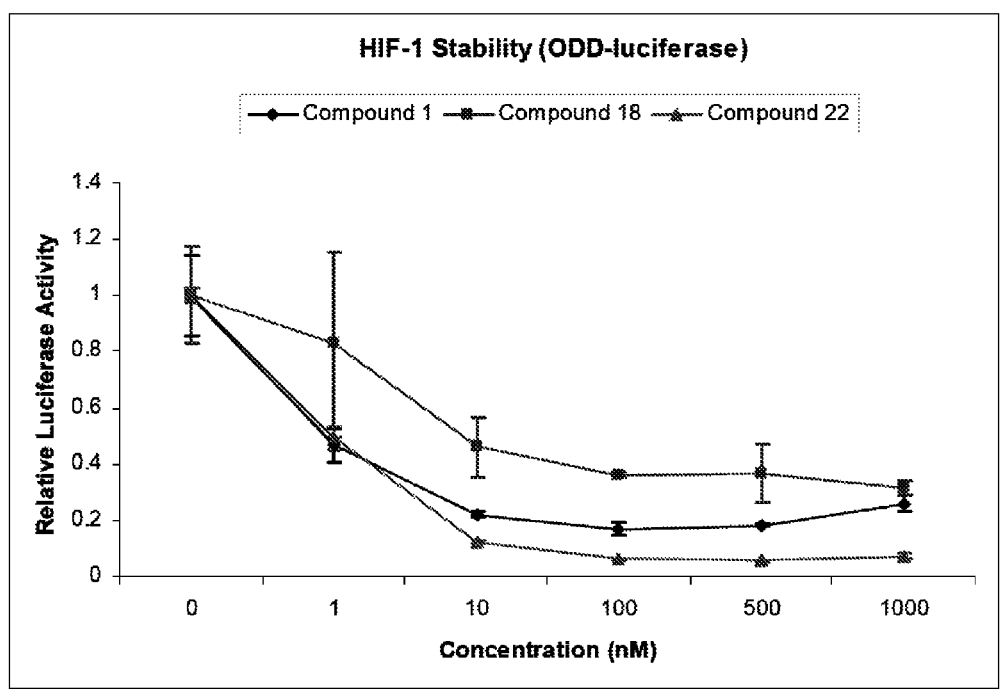
FIG. 7 is a graph of relative luciferase activity versus concentration of manassantin compound concentration, demonstrating the HIF-1 inhibitory activity of three manassantin compounds.

As shown in FIG. 7, all three compounds demonstrated similar HIF-1 inhibitory activity with an $IC_{50}$ of 1 to 10 nM. The data suggested that the (R)-configuration at bond a (C-7) and bond h (C-7''') is not critical for HIF-1 inhibition. In addition, the hydroxyl group at $R_3$ (C-7) and $R_{10}$ (C-7''') can be replaced with a carbonyl group without significant loss of activity.

Example 6

Figure 8:
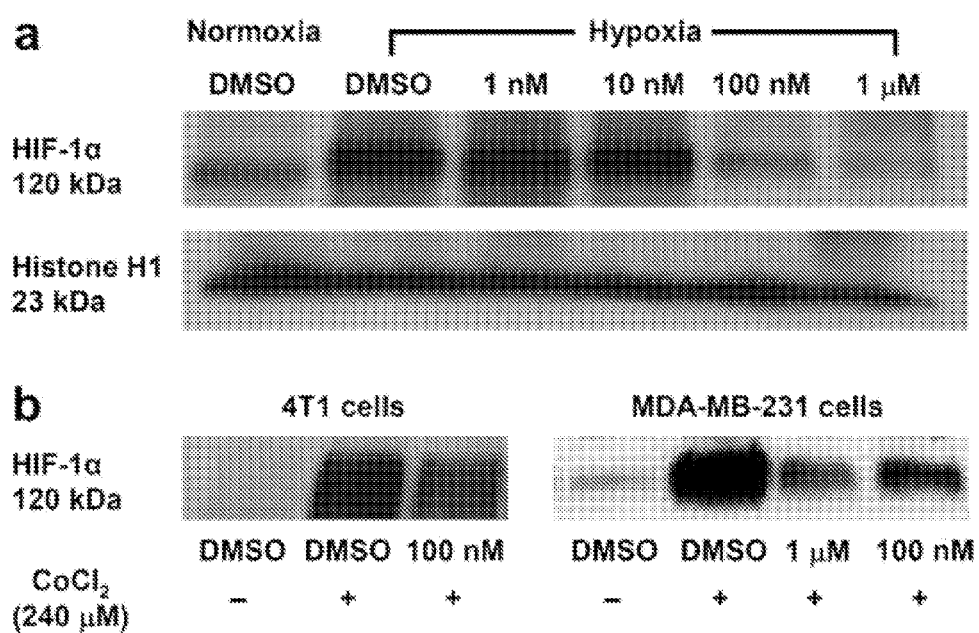
FIG. 8 are Western blots of 4T1 cells or MDA-MB-231 cells under hypoxia and treated with and without different amounts of manassantin A.

HIF-1 Inhibitory Activity of Manassantin A Using Western Blots:

Western blots were used to further confirm the HIF-1 inhibitory activity of manassantin A (1). 4T1 cells, a mouse mammary carcinoma, were grown under hypoxic conditions (0.5% $O_2$) for 24 h with various concentrations (0, 1, 10, 100 nM, and 1 μM) of manassantin A. Western blots were performed on nuclear extracts (Zhang, X.; Kon, T.; Wang, H.; Li, F.; Huang, Q.; Rabbani, Z. N.; Kirkpatrick, J. P.; Vujaskovic, Z.; Dewhirst, M. W.; Li, C. Y. Cancer Res. 2004, 64, 8139, which is incorporated by reference). A dose-response study revealed that exposure of 4T1 cells to manassantin A at concentrations higher than 10 nM for 24 h significantly inhibited hypoxia-induced nuclear expression of the HIF-1α protein (FIG. 8a). Histone H1 was used as a loading control.

To determine if manassantin A also inhibits chemically-induced HIF-1α expression (Wang, G. L.; Semenza, G. L. Blood 1993, 82, 3610, which is incorporated by reference), 4T1 cells were treated with 240 μM of $CoCl_2$ for 24 h and Western blots were carried out with nuclear extracts. HIF-1α expression induced by $CoCl_2$ was inhibited by manassantin A (100 nM) (FIG. 8b) indicating that manassantin A inhibits chemically induced HIF-1α expression as well as hypoxia-induced HIF-1α expression. It was previously reported that manassantin A had no significant effect on iron chelator-induced HIF-1 activation in T47D cells (10 μM 1,10-phenanthroline, 16 h) (Hossain, C. F.; Kim, Y.-P.; Baerson, S. R.; Zhang, L.; Bruick, R. K.; Mohammed, K. A.; Agarwal, A. K.; Nagle, D. G.; Zhou, Y.-D. Biochem. Biophys. Res. Commun. 2005, 333, 1026, incorporated by reference). To examine if the HIF-1 inhibition by manassantin A is cell-type specific, the same experiment was carried out with MDA-MB-231, a human breast cancer cell line. The same inhibition effect was observed, i.e., HIF-1α nuclear expression induced by $CoCl_2$ was inhibited by manassantin A, which showed that the HIF-1 inhibition effect by manassantin A is not cell-type specific (FIG. 8b).

Example 7

Figure 9:
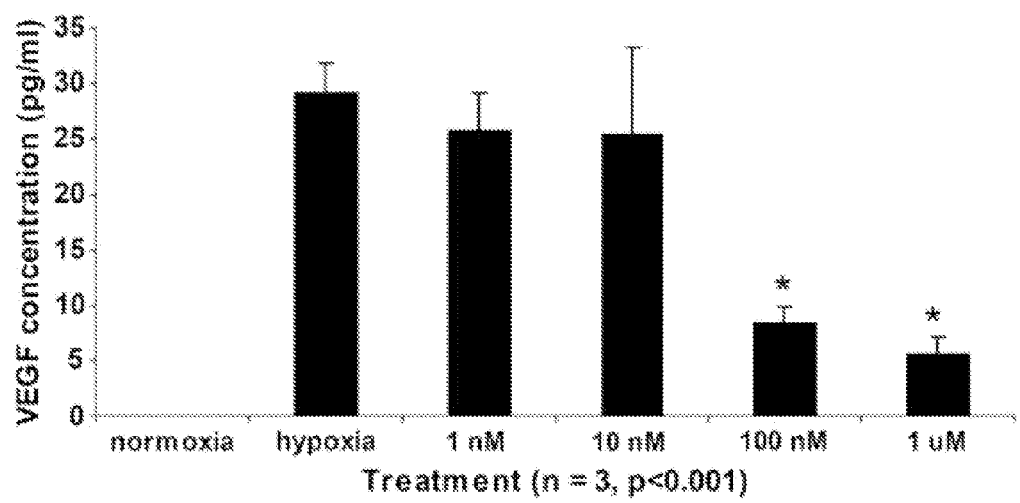
FIG. 9 is a graph of VEGF secretion in 4T1 cells after hypoxia treatment, with and without treatment of different amounts of manassantin A.

Effect of Manassantin A on HIF-1 Regulated VEGF Secretion:

Vascular endothelial growth factor (VEGF) is a gene that is highly involved in tumor progression as a pro-angiogenic factor. The effects of manassantin A (1) on HIF-1 regulated VEGF secretion were examined in 4T1 cells using ELISA. Cells were incubated under hypoxia (0.5% $O_2$ for 24 h) with various concentrations (0, 1, 10, 100 nM, and 1 μM) of manassantin A. Cell culture supernates were collected, and VEGF levels in supernates were measured by a commercially available ELISA kit (R&D systems, Minneapolis, Minn.). As observed from HIF-1 expression, VEGF induced by hypoxia was significantly inhibited by manassantin A at concentrations higher than 10 nM (FIG. 9).

Example 8

Figure 10:
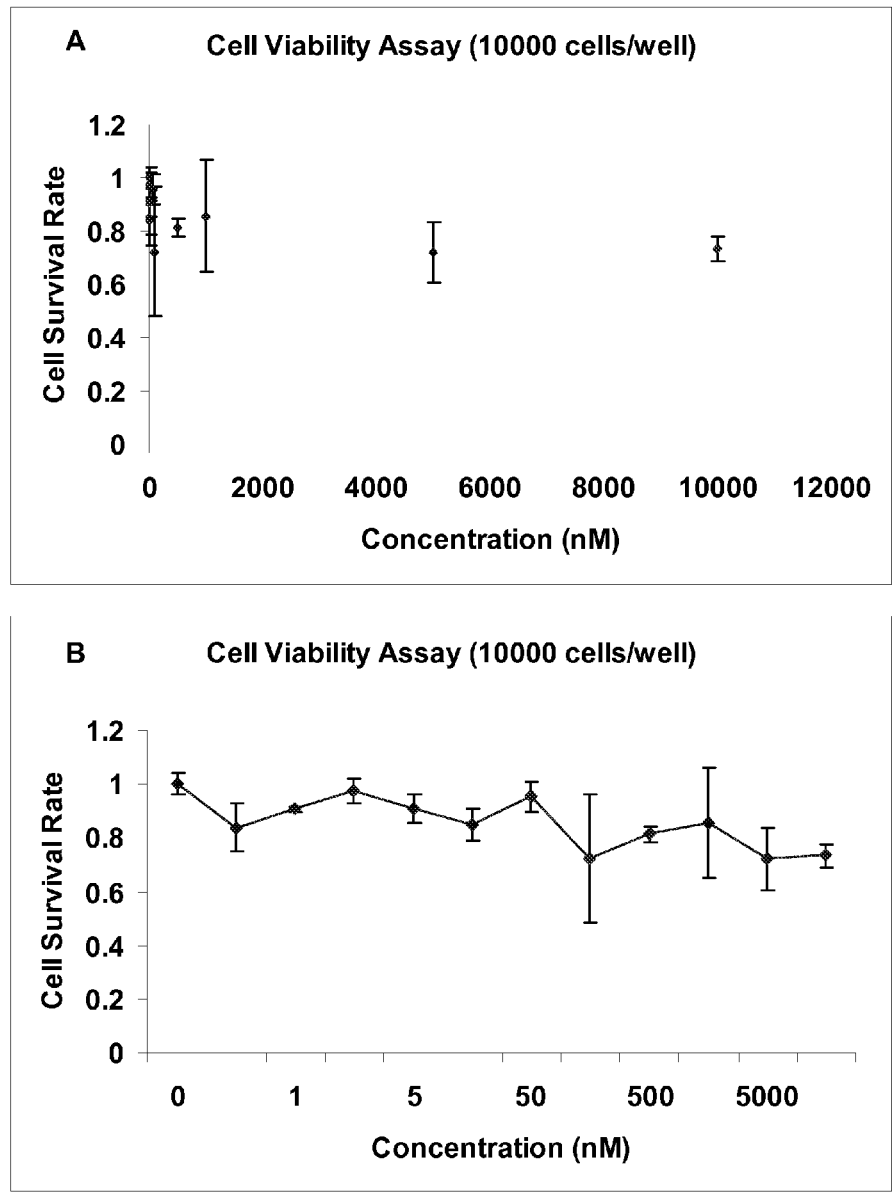
FIG. 10 are graphs of manassantin A concentration versus cell survival rates using an MTS assay.

Cytotoxicity of Manassantin A (MTS Assay):

Cytotoxicity of manassantin A was examined using the MTS assay, a standard colorimetric cytotoxicity assay. Like MTT (3-(4,5-d imethylthiazol-2-yl)-2,5-diphenyltetrazolium bromide, a tetrazole), MTS was reduced into a formazan product by living cells in the presence of an electron coupling reagent (phenazine methosulfate, PMS). The absorbance of the formazan was detected at 490 nm. 4T1 cells were seeded in a 96-well plate and incubated with serially diluted manassantin A (0-10 µM) for 24 h. Then cells were washed and incubated another three hours with cell medium containing MTS/PMS solution at 37° C. (21% $O_2$, 5% $CO_2$). Relative cell survival rate was determined on the O.D. values measured at 490 nm. Up to the highest concentration examined (10 µM), cells had ~70% survival rate. Considering that manassantin A completely inhibited the expression of HIF-1 at the concentration 100 nM, manassantin A possessed a significant therapeutic window ($IC_{50}$ (cytotoxicity)/$IC_{50}$ (HIF-1 inhibition) 100). Results are shown in FIGS. 10A and 10B.

Example 9

NCI-60 DTP Human Tumor Cell Line Screen: One Dose Mean Graph, Trial 1:

The effects of manassantin A (1) on cancer cell lines were evaluated using the NCI-60 DTP Human Tumor Cell Line Screen. The NCI-60 DTP Human Tumor Cell Line Screen utilized 60 different human tumor cell lines, representing leukemia, melanoma, and cancers of the lung, colon, brain, ovary, breast, prostate, and kidney. The screening was a two-stage process. First, manassantin A was evaluated against all 60 cell lines at a single dose of 10 µM. Second, manassantin A was evaluated against the 60 cell panel at five concentration levels.

The human tumor cell lines of the cancer screening panel were grown in RPMI 1640 medium containing 5% fetal bovine serum and 2 mM L-glutamine. For a typical screening experiment, cells were inoculated into 96 well microtiter plates in 100 µL at plating densities ranging from 5,000 to 40,000 cells/well depending on the doubling time of individual cell lines. After cell inoculation, the microtiter plates were incubated at 37° C., 5% $CO_2$, 95% air and 100% relative humidity for 24 h prior to addition of manassantin A.

After 24 h, two plates of each cell line were fixed in situ with TCA, to represent a measurement of the cell population for each cell line at the time of drug addition (Tz). Manassantin A was solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 µg/mL gentamicin. Additional four, 10-fold, or ½ log serial dilutions were made to provide a total of five drug concentrations plus control. Aliquots of 100 µL of these different drug dilutions were added to the appropriate microtiter wells already containing 100 µL of medium, resulting in the required final drug concentrations.

Following addition of manassantin A, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 µL of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 µL) at 0.4% (w/v) in 1% acetic acid was added to each well, and plates were incubated for 10 minutes at room temperature. After staining, unbound dye was removed by washing five times with 1% acetic acid, and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 µL of 80% TCA (final concentration, 16% TCA). Using the seven absorbance measurements [time zero, (Tz), control growth, (C), and test growth in the presence of drug at the five concentration levels (Ti)], the percentage growth was calculated at each of the drug concentrations levels. Percentage growth inhibition was calculated as:

[(Ti−Tz)/(C−Tz)]×100 for concentrations for which Ti>/=Tz

[(Ti−Tz)/Tz]×100 for concentrations for which Ti<Tz.

Three dose response parameters were calculated for each experimental agent: $GI_{50}$, TGI, and $LC_{50}$. Growth inhibition of 50% ($GI_{50}$) was calculated from [(Ti−Tz)/(C−Tz)]×100=50, which is the drug concentration resulting in a 50% reduction in the net protein increase (as measured by Sulphor-hodamine-B (SRB) staining) in control cells during the drug incubation. The drug concentration resulting in total growth inhibition (TGI) was calculated from Ti=Tz. The $LC_{50}$ (concentration of drug resulting in a 50% reduction in the measured protein at the end of the drug treatment as compared to that at the beginning) indicating a net loss of cells following treatment was calculated from [(Ti−Tz)/Tz]×100=−50. Values were calculated for each of these three parameters if the level of activity was reached; however, if the effect was not reached or is exceeded, the value for that parameter was expressed as greater or less than the maximum or minimum concentration tested.

Figure 11:
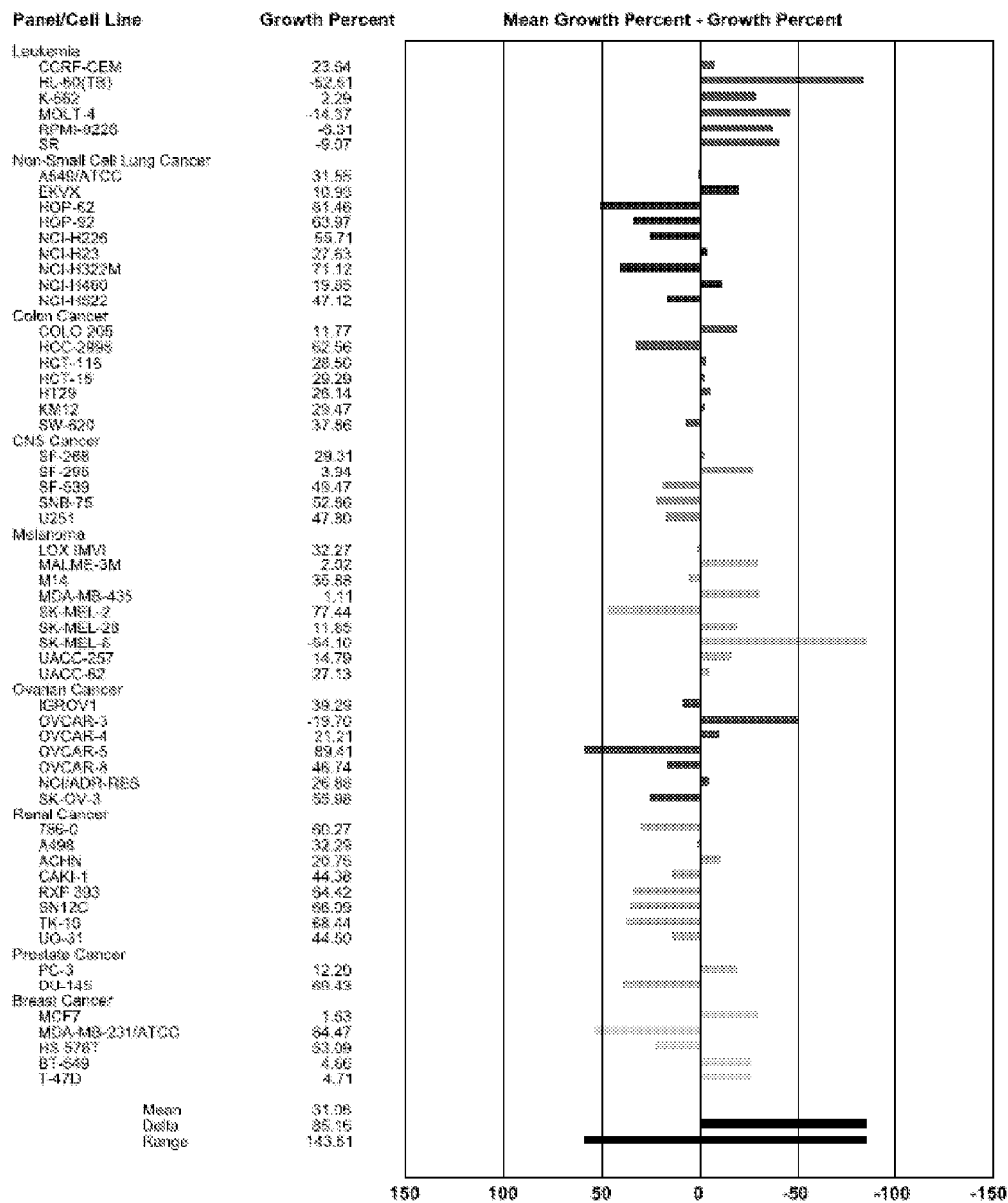
FIG. 11 is a graph of the mean growth percent of various human cancer cell lines with one dose of manassantin A.
Figure 12:
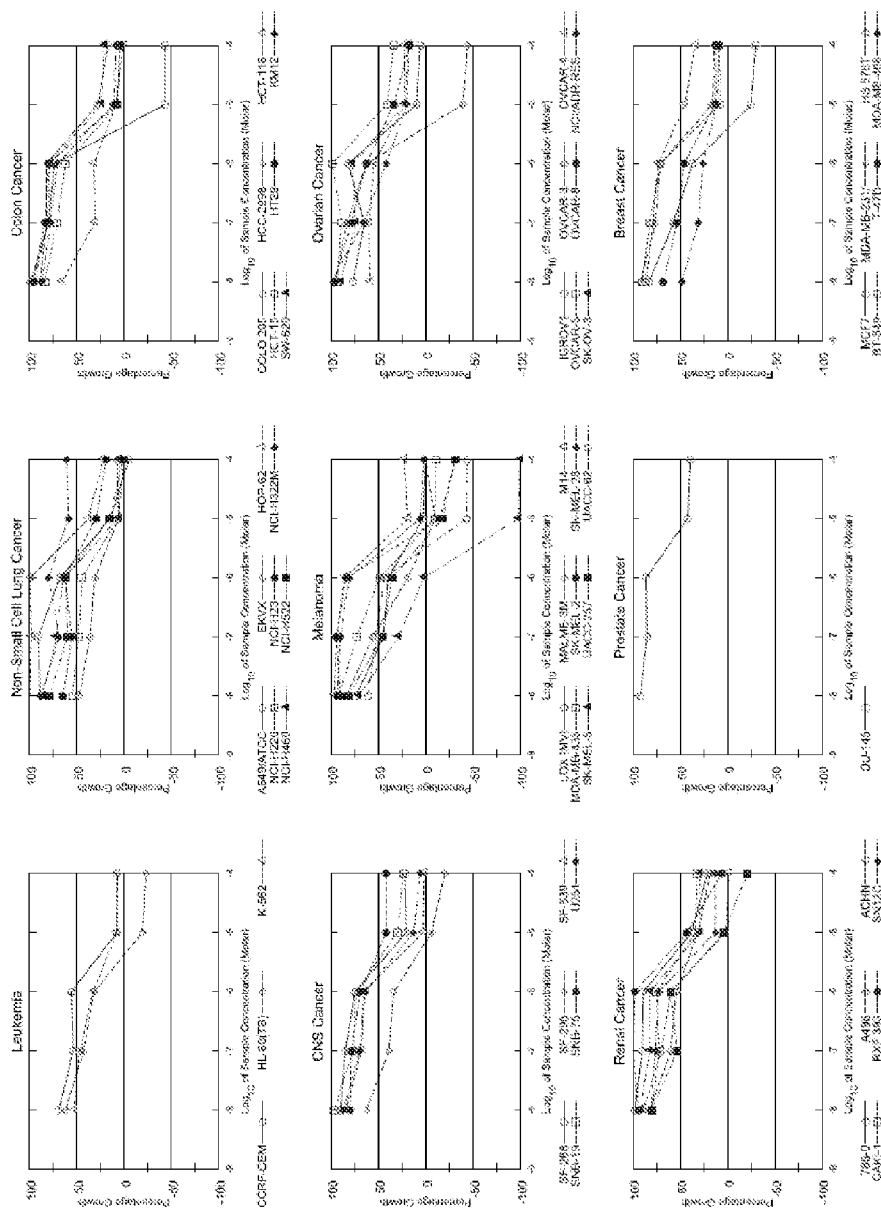
FIG. 12 are graphs of the growth of various human cancer cell lines with various doses of manassantin A (trial 1).
Figure 13:
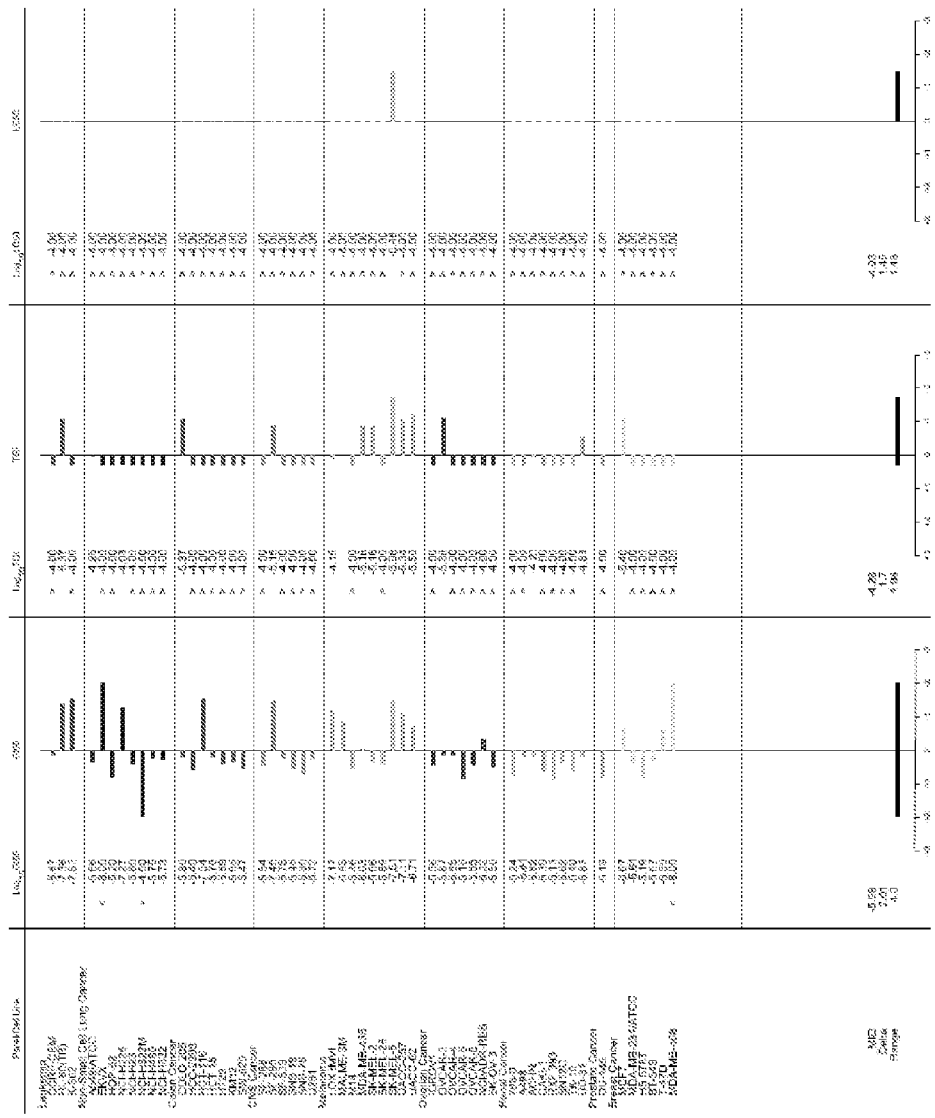
FIG. 13 shows the $GI_{50}$, TGI, and $LC_{50}$ determined for the effect of manassantin A on various human cancer cell lines (trial 1).
Figure 14:
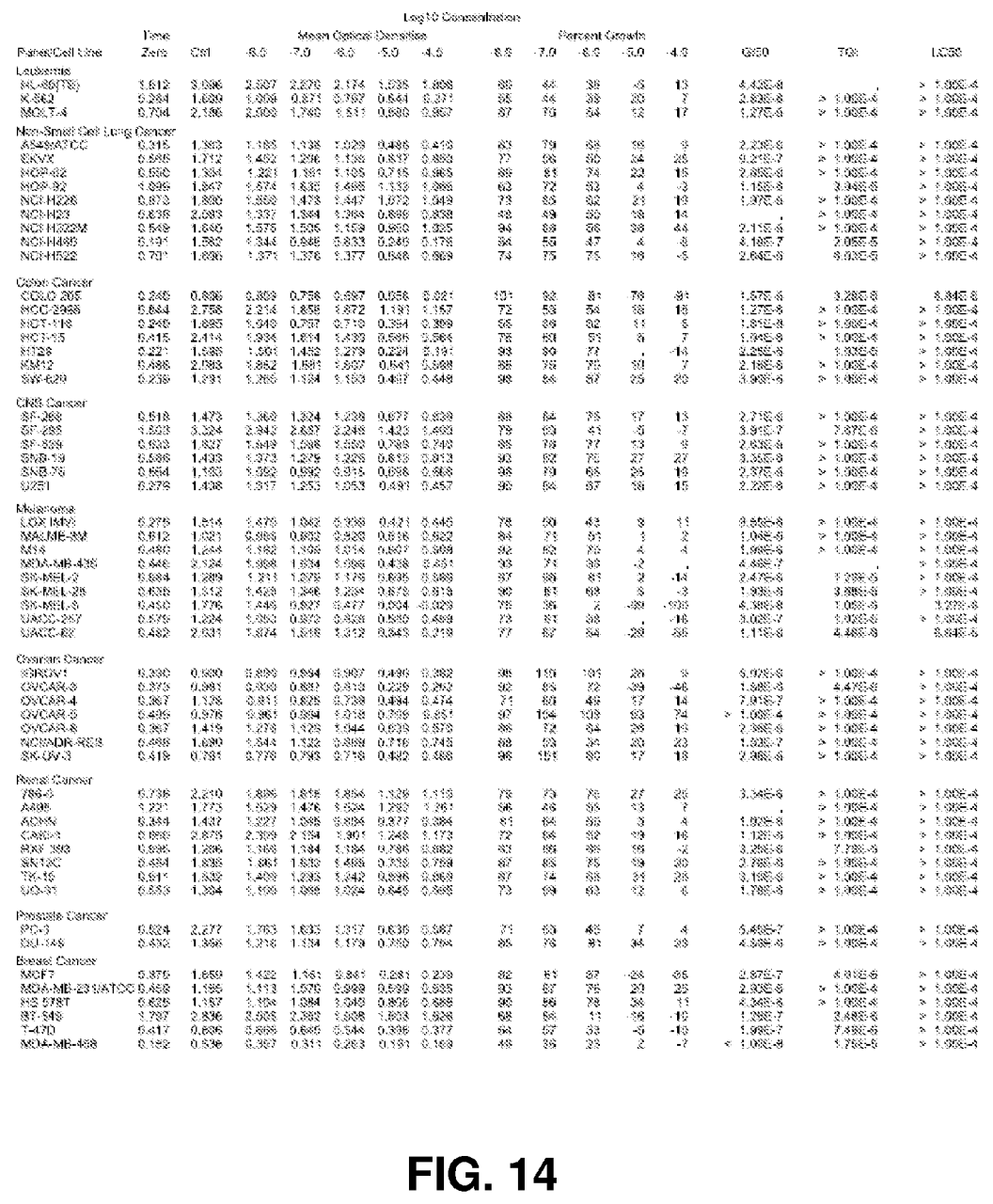

As shown in FIG. 11, a single dose (10 µM) of manassantin A reduced the growth of all tumors tested, including leukemia, non-small cell lung cancer, colon cancer, CNS cancer, melanoma, ovarian cancer, renal cancer, prostate cancer, and breast cancer. Further, a single dose (10 µM) of manassantin A was more than 50% lethal to leukemia, melanoma, and ovarian cancer. Results shown in FIGS. 12-14 further support this finding.

Example 10

NCI-60 DTP Human Tumor Cell Line Screen: One Dose Mean Graph, Trial 2

Figure 15:
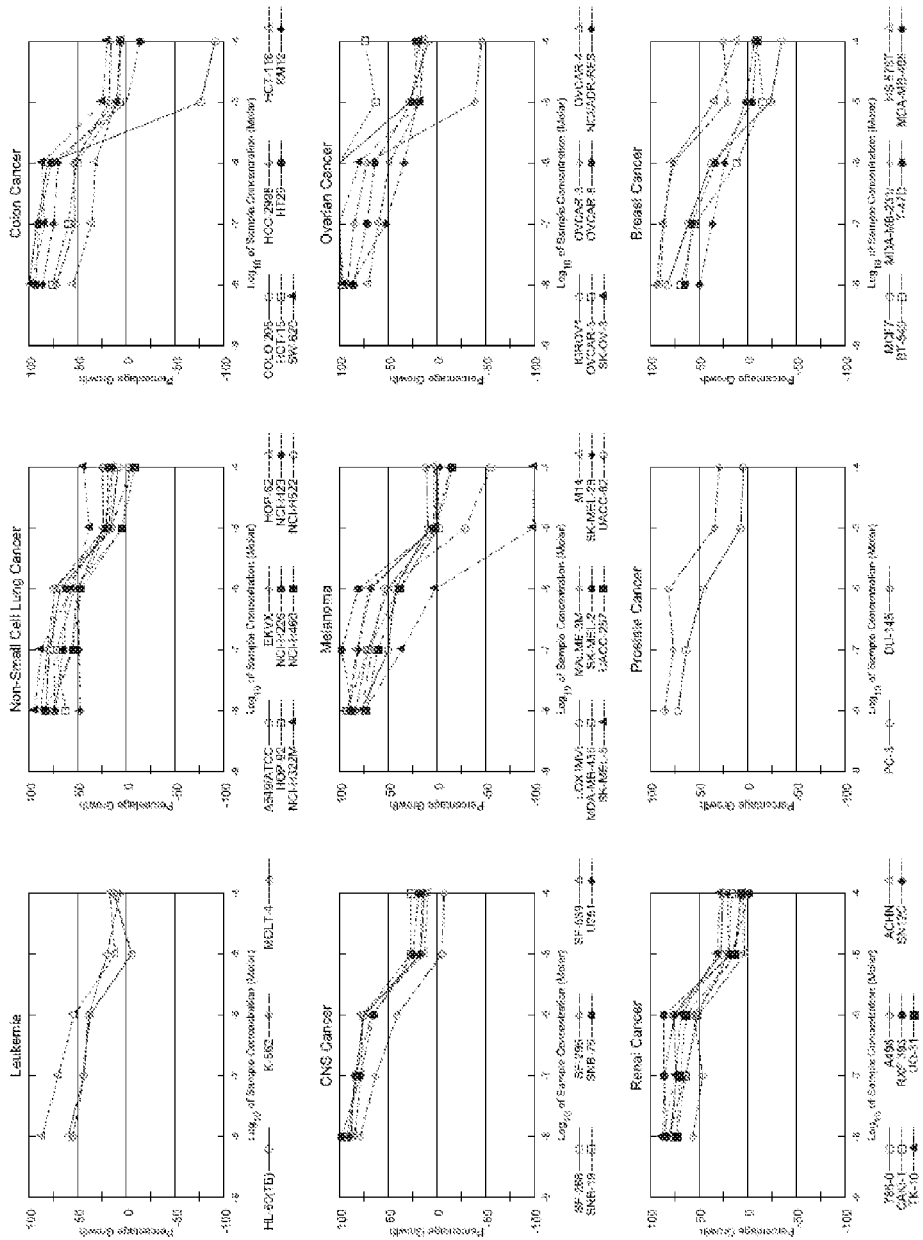
FIG. 15 are graphs of the growth of various human cancer cell lines with various doses of manassantin A (trial 2).
Figure 16:
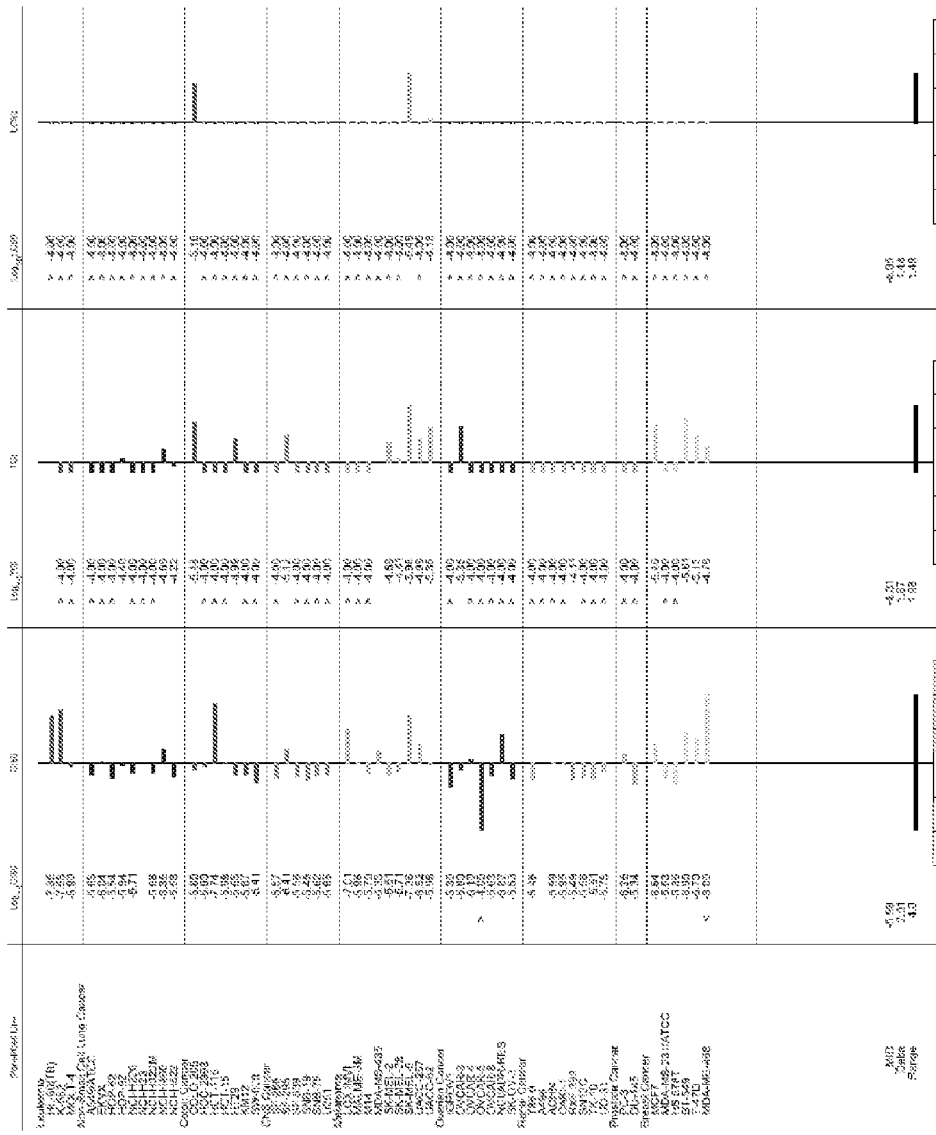
FIG. 16 is shows the $GI_{50}$, TGI, and $LC_{50}$ determined for the effect of manassantin A on various human cancer cell lines (trial 2).
Figure 17:
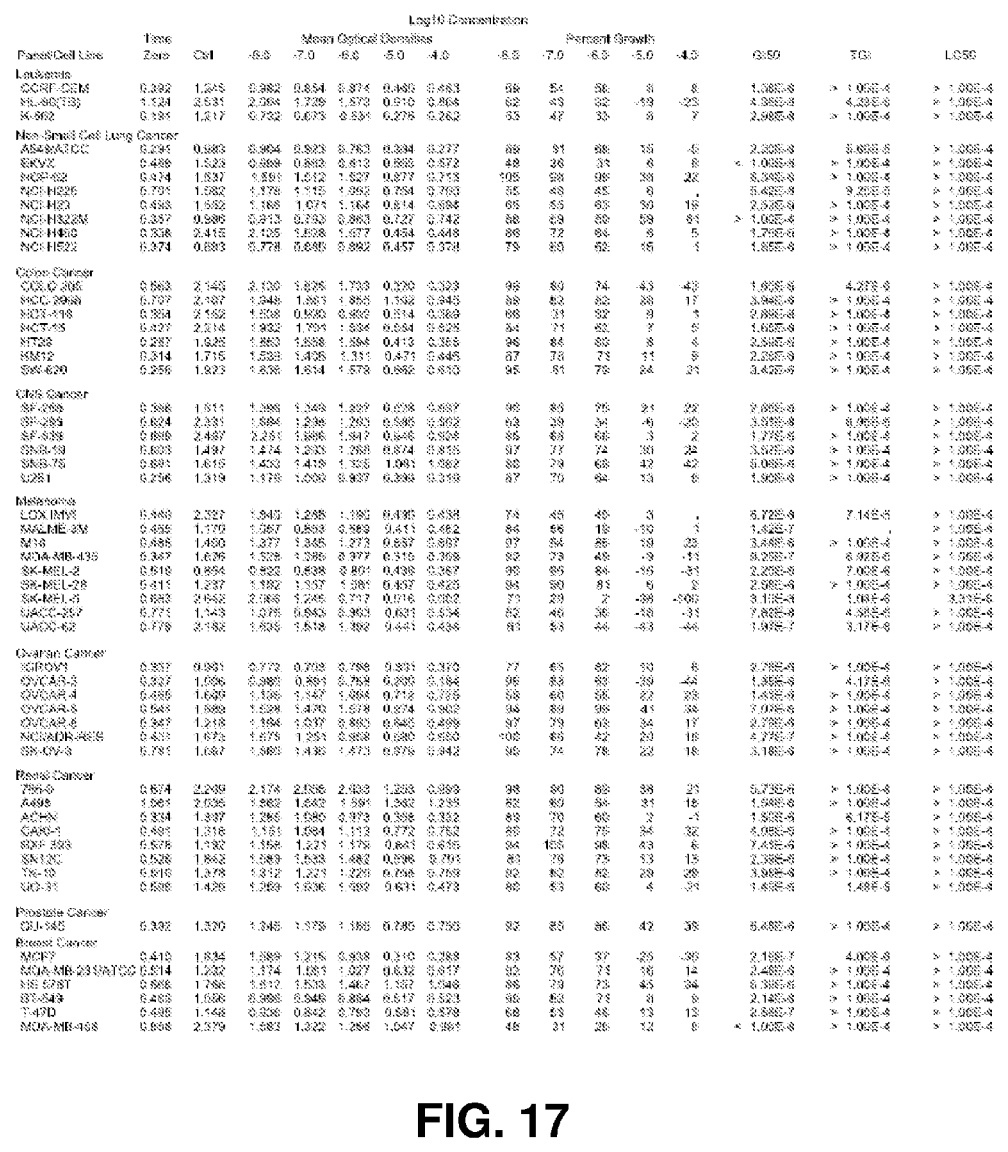

The effects of manassantin A on cancer cell lines were evaluated as described in Example 9 for a second trial. As shown in FIGS. 15-17, manassantin A reduced the growth of all tumors tested, including leukemia, non-small cell lung cancer, colon cancer, CNS cancer, melanoma, ovarian cancer, renal cancer, prostate cancer, and breast cancer. Further, a single dose (10 µM) of manassantin A was more than 50% lethal to leukemia, melanoma, and ovarian cancer.

Example 11

Animal Toxicity Assay:

The effect of manassantin A (1) on non-tumored animals was examined to analyze the toxicity. All treatment was administered according to exact body weight. A single Athymic Nude mouse was given a single injection (IP) of 400 mg/kg; a second mouse received a dose of 200 mg/kg, and a third mouse received a single dose of 100 mg/kg. The mice were observed for a period of 2 weeks. They were sacrificed if they lost more than 20% of their body weight or if there were other signs of significant toxicity. Since all 3 mice had to be sacrificed, the next 3 dose levels (50, 35, and 12.5 mg/kg) were tested in a similar manner. This process was repeated until a tolerated dose was found. This dose was then designated the maximum tolerated dose (MTD). The mice were allowed ad libitum feed and water. Injections were administered IP. Dose volumes were generally 0.1 mL/10 grams body weight but may be up to 0.2 mL/10 grams of body weight. As shown in Table 1, manassantin A was non-toxic at levels of 6.25, 3.13, and 1.56 mg/kg/dose but resulted in death at levels of 12.50 and 100.00 mg/kg/dose.

TABLE 1

Non-tumored animal toxicity assay for manassantin A, single dose

|  | Group 4 | Group 11 | Group 12 | Group 13 | Group 14 |
|---|---|---|---|---|---|
| Dose/Units (mg/kg/dose) | 100.00 | 12.50 | 1.56 | 3.13 | 6.25 |
| Route | IP | IP | IP | IP | IP |
| Carrier | 100% DMSO | 100% DMSO | 100% DMSO | 100% DMSO | 100% DMSO |
| Concentration administered | 200.0 mg/mL | 25.0 mg/mL | 3.125 mg/mL | 3.125 mg/mL | 3.125 mg/mL |
| Solubility | soluble, no visible particles | soluble, no visible particles | soluble, no visible particles | soluble, no visible particles | soluble, no visible particles |
| Administration | injection vol of 0.5 µL/g body wt | injection vol of 0.5 µL/g body wt | injection vol of 0.5 µL/g body wt | injection vol of 1 µL/g body wt | injection vol of 2 µL/g body wt |
| Death Days | 0 | 0 | none | none | none |
| Survivors/Total at day 15 | 0/1 | 0/1 | 1/1 | 1/1 | 1/1 |

Example 12

HIF-1 Inhibitory Activity of Manassantin A Analogs:

The configuration of manassantin A is largely determined by the 2,3-cis-3,4-trans-4,5-cis-configuration of the tetrahydrofuran core, and to test whether the overall conformation is an important determinant for the binding mode and affinity toward molecular target(s), potency, and HIF-1 signaling specificity of manassantin A, manassantin A analogues with modifications in tetrahydrofuran configuration were prepared (Kim, H.; Wooten, C. M.; Park, Y.; Hong, J. *Org. Lett.* 2007, 9, 3965; Kim, H.; Baker, J. B.; Lee, S.-U.; Park, Y.; Bolduc, K. L.; Park, H.-B.; Dickens, M. G.; Lee, D.-S.; Kim, Y.-C.; Kim, S. H.; Hong, J. *J. Am. Chem. Soc.* 2009, 131, 3192; Kim, H.; Kasper, A. C.; Moon, E. J.; Park, Y.; Wooten, C. M.; Dewhirst, M. W.; Hong, *J. Org. Lett.* 2009, 11, 89, all three of which are incorporated by reference) and evaluated.

Synthesis

Figure 18:
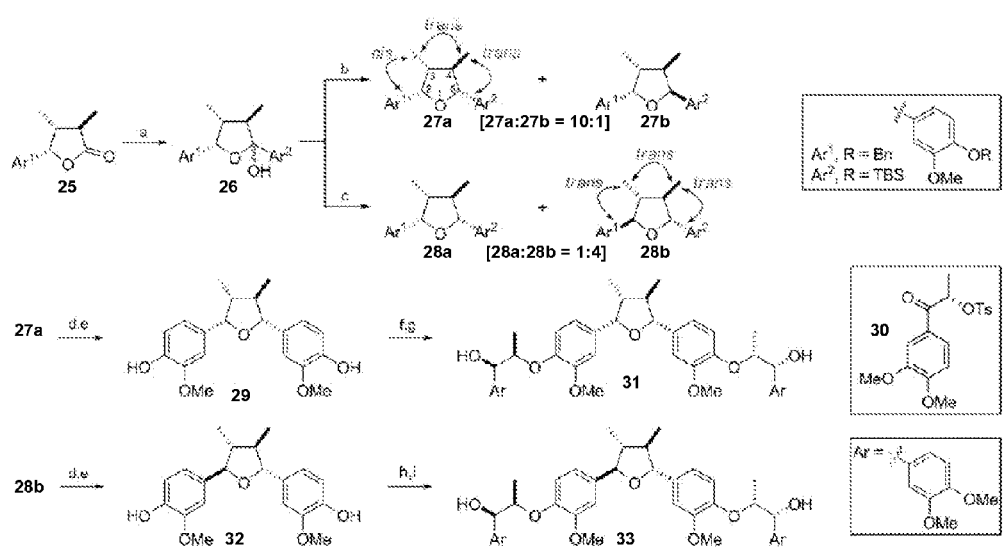
FIG. 18 is a scheme of the chemical synthesis of manassantin A analogs with 2,3-cis-3,4-trans-4,5-trans- and 2,3-trans-3,4-trans-4,5-trans-tetrahydrofuran cores (31 and 33).

The synthesis of manassantin A analogues with 2,3-cis-3,4-trans-4,5-trans- and 2,3-trans-3,4-trans-4,5-trans-tetrahydrofuran cores (31 and 33) was accomplished as shown in FIG. 18. Briefly, the 2,3-cis-3,4-trans-4,5-tetrahydrofuran 27a was prepared via $BF_3 \cdot OEt_2$-promoted deoxygenation of cyclic hemiketal 26 (Kim, H.; Wooten, C. M.; Park, Y.; Hong, J. *Org. Lett.* 2007, 9, 3965, incorporated by reference) followed by stereoselective reduction of the oxocarbenium ion intermediate. Deprotection of the Bn and TBS groups, BEMP-mediated coupling, and polymer-supported $BH_4$-reduction completed the synthesis of 31. Compound 33 was prepared via $BF_3 \cdot OEt_2$-promoted epimerization/reductive deoxygenation followed by deprotection, BEMP-mediated coupling, and polymer-supported $BH_4$-reduction. With reference to FIG. 18, 25 was reacted (a) with $Ar^2$ and THF at −78° C. for 40 min to make 26 with 70% yield. 26 was reacted (b) with either $BF_3 \cdot OEt_2$, $NaBH_3CN$ and $CH_2Cl_2$ at −78° C. for 30 min to make 27a and 27b at a ratio of 10:1 with 99% yield, or reacted (c) with $BF_3 \cdot OEt_2$ and $CH_2Cl_2$ at −78° C. to −20° C. for 2 h and then with $NaBH_3CN$ at −78° C. for 30 min to make 28a and 28b at a ratio of 1:4 with 96% yield. 27a was reacted (d) with $H_2$, Pd/C, EtOAc/EtOH (3:1) at 25° C. for 2h and then (e) with TBAF and THF at 25° C. for 1 h to make 29 with 88% yield. 29 was reacted (f) with BEMP and $CHCl_2$ at 25° C. for 18 h with 66% yield and then reacted (g) with (polystyrylmethyl)trimethylammonium borohydride and MeOH at 25° C. for 48 h to yield 31 with 75% yield. 28b was reacted (d) with $H_2$, Pd/C, EtOAc/EtOH (3:1) at 25° C. for 2h and then (e) with TBAF and THF at 25° C. for 1 h to make 32 with 88% yield. 32 was reacted (h) with BEMP and $CHCl_2$ at 25° C. for 20 h with 92% yield and then (i) with (polystyrylmethyl) trimethylammonium borohydride and MeOH at 25° C. for 30 h to make 33 with 86% yield.

HIF-1 Inhibition

Figure 19:
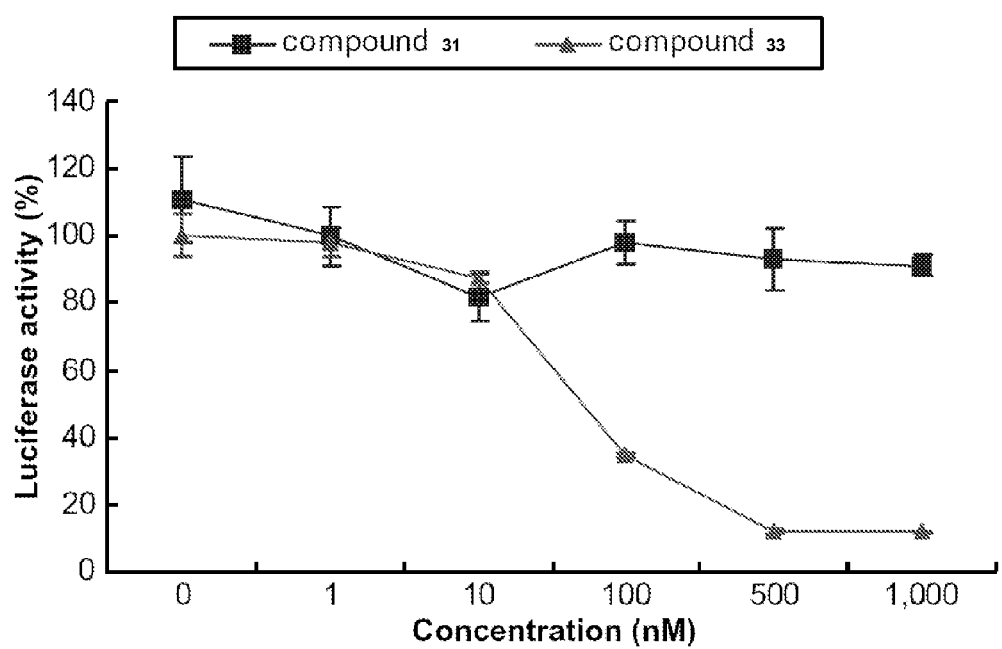
FIG. 19 is a graph of luciferase activity as a function of the concentration of the manassantin A analogs with 2,3-cis-3,4- trans-4,5-trans- and 2,3-trans-3,4-trans-4,5-trans-tetrahydrofuran cores (31 and 33) to determine the HIF-1 inhibitory activity of 31 and 33.

To determine HIF-1 inhibitory activity of 31 and 33, a luciferase-reporter based assay was used as a primary screen. For this assay, 4T1-ODD-Luc cells (Li, F.; Sonveaux, P.; Rabbani, Z. N.; Liu, S.; Yan, B.; Huang, Q.; Vujaskovic, Z.; Dewhirst, M. W.; Li, C. Y. *Mol. Cell* 2007, 26, 63, incorporated by reference) stably transfected with the oxygen-dependent-degradation (ODD) domain of HIF-1 and a firefly luciferase reporter was used. This ODD-Luc reporter contained a CMV promoter, which is constitutively active. Since its ODD domain is identical to that of HIF-1, it enabled the direct detection of the stability of HIF-1. Cells were seeded in the 24-well plate at a density of $10^5$ cells/well. After 16-h incubation, cells were treated with 240 µM of $CoCl_2$ and serially diluted compounds for 24 h. Since luciferase requires $O_2$ for its activity but the ODD-Luc is highly sensitive to reoxygenation, HIF-1 expression was induced by $CoCl_2$, not by hypoxia, to accurately determine the effect of the compounds on HIF-1 stability. Luciferase signals were detected and quantified as relative light units (RLUs). The ODD-Luc assay to assess HIF-1 inhibitory activity of 31 and 33 revealed that 31 was nearly inactive and 33 was less active than manassantin A by 10-fold ($IC_{50}$=47 nM) (FIG. 19). The results indicated that the 2,3-cis-3,4-trans-4,5-cis-configuration of the tetrahydrofuran core may be important for HIF-1 inhibition.

Example 13

Optimized Conformations:

To further characterize the effect of tetrahydrofuran conformation of manassantin A, 31, and 33 on the HIF-1 inhibition, conformations of truncated structures (to avoid any unnecessary complications and/or exaggeration by the flexible side chains, truncated structures of 1, 31, and 33 were used instead of the full structures. Initial geometries were determined by conformational search based on molecular mechanics (MMFF)) were optimized using density functional theory (B3LYP)(Lee, C.; Yang, W.; Parr, R. G. *Phys. Rev. B* 1988, 37, 785; Vosko, S.; Wilk, L.; Nusair, M. Can. *J. Phys.* 1980, 58, 1200; Becke, A. D. *Phys. Rev. A* 1988, 38, 3098; Becke, A. D. *J. Chem. Phys.* 1993, 98, 5648, all four of which are incorporated by reference) at the 6-31G* level (GAUSSIAN 03, D.02 version; Frisch, M. J.; Trucks, G. W.; Schlegel, H. B.; Scuseria, G. E.; Robb, M. A.; Cheeseman, J. R.; Montgomery, J. A., Jr.; Vreven, T.; Kudin, K. N.; Burant, J. C., et al. GAUSSIAN 03, Revision D.02; Gaussian: Wallingford, Conn., 2004). FIG. 20 shows the optimized conformations of truncated structures of manassantin A, 31, and 33, wherein FIG. 20*a* are the structures, FIG. 20*b* is Overlay I, FIG. 20*c* is Overlay II front view, and FIG. 20*d* is Overlay II side view. As shown in FIG. 20, compound 34 adopted a nearly linear conformation, but compound 35 adopted a bent-shaped conformation remarkably different from that of 34. However, in one of the two possible orientations for 36 (Overlay II, FIG. 20*c*), the conformation was relatively close to that of 34 (FIGS. 20*c* and 20*d*), indicating that the linear-shaped conformation resulting from the 2,5-transconfiguration may be important to the HIF-1 inhibition. Thus, designing a ligand that mimics the overall conformation of manassantin A may improve the potency and selectivity toward the hypoxia signaling pathway.

Example 14

Inhibition of Interleukin-2:

Human E6.1 Jurkat T cells were cultured in RPMI-1640 with 10% fetal bovine serum (FBS), 2 mM I-glutamine, and 1 mM Na-pyruvate. After serum starvation for 7 h, Jurkat cells were plated in 96 well culture plates at 1.25×105 cells/mL in RPMI-1640 (without phenol red) with 10% FBS. Cells were treated with phorbol 12-myristate 13-acetate (PMA, 1.25 ng/mL) and phytohemaglutinin (PHA, 0.25 µg/mL) to stimulate secretion of IL-2. Testing compound or DMSO vehicle was added to appropriate wells. The testing compound was either manassantin A (1), compound 22, or Psora4. Psora4 was used as a positive control, i.e., it inhibited release of IL-2. Plates were then incubated for 18 h. Cell supernatants were collected (100 µL) and assayed for interleukin-2 (IL-2) by ELISA (Human IL-2 ELISA Kit, available from BD Biosciences, San Jose, Calif.). All test conditions were assayed in triplicate and verified with repeated experiments three times. As shown in FIG. 21, manassantin A (1) and 22 both inhibited the release of interleukin-2. In FIG. 21, SU2-SU6 are test compounds not relevant to the invention.

Example 15

Chemical Synthesis of Manassantin Analogs:

The synthetic method for construction of 2,3-cis-3,4-trans-4,5-trans-tetrahydrofurans via $BF_3.OEt_2$-promoted deoxygenation of cyclic hemiketals followed by stereoselective reduction of oxocarbenium ion intermediates is applied to the synthesis of (−)-odoratisol C, (−)-futokadsurin A, and (−)-veraguensin (FIG. 21) (Kim, H.; Wooten, C. M.; Park, Y.; Hong, J. *Org. Lett.* 2007, 9, 3965-3968, incorporated by reference). The $BF_3.OEt_2$-promoted epimerization of the cyclic hemiketals synthetic method is explored and used in the synthesis of 2,3-trans-3,4-trans-4,5-trans-tetrahydrofuran lignans such as (+)-fragransin $A_2$, (+)-galvelgin, and (+)-talaumidin (FIG. 22).

Synthesis of manassantin A analogues with 2,3-cis-3,4-trans-4,5-trans- and 2,3-trans-3,4-trans-4,5-trans-tetrahydrofurans (60 and 65) are accomplished as described in FIGS. 23 and 24. Briefly, the 2,3-cis-3,4-trans-4,5-trans-tetrahydrofuran 56 is prepared via $BF_3.OEt_2$-promoted deoxygenation of cyclic hemiketal 55 (Kim, H.; Wooten, C. M.; Park, Y.; Hong, J. *Org. Lett.* 2007, 9, 3965-3968, incorporated by reference) followed by stereoselective reduction of the oxocarbenium ion intermediate. Deprotection of Bn group, BEMP-mediated coupling, and polymer-supported $BH_4$-reduction complete the synthesis of 60 (FIG. 23).

Compound 65 is prepared via $BF_3.OEt_2$-promoted epimerization/reductive deoxygenation followed by BEMP-mediated coupling and polymer-supported $BH_4$-reduction (FIG. 24).

The oxygen atom in the tetrahydrofuran core may play an important role not only as a determinant for the conformation of the THF core, but also a hydrogen bond acceptor. To assess the effect on conformation and the role of hydrogen bond in HIF-1 inhibition by replacement of the oxygen atom with nitrogen atom, the synthesis of pyrrolidine analogue 86 of manassantin A is achieved as with the synthesis of 1. As described in FIG. 25, lactam 86 is synthesized from the known anti-adol adduct 78 (Evans, D. A.; Downey, C. W.; Shaw, J. T.; Tedrow, J. T. *Org. Lett.* 2002, 4, 1127-1130, incorporated by reference). From 84, DIBALH-reduction, treatment with $PhSO_2H$ and camphorsulfonic acid, and subsequent addition of the organozinc reagent completes the synthesis of the 2,3-cis-3,4-trans-4,5-cis-pyrrolidine core 86. If the addition reaction does not provide 72 in good diastereoselectivity, an alternative method is used. Installation of exo-methylene group, nucleophilic addition of organozinc, and asymmetric reduction provides the desired pyrrolidine core 86 in good diasteoselectivity. The pyrrolidine analogue 89 is obtained via coupling reaction and stereoselective reduction as shown in FIG. 25.

The repulsive 1,2-interactions of C3 and C4 methyl groups with the C2 and C5 substituents may affect the conformation of the tetrahydrofuran core. The mono-methyl analogue 93 and the desmethyl analogue 102 are prepared as described in FIGS. 26 and 27. The mono-methyl tetrahydrofuran 90 is coupled to 63 followed by polymer-supported $BH_4$ reduction to complete the synthesis of 93 (FIG. 26).

The 2-benzenesulfonyl ether 98 is prepared from the acetate-aldol adduct 95 (Hodge, M. B.; Olivo, H. F. *Tetrahedron* 2004, 60, 9397-9403, incorporated by reference) following the standard procedures (FIG. 27). Nucleophilic addition of (4-benzyloxy-3-methoxyphenyl)zinc(II) bromide to the 2-benzylsulfonly ether 98 stereoselectively provides 99 via the Woerpel's inside attack model (Hossain, C. F.; Kim, Y.-P.; Baerson, S. R.; Zhang, L.; Bruick, R. K.; Mohammed, K. A.; Agarwal, A. K.; Nagle, D. G.; Zhou, Y.-D. *Biochem. Biophys.*

Res. Commun. 2005, 333, 1026-1033, incorporated by reference). Due to the absence of significant repulsive interaction of C4-substituent with an incoming nucleophile, the nucleophilic addition of (4-benzyloxy-3-methoxyphenyl)zinc(II) bromide to 98 provides 99 with excellent stereoselectivity (Kim, H.; Kasper, A. C.; Moon, E. J.; Park, Y.; Wooten, C. M.; Dewhirst, M. W.; Hong, J. Org. Lett. 2009, 11, 89-92, incorporated by reference).

Shorter side chains may decrease or abolish the HIF-1 inhibitory activity of manassantins, and an extended side chain analogue 110 is prepared as described in FIG. 28.

Two analogues, keto analogue 111 and methoxy analogue 112 prepared. The keto analogue 111 is a synthetic intermediate to manassantin A (1). Treatment of 1 with NaH and MeI provides 112, as shown in FIG. 29.

Both methyl groups are replaced with hydrogens following the procedures described in FIG. 30. Briefly, BEMP-mediated coupling of 106 with 113 followed by asymmetric CBS-reduction (Corey, E. J.; Helal, C. J. Angew. Chem., Int. Ed. Engl., 1998, 37, 1986-2012, incorporated by reference) of the keto groups provides 115.

De-oxo analogues 117 and 119 are prepared by coupling of 116 and 118, respectively (FIG. 31). Since the tosylates 116 and 118 are less reactive than 63, the coupling reaction may require harsher conditions (e.g. higher reaction temperature).

120 is prepared and evaluated as shown in FIG. 32.

Example 16

Inhibition of Cancer Progression Using Manassantin Compounds and Analogues:
Animals Female Fisher-344 rats, C57/B16 mice, and Balb/C mice are housed and treated in accordance with approved guidelines from the Duke University Institutional Animal Care and Use Committee.
Tumors 4T1 tumors are grown in the flank of Balb/C mice by injecting a single cell suspension of tumor cells ($10^5$). Tumor volumes are measured with calipers and calculated according to two diameters with the formula: $v=(a^2 \times b)/2$, where v is the volume, a is the short diameter, and b is the long diameter. Animals are sacrificed once tumors reach five times their initial treatment volumes.
Skinfold Window Chambers Mice are anesthetized with sodium pentobarbitol (80 mg/kg, i.p.), and a 1-cm diameter circular incision is made in the dorsal skin flap, over which a titanium chamber is surgically implanted. A 10-μL suspension of tumor cells ($5 \times 10^3$ cells) is then injected into the opposing flap of skin. A circular cover slip is placed over the incision, through which the vasculature, tissue, and tumor cells are visualized. Observations of window chamber tumors are performed daily on restrained, unanaesthetized mice with an inverted Zeiss fluorescence microscope (Carl Zeiss, Jena, Germany). Images are captured onto a personal computer with Scion Image software (Frederick, Md.) and analyzed with Adobe Photoshop (San Jose, Calif.). Tumor volume and vascular length densities are calculated as follows. Briefly, tumor volumes are calculated with the formula: $d^2(3.14/2)$, where the diameter is determined from low-power (2.5×) microscopy images by comparing pixel dimensions with micrometer values. Vascular length densities are measured from medium-power (5×) fields by using image analysis software (Scion Image) to trace the vascular network. Measurement of the sum length of all vessels within each tumor is then determined (in pixels) and converted to metric length by comparing pixel dimensions with micrometer values.
Tumor Irradiation Animals are randomized to treatment groups once flank tumors reach a mean volume of 200 mm³ (n=5 per group), and window chamber tumors are 1 mm in diameter (n=5 per group). Tumor-bearing Balb/C mice are restrained, unanaesthetized, in a plastic tube and placed in a Mark IV Cesium irradiator (dose rate=7 Gy/min). The mice are positioned behind a lead shield allowing only the tumor-bearing area to remain in the treatment field. Three doses of 5 Gy are administered, separated by 12 h each.
Drug Treatment Manassantins according to the invention are prepared in sterile phosphate buffered saline (PBS) and are administered by i.p. injections (6 mg/kg and 100 mg/kg, respectively) according to the schedules.
Statistics Unless otherwise noted, data are reported as mean±standard deviation. Statistical significance is determined with a Student t test or analysis of variance, where appropriate, and p values less than 0.05 are considered significant.

Example 17

Potentiation of Cells for Anti-Cancer Treatment:

The Dose Enhancing Factor (DEF) is a ratio of the enhancement of cell growth inhibition elicited by the test compound in the presence of bleomycin compared to bleomycin alone. The test compounds (manassantin compounds and analogues) are used at a fixed concentration of 25 μM. Bleomycin is used at a concentration of 0.5 μg/mL. The DEF is calculated from the formula:

$$\frac{Growth_{TC}}{Growth_{Control}} \times \frac{Growth_{bleo}}{Growth_{(bleo+TC)}}$$

where $Growth_{TC}$ is cell growth in presence of the test compound;

$Growth_{control}$ is cell growth of control cells;

$Growth_{bleo}$ is cell growth in presence of bleomycin; and $Growth_{(bleo+TC)}$ is cell growth in presence of bleomycin and the test compound.

Cell growth is assessed using the sulforhodamine B (SRB) assay (Skehan, P., et al., 1990, J. Natl. Cancer Inst., 82, 1107-1112). 2,000 HeLa cells are seeded into each well of a flat-bottomed 96-well microtiter plate in a volume of 100 μL and incubated for 6 hours at 37° C. Cells are either replaced with media alone or with media containing the test compound at a final concentration of 25 μM. Cells are allowed to grow for a further 1 hour before the addition of bleomycin to either untreated cells or test compound treated cells. Cells untreated with either bleomycin or test compound are used as a control. Cells treated with test compound alone are used to assess the growth inhibition by the test compound.

Cells are left for a further 16 hours before replacing the media and allowing the cells to grow for a further 72 hours at 37° C. The media is then removed and the cells fixed with 100 μL of ice cold 10% (w/v) trichloracetic acid. The plates are incubated at 4° C. for 20 minutes and then are washed four times with water. Each well of cells is then stained with 100 μL of 0.4% (w/v) SRB in 1% acetic acid for 20 minutes before washing four times with 1% acetic acid. Plates are then dried for 2 hours at room temperature. The dye from the stained cells is solubilized by the addition of 100 µL of 10 mM Tris Base into each well. Plates are gently shaken and left at room temperature for 30 minutes before measuring the optical density at 564 nM on a Microquant microtiter plate reader.

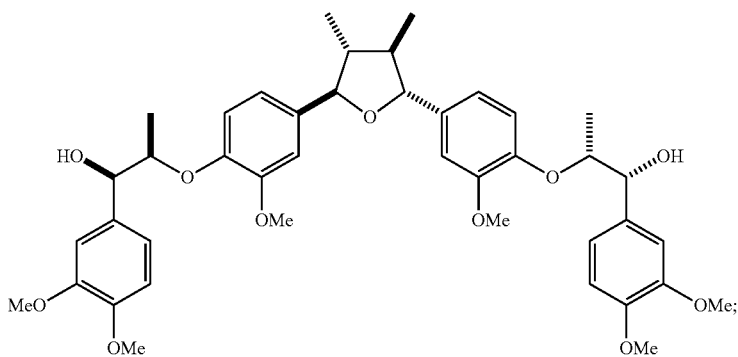

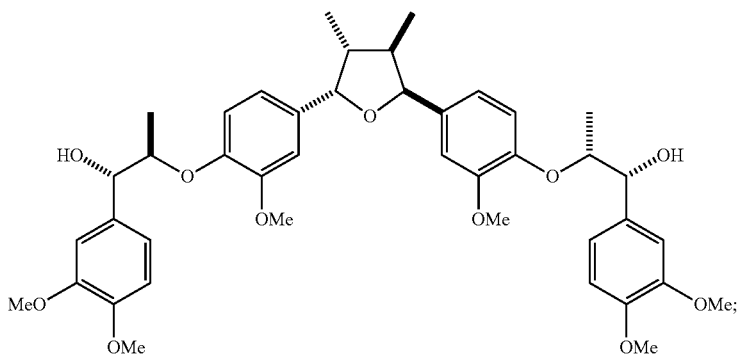

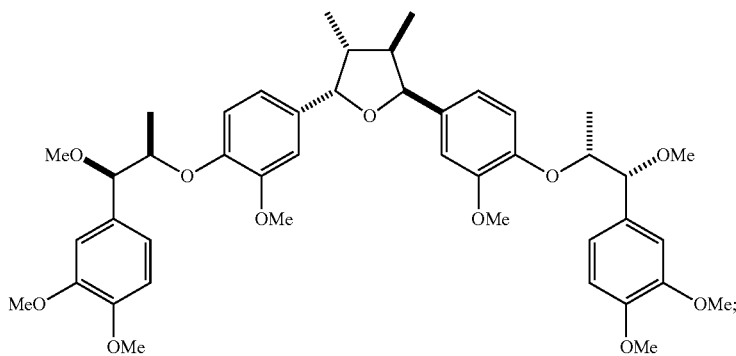
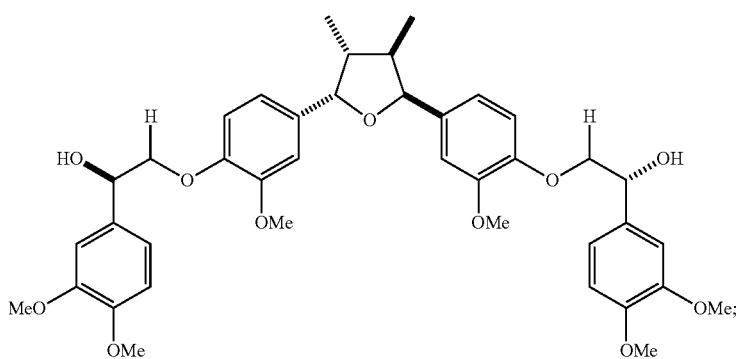
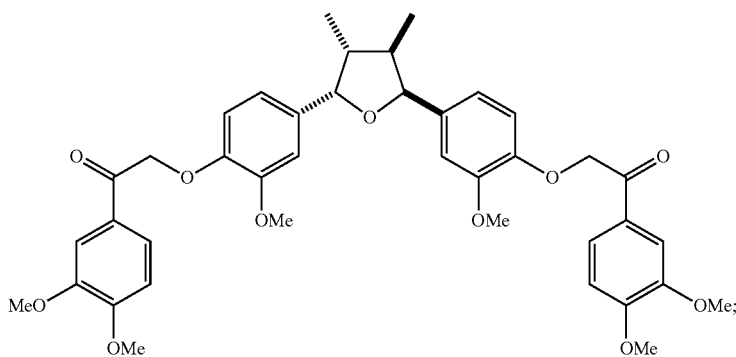
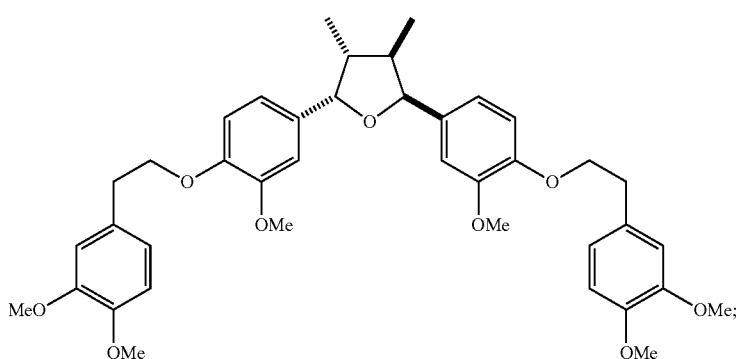

-continued
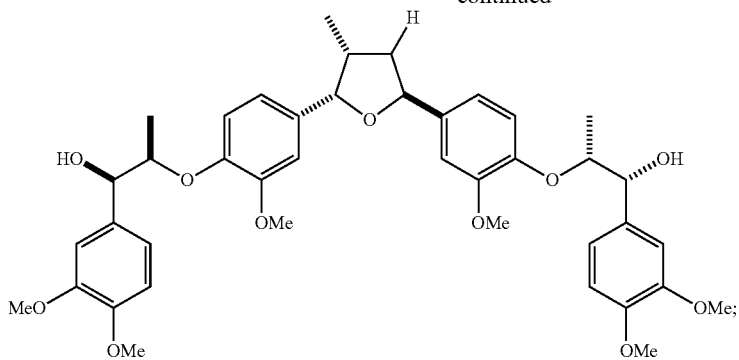
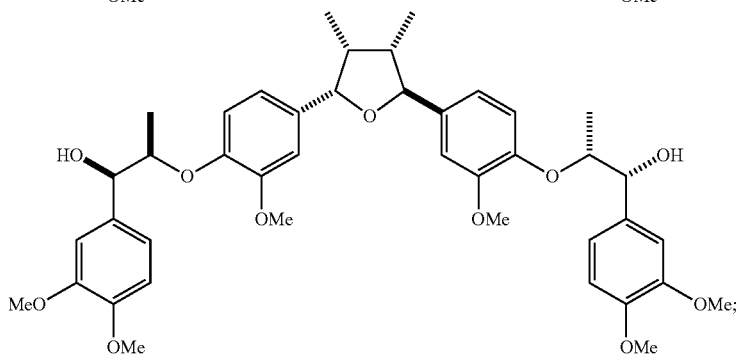
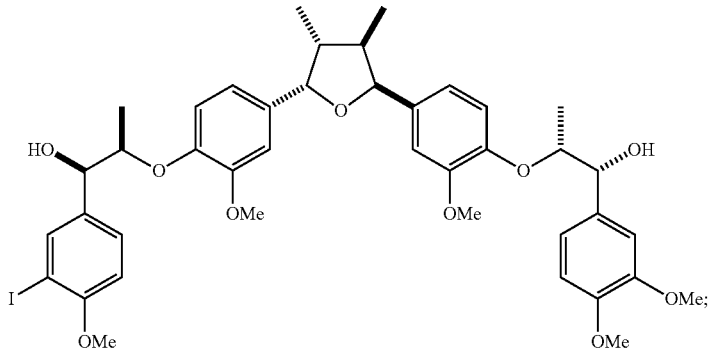
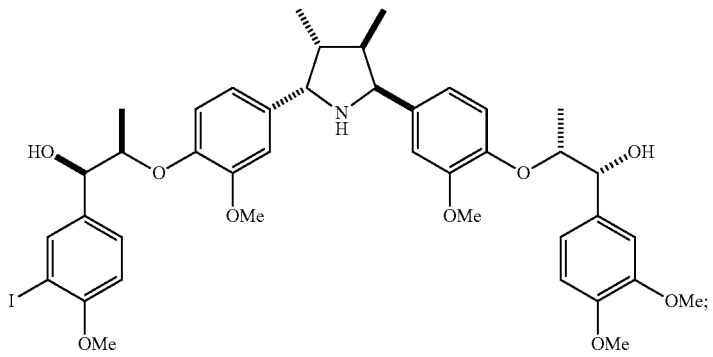
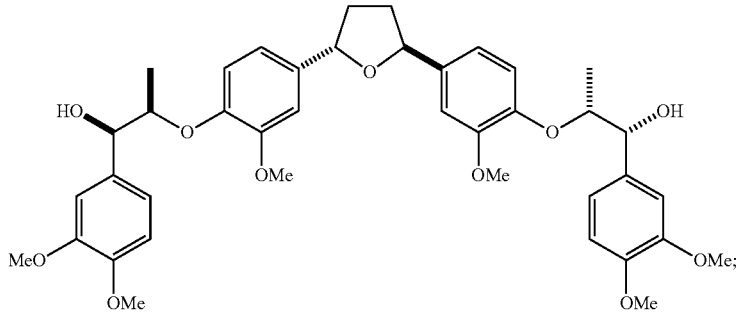

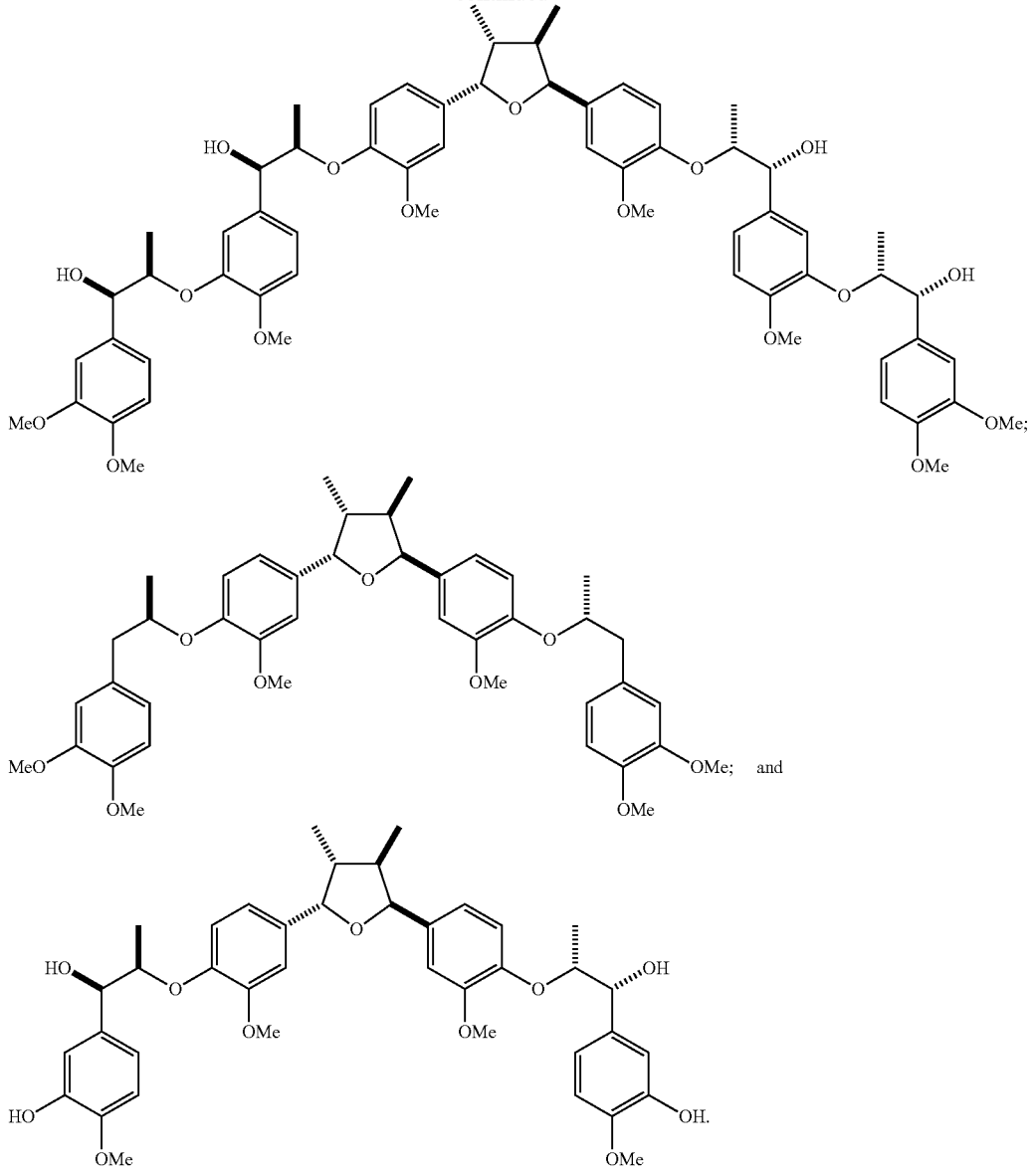

We claim:

1. A method of treating a disease, the method comprising administering to a patient in need thereof an effective amount of a compound according to Formula I:

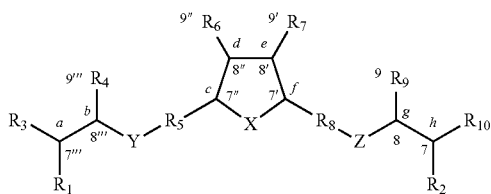

(I)

wherein $R_4$, $R_6$, $R_7$, and $R_9$ are independently selected from alkyl and hydrogen;

X, Y, and Z are independently selected from the group consisting of O and $NR_{14}$, wherein $R_{13}$ and $R_{14}$ are independently selected from the group consisting of alkyl, heteroalkyl, aryl, heteroaryl, ester, acyl, sulfonyl, heterocyclyl, amido, thioamido, acetyl, hydroxyl, amino, hydrogen, halogen, and cyano;

$R_3$ and $R_{10}$ are independently selected from the group consisting of hydrogen, alkyl, and oxo;

$R_5$ and $R_8$ are independently selected from the group consisting of substituted or unsubstituted phenyl; and $R_1$ and $R_2$ are independently selected from the group consisting of substituted or unsubstituted phenyl of Formula II below:

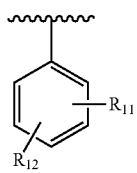

(II)

wherein $R_{11}$ and $R_{12}$ are independently selected from the group consisting of heteroalkyl, hydroxyl, hydrogen, halogen, and substituted alkylaryl; and wherein the disease is selected from the group consisting of leukemia, lung cancer, colon cancer, CNS cancer, melanoma, ovarian cancer, renal cancer, liver cancer, prostate cancer, breast cancer, stroke, heart disease, arthritis, ocular neovascular diseases, inflammation, kidney disease, and anemia.

2. The method of claim 1, wherein the disease is selected from the group consisting of leukemia, lung cancer, colon cancer, CNS cancer, melanoma, ovarian cancer, renal cancer, liver cancer, prostate cancer, and breast cancer.

3. The method of claim 1, wherein the disease is selected from the group consisting of leukemia, melanoma, and ovarian cancer.

4. The method of claim 1, wherein $R_1$ and $R_2$ are of Formula II wherein $R_{11}$ and $R_{12}$ are independently selected from H and methoxy groups.

5. The method of claim 1, wherein X, Y, and Z are O.

6. The method of claim 1, wherein $R_6$ and $R_7$ are independently selected from H and methyl groups.

7. The method of claim 1, wherein $R_5$ and $R_8$ are methoxy-substituted phenyl groups.

8. The method of claim 1, wherein $R_4$ and $R_9$ are independently selected from hydrogen and methyl groups, and wherein $R_3$ and $R_{10}$ are independently selected from hydrogen, oxo, and methyl groups.

9. The method of claim 1, wherein $R_1$ and $R_2$ are of Formula II wherein $R_{11}$ and $R_{12}$ are independently selected from H and methoxy groups; X, Y, and Z are O; $R_6$ and $R_7$ are independently selected from H and methyl groups; $R_5$ and $R_8$ are methoxy-substituted phenyl groups; and $R_4$ and $R_9$ are independently selected from hydrogen and methyl groups, and wherein $R_3$ and $R_{10}$ are independently selected from hydrogen, oxo, and methyl groups.

10. The method of claim 1, wherein the bonds c and f are trans to each other.

11. The method of claim 1, wherein the compound is selected from the following:

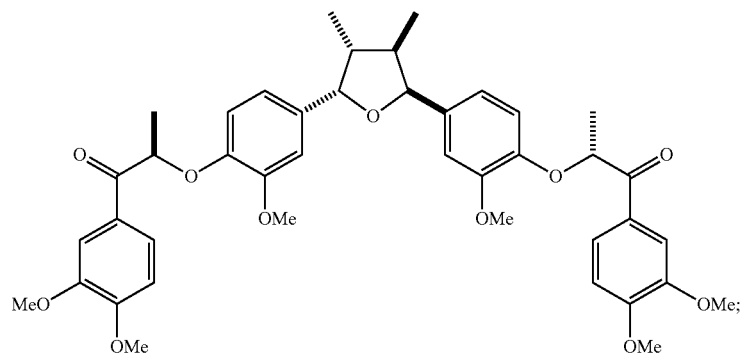

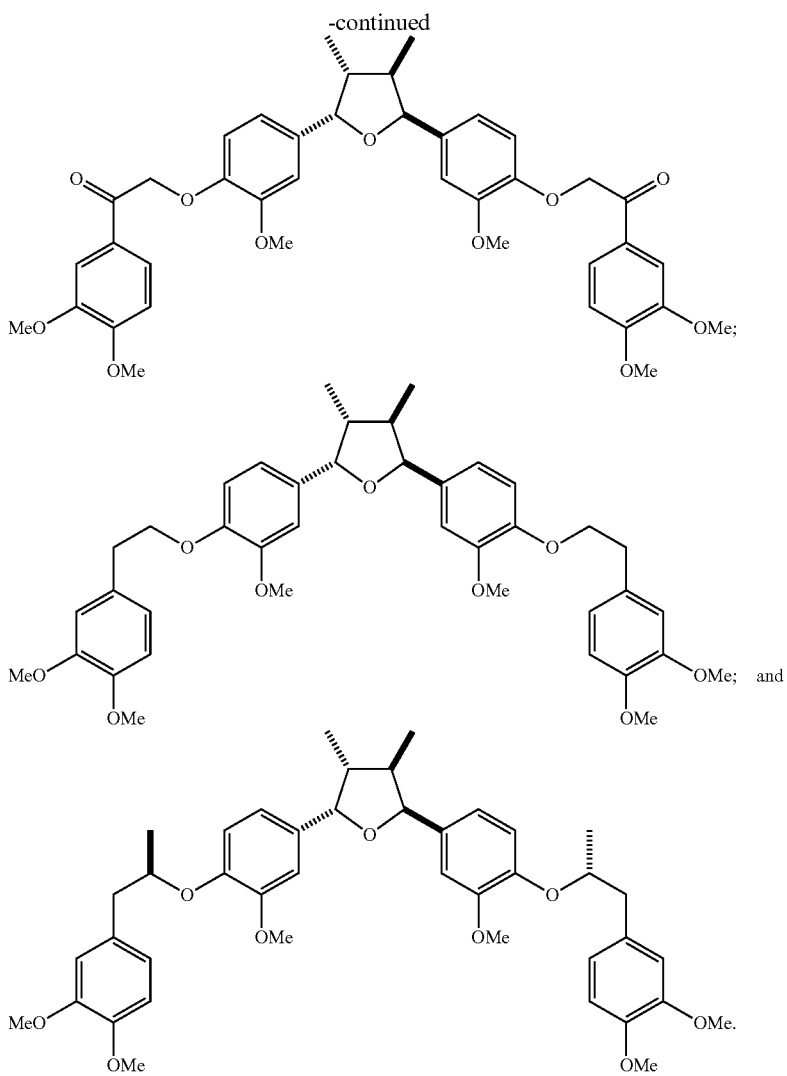

12. The method of claim 1, wherein administration is oral, sublingual, intramuscular, subcutaneous, intravenous, or transdermal.

13. A pharmaceutical composition comprising a pharmaceutically acceptable carrier and a compound according to Formula I:

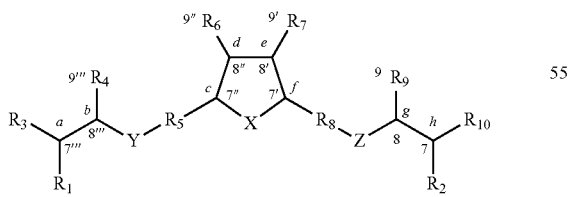

(I)

wherein $R_4$, $R_6$, $R_7$, and $R_9$ are independently selected from alkyl and hydrogen;

X, Y, and Z are independently selected from the group consisting of O and $NR_{14}$, wherein $R_{13}$ and $R_{14}$ are independently selected from the group consisting of alkyl, heteroalkyl, aryl, heteroaryl, ester, acyl, sulfonyl, heterocyclyl, amido, thioamido, acetyl, hydroxyl, amino, hydrogen, halogen, and cyano;

$R_3$ and $R_{10}$ are independently selected from the group consisting of hydrogen, alkyl, and oxo;

$R_5$ and $R_8$ are independently selected from the group consisting of substituted or unsubstituted phenyl; and $R_1$ and $R_2$ are independently selected from the group consisting of substituted or unsubstituted phenyl of Formula II below:

(II)

wherein $R_{11}$ and $R_{12}$ are independently selected from the group consisting of heteroalkyl, hydroxyl, hydrogen, halogen, and substituted alkylaryl.

14. A compound according to Formula I:

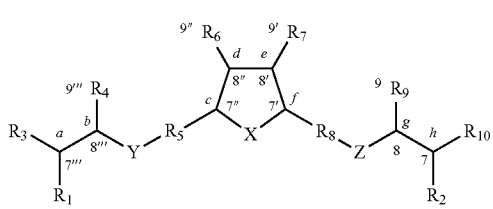

(I)

wherein $R_4$, $R_6$, $R_7$, and $R_9$ are independently selected from alkyl, and hydrogen;

X, Y, and Z are independently selected from the group consisting of O and $NR_{14}$, wherein $R_{13}$ and $R_{14}$ are independently selected from the group consisting of alkyl, heteroalkyl, aryl, heteroaryl, ester, acyl, sulfonyl, heterocyclyl, amido, thioamido, acetyl, hydroxyl, amino, hydrogen, halogen, and cyano;

$R_3$ and $R_{10}$ are independently selected from the group consisting of hydrogen, alkyl, and oxo;

$R_5$ and $R_8$ are independently selected from the group consisting of substituted or unsubstituted phenyl; and $R_1$ and $R_2$ are independently selected from the group consisting of substituted or unsubstituted phenyl of Formula II below:

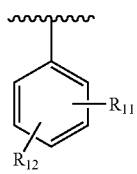

(II)

wherein $R_{11}$ and $R_{12}$ are independently selected from the group consisting of heteroalkyl, hydroxyl, hydrogen, halogen, and substituted alkylaryl.

15. The compound of claim 14, wherein $R_1$ and $R_2$ are of Formula II wherein $R_{11}$ and $R_{12}$ are independently selected from H and methoxy groups.

16. The compound of claim 14, wherein X, Y, and Z are O.

17. The compound of claim 14, wherein $R_6$ and $R_7$ are independently selected from H and methyl groups.

18. The compound of claim 14, wherein $R_5$ and $R_8$ are methoxy-substituted phenyl groups.

19. The compound of claim 14, wherein $R_4$ and $R_9$ are independently selected from hydrogen and methyl groups, and wherein $R_3$ and $R_{10}$ are independently selected from hydrogen, oxo, and methyl groups.

20. A method of inhibiting HIF-1 in a cell, the method comprising contacting the cell with a compound according to Formula I:

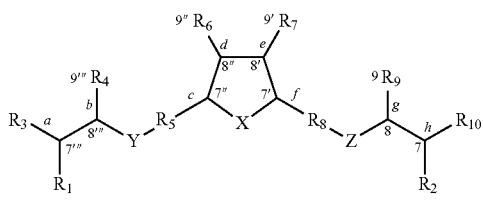

(I)

wherein $R_4$, $R_6$, $R_7$, and $R_9$ are independently selected from alkyl, and hydrogen;

X, Y, and Z are independently selected from the group consisting of O and $NR_{14}$, wherein $R_{13}$ and $R_{14}$ are independently selected from the group consisting of alkyl, heteroalkyl, aryl, heteroaryl, ester, acyl, sulfonyl, heterocyclyl, amido, thioamido, acetyl, hydroxyl, amino, hydrogen, halogen, and cyano;

$R_3$ and $R_{10}$ are independently selected from the group consisting of hydrogen, alkyl, and oxo;

$R_5$ and $R_8$ are independently selected from the group consisting of substituted or unsubstituted phenyl; and $R_1$ and $R_2$ are independently selected from the group consisting of substituted or unsubstituted phenyl of Formula II below:

(II)

wherein $R_{11}$ and $R_{12}$ are independently selected from the group consisting of heteroalkyl, hydroxyl, hydrogen, halogen, and substituted alkylaryl;

in an amount effective to inhibit the HIF-1 pathway.

21. A method of treating an individual with a disorder associated with increased activity of the HIF-1 pathway, the method comprising administering to the individual to treat the disorder an effective amount of a compound according to Formula I:

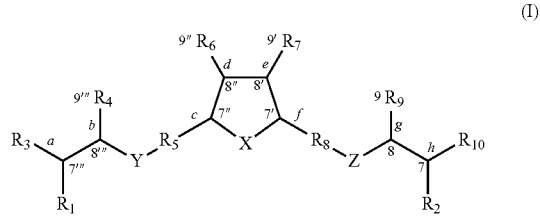

(I)

wherein $R_4$, $R_6$, $R_7$, and $R_9$ are independently selected from alkyl and hydrogen;

X, Y, and Z are independently selected from the group consisting of O and $NR_{14}$, wherein $R_{13}$ and $R_{14}$ are independently selected from the group consisting of alkyl, heteroalkyl, aryl, heteroaryl, ester, acyl, sulfonyl, heterocyclyl, amido, thioamido, acetyl, hydroxyl, amino, hydrogen, halogen, and cyano;

$R_3$ and $R_{10}$ are independently selected from the group consisting of hydrogen, alkyl, and oxo;

$R_5$ and $R_8$ are independently selected from the group consisting of substituted or unsubstituted phenyl; and $R_1$ and $R_2$ are independently selected from the group consisting of substituted or unsubstituted phenyl of Formula II below:

(II)

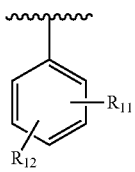

wherein $R_{11}$ and $R_{12}$ are independently selected from the group consisting of heteroalkyl, hydroxyl, hydrogen, halogen, and substituted alkylaryl.

22. A method of potentiating a cancer cell for treatment with ionizing radiation or chemotherapeutics comprising contacting the cancer cell with an effective amount of a compound according to Formula I:

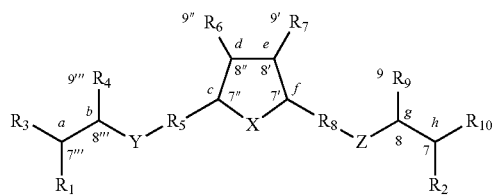

(I)

wherein $R_4$, $R_6$, $R_7$, and $R_9$ are independently selected from alkyl, and hydrogen;

X, Y, and Z are independently selected from the group consisting of O and $NR_{14}$, wherein $R_{13}$ and $R_{14}$ are independently selected from the group consisting of alkyl, heteroalkyl, aryl, heteroaryl, ester, acyl, sulfonyl, heterocyclyl, amido, thioamido, acetyl, hydroxyl, amino, hydrogen, halogen, and cyano;

$R_3$ and $R_{10}$ are independently selected from the group consisting of hydrogen, alkyl, and oxo;

$R_5$ and $R_8$ are independently selected from the group consisting of substituted or unsubstituted phenyl; and $R_1$ and $R_2$ are independently selected from the group consisting of substituted or unsubstituted phenyl of Formula II below:

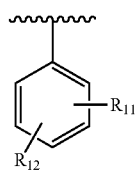

(II)

wherein $R_{11}$ and $R_{12}$ are independently selected from the group consisting of heteroalkyl, hydroxyl, hydrogen, halogen, and substituted alkylaryl.

23. A compound selected from the following: